US009684238B2

(12) United States Patent
Harihara et al.

(10) Patent No.: US 9,684,238 B2
(45) Date of Patent: Jun. 20, 2017

(54) FLUORENE-TYPE COMPOUND, PHOTOPOLYMERIZATION INITIATOR COMPRISING SAID FLUORENE-TYPE COMPOUND, AND PHOTOSENSITIVE COMPOSITION CONTAINING SAID PHOTOPOLYMERIZATION INITIATOR

(71) Applicant: TOKYO OHKA KOGYO CO., LTD., Kawasaki-shi (JP)

(72) Inventors: Makoto Harihara, Osaka (JP); Tomohiko Yamazaki, Osaka (JP); Katsuji Kuwamura, Osaka (JP)

(73) Assignee: TOKYO OHKA KOGYO CO., LTD., Kawasaki-shi (JP)

( * ) Notice: Subject to any disclaimer, the term of this patent is extended or adjusted under 35 U.S.C. 154(b) by 0 days.

(21) Appl. No.: 14/431,813

(22) PCT Filed: Sep. 20, 2013

(86) PCT No.: PCT/JP2013/075477
§ 371 (c)(1),
(2) Date: Jun. 1, 2015

(87) PCT Pub. No.: WO2014/050738
PCT Pub. Date: Apr. 3, 2014

(65) Prior Publication Data
US 2015/0259321 A1    Sep. 17, 2015

(30) Foreign Application Priority Data

Sep. 28, 2012 (JP) ................................. 2012-217856

(51) Int. Cl.
*G03F 7/028* (2006.01)
*G03F 7/029* (2006.01)
*G03F 7/031* (2006.01)
*C07C 251/02* (2006.01)
*C07C 251/24* (2006.01)
*C07C 251/56* (2006.01)
*C07C 251/66* (2006.01)
*C07C 259/06* (2006.01)
*C07D 333/22* (2006.01)
*C07D 333/34* (2006.01)
*C08F 2/48* (2006.01)
*C08F 4/00* (2006.01)

(52) U.S. Cl.
CPC ............ *G03F 7/028* (2013.01); *C07C 251/02* (2013.01); *C07C 251/24* (2013.01); *C07C 251/56* (2013.01); *C07C 251/66* (2013.01); *C07C 259/06* (2013.01); *C07D 333/22* (2013.01); *C07D 333/34* (2013.01); *C08F 2/48* (2013.01); *C08F 4/00* (2013.01); *G03F 7/029* (2013.01); *G03F 7/031* (2013.01); *C07C 2103/18* (2013.01)

(58) Field of Classification Search
None
See application file for complete search history.

(56) References Cited

U.S. PATENT DOCUMENTS

| | | | |
|---|---|---|---|
| 6,949,678 B2 | 9/2005 | Kunimoto et al. | |
| 7,381,842 B2 | 6/2008 | Kunimoto et al. | |
| 8,202,679 B2 | 6/2012 | Sawamoto et al. | |
| 2001/0012596 A1 | 8/2001 | Kunimoto et al. | |
| 2005/0191567 A1 | 9/2005 | Kunimoto et al. | |
| 2010/0249262 A1 | 9/2010 | Sawamoto et al. | |
| 2015/0111152 A1* | 4/2015 | Shin ........................ | G03F 7/105 430/281.1 |
| 2016/0214966 A1* | 7/2016 | Kunimoto ............... | G03F 7/031 |

FOREIGN PATENT DOCUMENTS

| | | |
|---|---|---|
| CN | 1299812 A | 6/2001 |
| CN | 104661997 A | 5/2015 |
| JP | 2001-233842 A | 8/2001 |
| JP | 2006-36750 A | 2/2006 |
| JP | 2008-37930 * | 2/2008 |
| JP | 2008-037930 A | 2/2008 |
| JP | 2008-100955 A | 5/2008 |
| JP | 2008-261921 A | 10/2008 |
| JP | 2010-015025 A | 1/2010 |
| JP | 2010-037215 A | 2/2010 |
| KR | 10-2009-0008811 A | 1/2009 |
| KR | 10-2010-0097658 A | 9/2010 |
| TW | 200930694 A | 7/2009 |
| WO | 02/100903 A1 | 12/2002 |

(Continued)

OTHER PUBLICATIONS

JPO English abstract for JP2008-37930 (2008).*
Machine-assisted English translation of JP2008-37930 provided by JPO (2008).*
JPO English abstract for JP2010-15025 (2010).*
Office Action in Chinese Application No. 201380050762.6, dated Aug. 7, 2015.

*Primary Examiner* — Sin Lee
(74) *Attorney, Agent, or Firm* — Knobbe Martens Olson & Bear LLP

(57) ABSTRACT

According to an embodiment of the present invention, there is provided a novel fluorene-based compound and a photopolymerization initiator using the fluorene-based compound. The fluorene-based compound according to an embodiment of the present invention is represented by the general formula (1). A photopolymerization initiator having additionally high sensitivity can be provided by using the fluorene-based compound. In addition, a photopolymerization initiator that can impart additionally excellent characteristics can be provided by appropriately selecting, for example, a substituent.

13 Claims, 11 Drawing Sheets

(56) References Cited

FOREIGN PATENT DOCUMENTS

| WO | 2007/080947 A1 | 7/2007 |
| WO | 2011/152066 A1 | 12/2011 |
| WO | WO2013/165207 A1 * | 11/2013 |
| WO | WO 2015/036910 A1 | 3/2015 |

* cited by examiner

FIG. 6

| EXPOSURE ENERGY QUANTITY (mJ/cm²) | COMPARATIVE EXAMPLE 1 (REFERENCE EXAMPLE 1) | COMPARATIVE EXAMPLE 3 (REFERENCE EXAMPLE 1) |
|---|---|---|
| 10 | CURED FILM IS NOT FORMED | |
| 20 | | |
| 40 | | |
| 60 | | |
| 80 | | |

FIG. 7

| EXPOSURE ENERGY QUANTITY (mJ/cm²) | EXAMPLE 2-1 (COMPOUND D-1) | EXAMPLE 2-11 (COMPOUND D-1) |
|---|---|---|
| 5 | NO DATA | NO DATA |
| 10 | | |
| 20 | | |
| 40 | | |
| 60 | | |
| 80 | | |

FIG. 8

| EXPOSURE ENERGY QUANTITY (mJ/cm²) | EXAMPLE 2-2 (COMPOUND D-3) | EXAMPLE 2-13 (COMPOUND D-3) |
|---|---|---|
| 5 |  | NO DATA |
| 10 |  |  |
| 20 |  |  |
| 40 |  |  |
| 60 | NO DATA |  |
| 80 |  |  |

FIG. 9

| EXPOSURE ENERGY QUANTITY (mJ/cm²) | EXAMPLE 2-3 (COMPOUND D-4) | EXAMPLE 2-14 (COMPOUND D-4) |
|---|---|---|
| 5 | | NO DATA |
| 10 | | |
| 20 | | |
| 40 | | |
| 60 | NO DATA | |
| 80 | | |

FIG. 10

| EXPOSURE ENERGY QUANTITY (mJ/cm²) | EXAMPLE 2-7 (COMPOUND D-12) | EXAMPLE 2-17 (COMPOUND D-12) |
|---|---|---|
| 5 | | NO DATA |
| 10 | | |
| 20 | | |
| 40 | | |
| 60 | NO DATA | |
| 80 | | |

FIG. 11

| EXPOSURE ENERGY QUANTITY (mJ/cm²) | EXAMPLE 2-8 (COMPOUND D-14) | EXAMPLE 2-18 (COMPOUND D-14) |
|---|---|---|
| 5 | | NO DATA |
| 10 | | |
| 20 | | |
| 40 | | |
| 60 | NO DATA | |
| 80 | | |

FLUORENE-TYPE COMPOUND, PHOTOPOLYMERIZATION INITIATOR COMPRISING SAID FLUORENE-TYPE COMPOUND, AND PHOTOSENSITIVE COMPOSITION CONTAINING SAID PHOTOPOLYMERIZATION INITIATOR

TECHNICAL FIELD

The present invention relates to a fluorene-based compound, a photopolymerization initiator containing the fluorene-based compound, and a photosensitive composition containing the photopolymerization initiator.

BACKGROUND ART

In general, a photosensitive composition containing a compound having an ethylenically unsaturated bond and a photopolymerization initiator can be cured by being irradiated with an active energy ray. Accordingly, the photosensitive composition has been used in various applications such as a photocurable adhesive, a photocurable ink, a photosensitive printing plate, and various photoresists.

For example, oxime ester compounds each containing a carbazole skeleton have been known as photopolymerization initiators (for example, Patent Literatures 1 to 3). Those compounds have been suitably used because the compounds each have excellent sensitivity to an active energy ray. However, the development of a photopolymerization initiator that is more excellent in sensitivity to the active energy ray than those compounds are has been demanded. In addition, those compounds are susceptible to improvement in terms of solubility. Further, a photopolymerization initiator is used in various applications, and hence it has been demanded that the photopolymerization initiator have excellent performance concerning characteristics required in the respective applications in addition to high sensitivity to the active energy ray.

In addition, Patent Literatures 4 and 5 each disclose an oxime ester compound having a fluorene skeleton. However, the literatures do not have any specific disclosure concerning, for example, a method of synthesizing the compound, and whether the compound is useful as a photopolymerization initiator is unclear.

CITATION LIST

Patent Literature

[PTL 1] JP 2006-36750 A
[PTL 2] WO 2002/100903 A1
[PTL 3] WO 2011/152066 A1
[PTL 4] JP 2008-100955 A
[PTL 5] JP 2010-15025 A

SUMMARY OF INVENTION

Technical Problem

An object of the present invention is to solve the problems of the above-mentioned conventional compounds, in other words, to provide a novel compound having a fluorene skeleton, a photopolymerization initiator containing the compound, and a photosensitive composition containing the photopolymerization initiator and excellent in sensitivity to an active energy ray.

Solution to Problem

The inventors of the present invention have made extensive investigations, and as a result, have found that the object can be achieved by using a novel compound having a fluorene skeleton whose 2- and 7-positions are substituted. Thus, the inventors have completed the present invention.

A fluorene-based compound of the present invention is represented by the general formula (1):

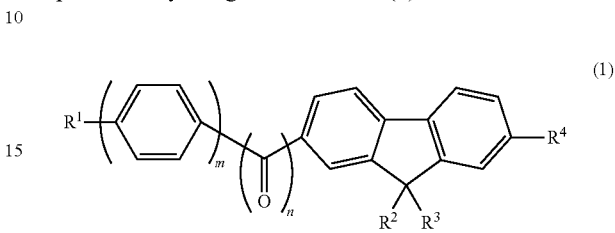

in the general formula (1):

when m represents 0 and n represents 0, $R^1$ represents a hydrogen atom, a halogen atom, a nitro group, a sulfonyloxy group substituted with an alkyl group having 1 to 8 carbon atoms that may be substituted with a halogen atom, a phenylsulfonyloxy group that may be substituted, a sulfonyl group substituted with an alkyl group having 1 to 8 carbon atoms that may be substituted with a halogen atom, a phenylsulfonyl group that may be substituted, a heterocyclic sulfonyl group that may be substituted, or a condensed ring sulfonyl group that may be substituted, when m represents 0 and n represents 1, $R^1$ represents a phenyl group that may be substituted, a heterocyclic group that may be substituted, or a condensed ring group that may be substituted, and when m represents 1 and n represents 1, $R^1$ represents a sulfonyloxy group substituted with an alkyl group having 1 to 8 carbon atoms that may be substituted with a halogen atom, or a phenylsulfonyloxy group that may be substituted;

$R^2$ and $R^3$ each independently represent a hydrogen atom, a linear, branched, or cyclic alkyl group having 1 to 22 carbon atoms, a linear or branched halogenated alkyl group having 1 to 10 carbon atoms, a linear or branched alkyl group having 2 to 15 carbon atoms interrupted by one or more ether bonds or thioether bonds, a phenyl group that may be substituted, or a phenylalkyl group having 7 to 11 carbon atoms, and $R^2$ and $R^3$ may form a ring together;

$R^4$ represents a group represented by the formula (2) or the formula (3):

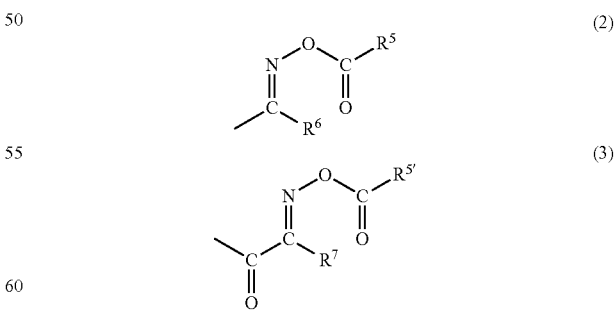

in the formulae (2) and (3), $R^5$ and $R^{5'}$ each represent a linear, branched, or cyclic alkyl group having 1 to 17 carbon atoms, a linear or branched halogenated alkyl group having 2 to 5 carbon atoms, a linear or branched alkyl group having 2 to 7 carbon atoms interrupted by one or more ether bonds or thioether bonds, a phenyl group that may be substituted, a phenylalkyl group having 7 to 11 carbon atoms that may be substituted, a phenoxyalkyl group having 7 to 10 carbon atoms that may be substituted, a heterocyclic group that may be substituted, or a condensed ring group that may be substituted, in the formula (2), $R^6$ represents a linear, branched, or cyclic alkyl group having 1 to 17 carbon atoms, a linear or branched halogenated alkyl group having 1 to 7 carbon atoms, a linear or branched alkyl group having 2 to 7 carbon atoms interrupted by one or more ether bonds or thioether bonds, a linear or branched aminoalkyl group having 2 to 4 carbon atoms that may be substituted, a phenyl group that may be substituted, a phenylalkyl group having 7 to 11 carbon atoms that may be substituted, a phenylalkyl group having 7 to 10 carbon atoms that is interrupted by one or more ether bonds or thioether bonds and may be substituted, a condensed ring group that may be substituted, or a heterocyclic group that may be substituted, and in the formula (3), $R^7$ represents a linear, branched, or cyclic alkyl group having 1 to 16 carbon atoms, a linear or branched halogenated alkyl group having 1 to 6 carbon atoms, a phenyl group that may be substituted, a phenylalkyl group having 7 to 10 carbon atoms that may be substituted, a phenylalkyl group having 7 to 9 carbon atoms that is interrupted by one or more ether bonds or thioether bonds and may be substituted, a condensed ring group that may be substituted, or a heterocyclic group that may be substituted; and m and n each represent 0 or 1, and when m represents 1, n represents 1.

In a preferred embodiment, the $R^5$ or the $R^{5'}$ represents a methyl group.

In a preferred embodiment, the $R^4$ represents a group represented by the formula (2), and the $R^6$ represents a linear, branched, or cyclic alkyl group having 1 to 7 carbon atoms, a linear or branched halogenated alkyl group having 1 to 5 carbon atoms, a linear or branched aminoalkyl group having 2 to 4 carbon atoms that may be substituted, a phenyl group that may be substituted, a phenylalkyl group having 7 to 11 carbon atoms that may be substituted, a phenylalkyl group having 7 to 10 carbon atoms that is interrupted by one or more ether bonds or thioether bonds and may be substituted, a condensed ring group that may be substituted, or a heterocyclic group that may be substituted.

In a preferred embodiment, the $R^4$ represents a group represented by the formula (3), and the $R^7$ represents a linear, branched, or cyclic alkyl group having 1 to 6 carbon atoms, a linear or branched halogenated alkyl group having 1 to 4 carbon atoms, a phenyl group that may be substituted, a phenylalkyl group having 7 to 10 carbon atoms that may be substituted, a phenylalkyl group having 7 to 9 carbon atoms that is interrupted by one or more ether bonds or thioether bonds and may be substituted, a condensed ring group that may be substituted, or a heterocyclic group that may be substituted.

In a preferred embodiment, the m and the n each represent 0, and the $R^1$ represents a halogen atom or a nitro group; or the m represents 0 and the n represents 1, and the $R^1$ represents a phenyl group that may be substituted, a condensed ring group that may be substituted, or a heterocyclic group that may be substituted.

In another aspect of the present invention, there is provided a photopolymerization initiator. The photopolymerization initiator contains at least one kind of the fluorene-based compound.

In still another aspect of the present invention, there is provided a photosensitive composition. The photosensitive composition contains a compound having at least one ethylenically unsaturated bond and the photopolymerization initiator.

Advantageous Effects of Invention

The novel fluorene-based compound of the present invention has high sensitivity to an active energy ray. In addition, a photopolymerization initiator having additionally excellent characteristics (such as additionally improved sensitivity to the active energy ray, high solubility, and additionally excellent transparency) can be provided by appropriately selecting a functional group to be bonded to the fluorene skeleton of the fluorene-based compound of the present invention. Accordingly, the fluorene-based compound of the present invention can be suitably used as a photopolymerization initiator in various applications.

BRIEF DESCRIPTION OF DRAWINGS

In FIG. 6, laser microscope photographs of a transparent cured film (Comparative Example 1) and a black cured film (Comparative Example 3) each obtained from a photosensitive composition containing a conventional photopolymerization initiator are shown.

In FIG. 7, laser microscope photographs of a transparent cured film (Example 2-1) and a black cured film (Example 2-11) each obtained from a photosensitive composition containing a fluorene-based compound obtained in Synthesis Example D-1 are shown.

In FIG. 8 laser microscope photographs of a transparent cured film (Example 2-2) and a black cured film (Example 2-13) each obtained from a photosensitive composition containing a fluorene-based compound obtained in Synthesis Example D-3 are shown.

In FIG. 9, laser microscope photographs of a transparent cured film (Example 2-3) and a black cured film (Example 2-14) each obtained from a photosensitive composition containing a fluorene-based compound obtained in Synthesis Example D-4 are shown.

In FIG. 10, laser microscope photographs of a transparent cured film (Example 2-7) and a black cured film (Example 2-17) each obtained from a photosensitive composition containing a fluorene-based compound obtained in Synthesis Example D-12 are shown.

In FIG. 11, laser microscope photographs of a transparent cured film (Example 2-8) and a black cured film (Example 2-18) each obtained from a photosensitive composition containing a fluorene-based compound obtained in Synthesis Example D-14 are shown.

DESCRIPTION OF EMBODIMENTS

A. Fluorene-Based Compound

Figure 1A:
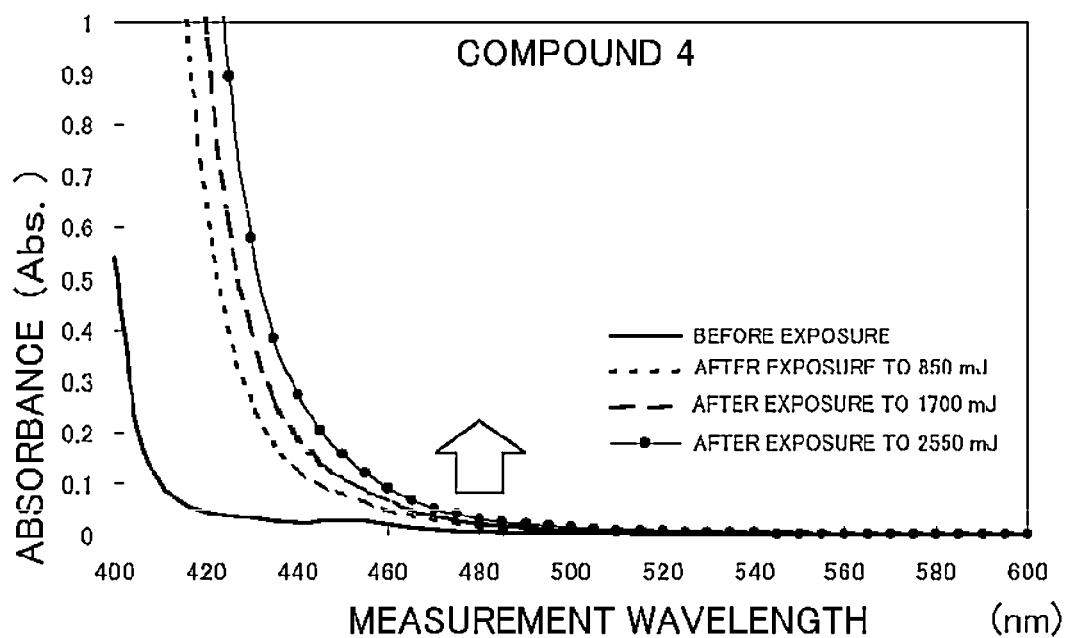
FIG. 1(A) is a graph for showing the results of the measurement of the degrees of coloring (absorption spectra) of a fluorene-based compound obtained in Synthesis Example 4 before and after its exposure.

A-1. Fluorene-Based Compound of the Present Invention

A fluorene-based compound of the present invention is represented by the general formula (1).

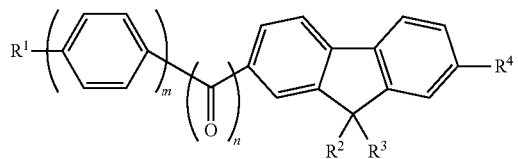

(1)

In the general formula (1), when m represents 0 and n represents 0, i.e., when $R^1$ is directly bonded to a fluorene skeleton, $R^1$ represents a hydrogen atom, a halogen atom, a nitro group, a sulfonyloxy group substituted with an alkyl group having 1 to 8 carbon atoms that may be substituted with a halogen atom, a phenylsulfonyloxy group that may be substituted, a sulfonyl group substituted with an alkyl group having 1 to 8 carbon atoms that may be substituted with a halogen atom, a phenylsulfonyl group that may be substituted, a heterocyclic sulfonyl group that may be substituted, or a condensed ring sulfonyl group that may be substituted. In the general formula (1), when m represents 0 and n represents 0, $R^1$ preferably represents a halogen atom or a nitro group.

Specifically, when m represents 0 and n represents 0, $R^1$ represents a hydrogen atom, a halogen atom, a nitro group, an alkylsulfonyloxy group represented by the following formula:

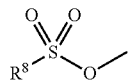

(in the formula, $R^8$ represents a linear, branched, or cyclic alkyl group having 1 to 8 carbon atoms, or a linear halogenated alkyl group having 1 to 4 carbon atoms), a phenylsulfonyloxy group that may be substituted, the group being represented by the following formula:

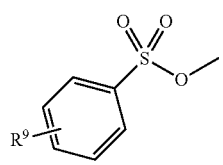

(in the formula, $R^9$ represents a hydrogen atom, a linear or branched alkyl group having 1 to 4 carbon atoms, a linear or branched alkoxy group having 1 to 4 carbon atoms, a halogen atom, a cyano group, an aryl group, or a nitro group), an alkylsulfonyl group represented by the following formula:

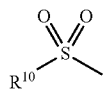

(in the formula, $R^{10}$ represents a linear, branched, or cyclic alkyl group having 1 to 8 carbon atoms, or a halogenated alkyl group having 1 to 4 carbon atoms), a phenylsulfonyl group that may be substituted, the group being represented by the following formula:

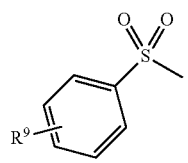

(in the formula, $R^{10}$ represents a hydrogen atom, a linear or branched alkyl group having 1 to 4 carbon atoms, a linear or branched alkoxy group having 1 to 4 carbon atoms, a halogen atom, a cyano group, an aryl group, or a nitro group), a heterocyclic sulfonyl group that may be substituted, the group being represented by any one of the following formulae:

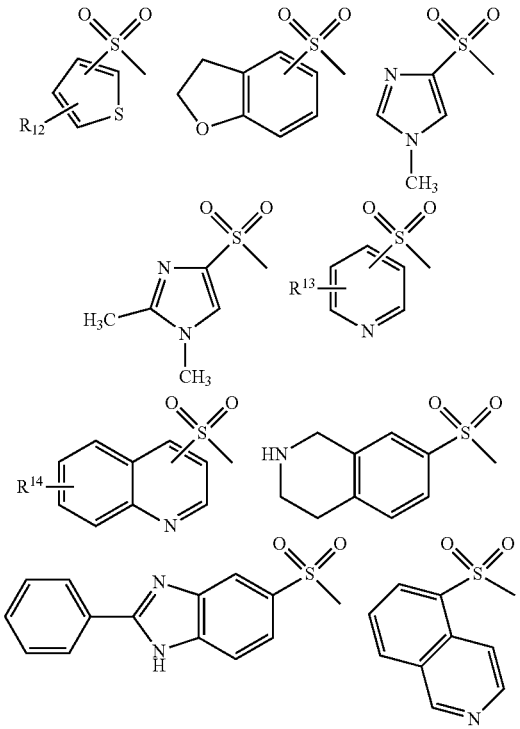

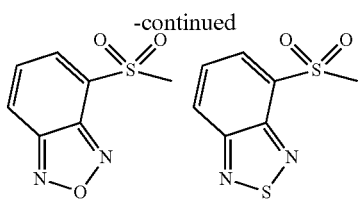

(in the formulae, $R^{12}$ represents a hydrogen atom or a halogen atom, $R^{13}$ represents a hydrogen atom, a hydroxyl group, or a linear or branched alkoxy group having 1 to 4 carbon atoms, and $R^{14}$ represents a hydrogen atom, a hydroxyl group, or a linear or branched alkoxy group having 1 to 4 carbon atoms), or a condensed ring sulfonyl group that may be substituted, the group being represented by any one of the following formulae:

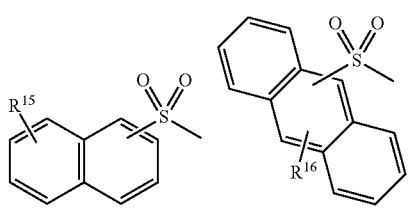

(in the formulae, $R^{15}$ represents a hydrogen atom, a linear or branched alkoxy group having 1 to 4 carbon atoms, a hydroxyl group, an amino group substituted with a linear or branched alkyl group having 1 to 4 carbon atoms, a halogen atom, or a nitro group, and $R^{16}$ represents a hydrogen atom, a linear or branched alkoxy group having 1 to 4 carbon atoms, a hydroxyl group, a halogen atom, or a nitro group).

The $R^8$ preferably represents a linear or branched alkyl group having 1 to 4 carbon atoms, and more preferably represents a methyl group. The $R^9$ preferably represents a hydrogen atom, a linear or branched alkyl group having 1 to 4 carbon atoms, a linear or branched alkoxy group having 1 to 4 carbon atoms, a halogen atom, a cyano group, or a nitro group, and more preferably represents a methyl group. Examples of the halogen atom include fluorine, chlorine, bromine, and iodine.

The $R^{10}$ preferably represents a linear or branched alkyl group having 1 to 4 carbon atoms, and more preferably represents a methyl group. The $R^{11}$ preferably represents a hydrogen atom, a linear or branched alkyl group having 1 to 4 carbon atoms, a linear or branched alkoxy group having 1 to 4 carbon atoms, a halogen atom, a cyano group, or a nitro group, and more preferably represents a methyl group. Examples of the halogen atom include fluorine, chlorine, bromine, and iodine.

The $R^{12}$ preferably represents a hydrogen atom or a halogen atom. The $R^{13}$ preferably represents a hydrogen atom, a methoxy group, an ethoxy group, or a hydroxyl group. The $R^{14}$ preferably represents a hydrogen atom, a methoxy group, an ethoxy group, or a hydroxyl group.

The $R^{15}$ preferably represents a hydrogen atom. The $R^{16}$ preferably represents a hydrogen atom. That is, it is preferred that when $R^1$ represents a condensed ring sulfonyl group, the condensed ring sulfonyl group be not substituted.

In the general formula (1), when m represents 0 and n represents 1, i.e., when $R^1$ is bonded to the fluorene skeleton through a carbonyl group, $R^1$ represents a phenyl group that may be substituted, a heterocyclic group that may be substituted, or a condensed ring group that may be substituted. In the general formula (1), when m represents 0 and n represents 1, $R^1$ preferably represents a phenyl group that may be substituted.

Specifically, when m represents 0 and n represents 1, a bonding portion with the fluorene skeleton including $R^1$ is a structure containing a substituted phenyl group represented by the following formula:

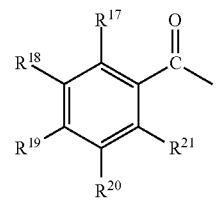

(in the formula, $R^{17}$ to $R^{21}$ each independently represent a hydrogen atom, a nitro group, an aryl group, a halogen atom, a cyano group, a linear, branched, or cyclic alkyl group having 1 to 7 carbon atoms, a linear or branched halogenated alkyl group having 1 to 4 carbon atoms, a linear or branched alkoxy group having 1 to 4 carbon atoms, or a linear or branched halogenated alkoxy group having 1 to 4 carbon atoms), a structure containing a heterocycle that may be substituted, the structure being represented by any one of the following formulae:

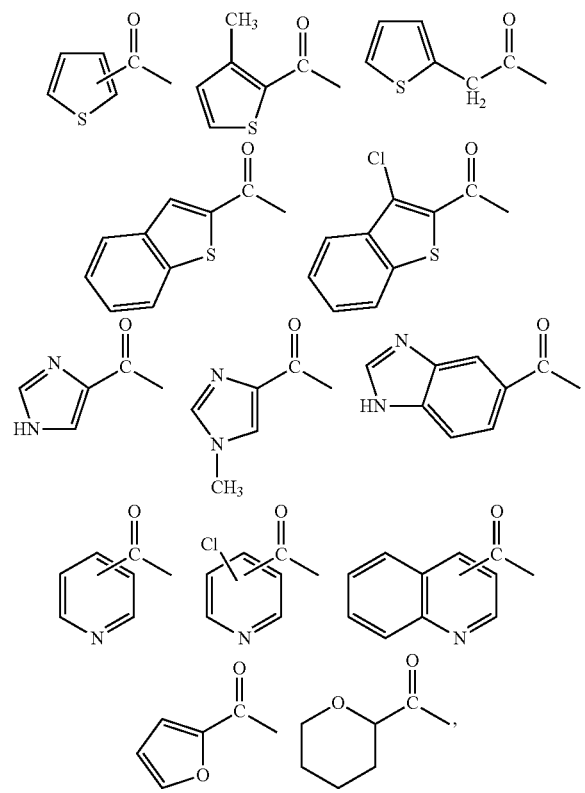

or a structure containing a condensed ring that may be substituted, the structure being represented by any one of the following formulae:

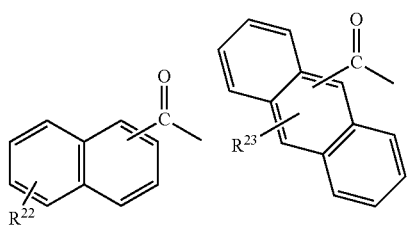

(in the formulae, $R^{22}$ represents a hydrogen atom, a nitro group, a hydroxyl group, a linear or branched alkyl group having 1 to 4 carbon atoms, or a linear or branched alkoxy group having 1 to 4 carbon atoms, and $R^{23}$ represents a hydrogen atom, a hydroxyl group, a halogen atom, a nitro group, a cyano group, a linear or branched alkyl group having 1 to 4 carbon atoms, or a linear or branched alkoxy group having 1 to 4 carbon atoms).

It is preferred that the $R^{17}$ to $R^{21}$ each independently represent a hydrogen atom, a nitro group, a halogen atom, a cyano group, a linear or branched alkyl group having 1 to 4 carbon atoms, a linear or branched alkoxy group having 1 to 4 carbon atoms, or a linear or branched halogenated alkyl group having 1 to 4 carbon atoms. Examples of the halogen atom with which a hydrogen atom of an alkyl group in the linear or branched halogenated alkyl group having 1 to 4 carbon atoms is substituted include the above-mentioned halogen atoms. Specific examples of the linear or branched alkyl group having 1 to 4 carbon atoms that is substituted with a halogen atom include a trifluoromethyl group, a pentafluoroethyl group, and a nonafluorobutyl group.

In addition, when at least one of the groups represented by the $R^{17}$ to $R^{21}$ is a nitro group, the other groups are preferably each independently a hydrogen atom, a halogen atom, a nitro group, or a linear or branched alkyl group having 1 to 4 carbon atoms.

The $R^{22}$ preferably represents a hydrogen atom, a methyl group, an ethyl group, a methoxy group, an ethoxy group, or a hydroxyl group. The $R^{23}$ preferably represents a hydrogen atom, a methyl group, an ethyl group, a methoxy group, an ethoxy group, a hydroxyl group, a halogen atom, or a cyano group.

In the general formula (1), when m represents 1 and n represents 1, i.e., when $R^1$ is bonded to the fluorene skeleton through a carbonyl group and a phenylene group, $R^2$ represents a sulfonyloxy group substituted with an alkyl group having 1 to 8 carbon atoms that may be substituted with a halogen atom (specifically a sulfonyloxy group substituted with a linear, branched, or cyclic alkyl group having 1 to 8 carbon atoms, or a sulfonyloxy group substituted with a linear halogenated alkyl group having 1 to 4 carbon atoms), or a phenylsulfonyloxy group that may be substituted.

Specifically, when m represents 1 and n represents 1, the bonding portion with the fluorene skeleton including $R^2$ is a sulfonyloxy group represented by the following formula:

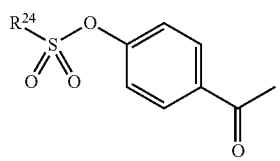

(in the formula, $R^{24}$ represents a linear, branched, or cyclic alkyl group having 1 to 8 carbon atoms, or a linear halogenated alkyl group having 1 to 4 carbon atoms), or a phenylsulfonyloxy group that may be substituted, the group being represented by the following formula:

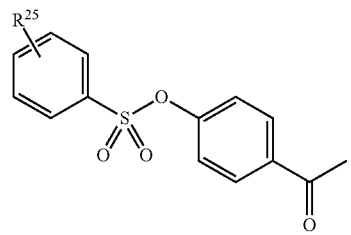

(in the formula, $R^{25}$ represents a hydrogen atom, a linear or branched alkyl group having 1 to 4 carbon atoms, a linear or branched alkoxy group having 1 to 4 carbon atoms, a halogen atom, a cyano group, or a nitro group).

The $R^{24}$ preferably represents a methyl group. The $R^{25}$ preferably represents a methyl group.

In the general formula (1), $R^2$ and $R^3$ each independently represent a linear, branched, or cyclic alkyl group having 1 to 22 carbon atoms, a linear or branched halogenated alkyl group having 1 to 10 carbon atoms, a linear or branched alkyl group having 2 to 15 carbon atoms interrupted by one or more ether bonds or thioether bonds, a phenyl group that may be substituted, or a phenylalkyl group having 7 to 11 carbon atoms that may be substituted. The $R^2$ and the $R^3$ may form a ring together. Examples of the halogen atom in the linear or branched halogenated alkyl group having 1 to 10 carbon atoms include the halogen atoms given in the foregoing.

The $R^2$ and the $R^3$ preferably each independently represent a hydrogen atom or a linear or branched alkyl group having 2 to 8 carbon atoms.

In the general formula (1), $R^4$ represents a group represented by the formula (2) or the formula (3). In the general formula (1), $R^4$ preferably represents a group represented by the formula (2).

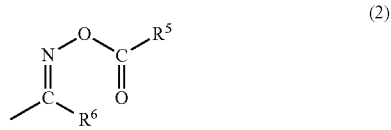

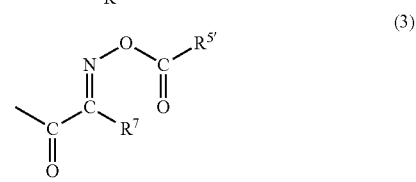

In the formulae (2) and (3), $R^5$ and $R^{5'}$ each represent a linear, branched, or cyclic alkyl group having 1 to 17 carbon atoms, a linear or branched halogenated alkyl group having 2 to 5 carbon atoms, a linear or branched alkyl group having 2 to 7 carbon atoms interrupted by one or more ether bonds or thioether bonds, a phenyl group that may be substituted, a phenylalkyl group having 7 to 11 carbon atoms that may be substituted, a phenoxyalkyl group having 7 to 10 carbon atoms that may be substituted, a heterocyclic group that may be substituted, or a condensed ring group that may be substituted. The $R^5$ and the $R^{5'}$ each preferably represent a methyl group.

Examples of the linear or branched alkyl group having 2 to 7 carbon atoms interrupted by one or more ether bonds or thioether bonds include a methoxymethyl group, an ethoxymethyl group, a 2-ethoxyethyl group, a butoxymethyl group, a (2-butoxyethoxy)methyl group, and a 2-methylthioethyl group.

As a substituent of the phenyl group that may be substituted, there are given, for example, a linear or branched alkyl group having 1 to 4 carbon atoms, a linear or branched alkoxy group having 1 to 4 carbon atoms, a halogen atom, a cyano group, an aryl group, or a nitro group.

Examples of the phenylalkyl group having 7 to 11 carbon atoms that may be substituted include a phenylmethyl group, a 1-phenylethyl group, a 2-phenylethyl group, a 3-phenylpropyl group, a 4-phenylbutyl group, a 5-phenylpentyl group, a chlorophenylmethyl group, and a nitrophenylmethyl group.

Examples of the phenoxyalkyl group having 7 to 10 carbon atoms that may be substituted include a phenoxymethyl group, a 1-phenoxyethyl group, a 2-phenoxyethyl group, a 3-phenoxypropyl group, a 4-phenoxybutyl group, a chlorophenoxymethyl group, and a nitrophenoxymethyl group.

Examples of the heterocyclic group that may be substituted and the condensed ring group that may be substituted include the heterocyclic group that may be substituted and condensed ring group that may be substituted exemplified in section on $R^1$.

In the formula (2), $R^6$ represents a linear, branched, or cyclic alkyl group having 1 to 17 carbon atoms, a linear or branched halogenated alkyl group having 1 to 7 carbon atoms, a linear or branched alkyl group having 2 to 7 carbon atoms interrupted by one or more ether bonds or thioether bonds, a linear or branched aminoalkyl group having 2 to 4 carbon atoms that may be substituted, a phenyl group that may be substituted, a phenylalkyl group having 7 to 11 carbon atoms that may be substituted, a phenylalkyl group having 7 to 10 carbon atoms that is interrupted by one or more ether bonds or thioether bonds and may be substituted, a condensed ring group that may be substituted, or a heterocyclic group that may be substituted. The $R^6$ preferably represents a linear or branched alkyl group having 1 to 17 carbon atoms, a cyclic alkyl group having 3 to 10 carbon atoms, a linear or branched halogenated alkyl group having 1 to 7 carbon atoms, a linear or branched alkyl group having 2 to 7 carbon atoms interrupted by one or more ether bonds or thioether bonds, a linear or branched aminoalkyl group having 2 to 4 carbon atoms that may be substituted, a phenyl group that may be substituted, a phenylalkyl group having 7 to 11 carbon atoms that may be substituted, a phenylalkyl group having 7 to 10 carbon atoms that is interrupted by one or more ether bonds or thioether bonds and may be substituted, a condensed ring group that may be substituted, or a heterocyclic group that may be substituted, and more preferably represents a linear or branched alkyl group having 1 to 7 carbon atoms, a linear or branched halogenated alkyl group having 1 to 3 carbon atoms, a cyclic alkyl group having 3 to 6 carbon atoms, a linear or branched aminoalkyl group having 2 to 4 carbon atoms that may be substituted, a phenyl group substituted with any appropriate group, a condensed ring group that may be substituted, or a heterocyclic group that may be substituted.

The formula (2) specifically represents a structure containing an alkyl group represented by any one of the following formulae:

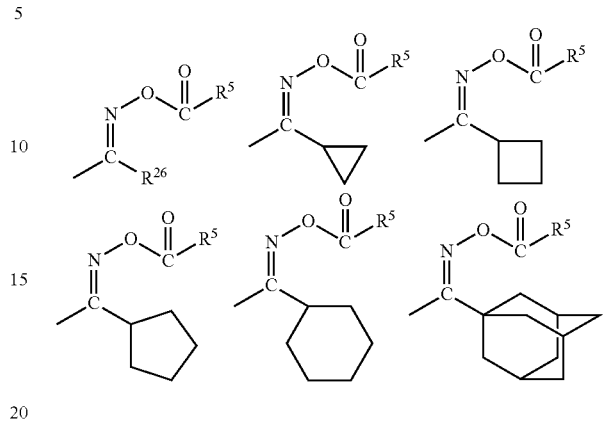

(in the formulae, $R^{26}$ represents a linear or branched alkyl group having 1 to 17 carbon atoms), a structure containing one or more ether bonds or thioether bonds represented by the following formula:

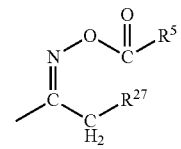

(in the formula, $R^{27}$ represents a linear or branched alkyl group having 1 to 6 carbon atoms interrupted by one or more ether bonds or thioether bonds, a linear or branched alkyloxy group having 1 to 6 carbon atoms that may be interrupted by one or more ether bonds or thioether bonds (an oxygen atom of the alkyloxy group is bonded to a carbon atom in the formula), or a linear or branched alkylthio group having 1 to 6 carbon atoms that may be interrupted by one or more ether bonds or thioether bonds (a sulfur atom of the alkylthio group is bonded to the carbon atom in the formula)), preferably a structure containing one or more ether bonds or thioether bonds represented by any one of the following formulae:

(in the formulae, $R^{28}$ represents a linear or branched alkyl group having 1 to 4 carbon atoms), a structure containing a phenyl group that may be substituted, the structure being represented by the following formula:

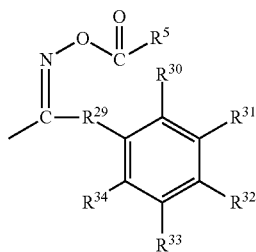

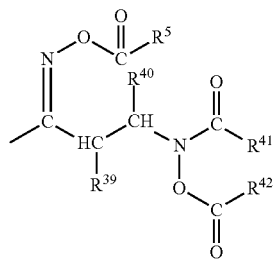

(in the formula, $R^{29}$ represents a single bond, a linear or branched alkylene group having 1 to 4 carbon atoms, a linear or branched alkylene group having 1 to 4 carbon atoms interrupted by one or more ether bonds or thioether bonds, a linear or branched alkyleneoxy group having 1 to 4 carbon atoms that may be interrupted by one or more ether bonds or thioether bonds (an oxygen atom of the alkyleneoxy group is bonded to an aromatic ring in the formula), or a linear or branched alkylenethio group having 1 to 4 carbon atoms that may be interrupted by one or more ether bonds or thioether bonds (a sulfur atom of the alkylenethio group is bonded to the aromatic ring in the formula), and $R^{30}$ to $R^{34}$ each independently represent a hydrogen atom, a linear or branched alkyl group having 1 to 7 carbon atoms, a linear or branched halogenated alkyl group having 1 to 4 carbon atoms, a halogen atom, a nitro group, a cyano group, a linear or branched alkyloxy group having 1 to 6 carbon atoms that may be interrupted by one or more ether bonds or thioether bonds (an oxygen atom of the alkyloxy group is bonded to the aromatic ring in the formula), or a linear or branched alkylthio group having 1 to 4 carbon atoms that may be interrupted by one or more ether bonds or thioether bonds (a sulfur atom of the alkylthio group is bonded to the aromatic ring in the formula), a structure containing a linear or branched aminoalkyl group having 2 to 4 carbon atoms that may be substituted, the structure being represented by the following formula:

(in the formula, $R^{39}$ and $R^{40}$ each independently represent a hydrogen atom or a methyl group, and $R^{41}$ and $R^{42}$ each represent any one of the same groups as those given for the $R^5$), a structure containing a condensed ring that may be substituted, the structure being represented by any one of the following formulae:

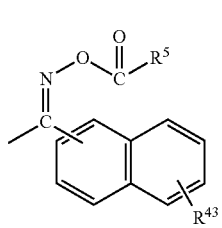

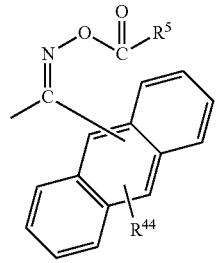

(in the formulae, $R^{43}$ represents a hydrogen atom, a linear or branched alkyl group having 1 to 4 carbon atoms, a linear or branched alkoxy group having 1 to 4 carbon atoms, or a hydroxyl group, and $R^{44}$ represents a hydrogen atom, a linear or branched alkyl group having 1 to 4 carbon atoms, a linear or branched alkoxy group having 1 to 4 carbon atoms, a hydroxyl group, a halogen atom, or a cyano group), or a structure containing a heterocycle that may be substituted, the structure being represented by any one of the following formulae.

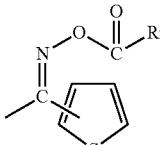 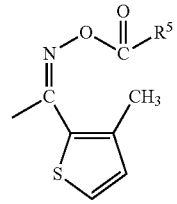 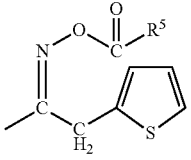

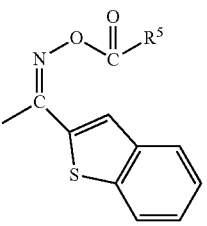 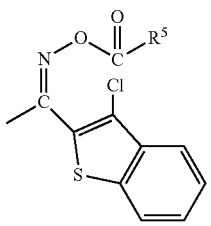

(in the formula, $R^{52}$ represents a linear or branched alkylene group having 2 to 4 carbon atoms, $R^{53}$ and $R^{54}$ each independently represent a linear or branched alkyl group having 1 to 4 carbon atoms, $R^{59}CO$, or $R^{60}COO$, and $R^{59}$ and $R^{60}$ each independently represent any one of the same groups as those given for the $R^5$), preferably a structure containing a linear or branched aminoalkyl group having 2 to 4 carbon atoms that may be substituted, the structure being represented by the following formula:

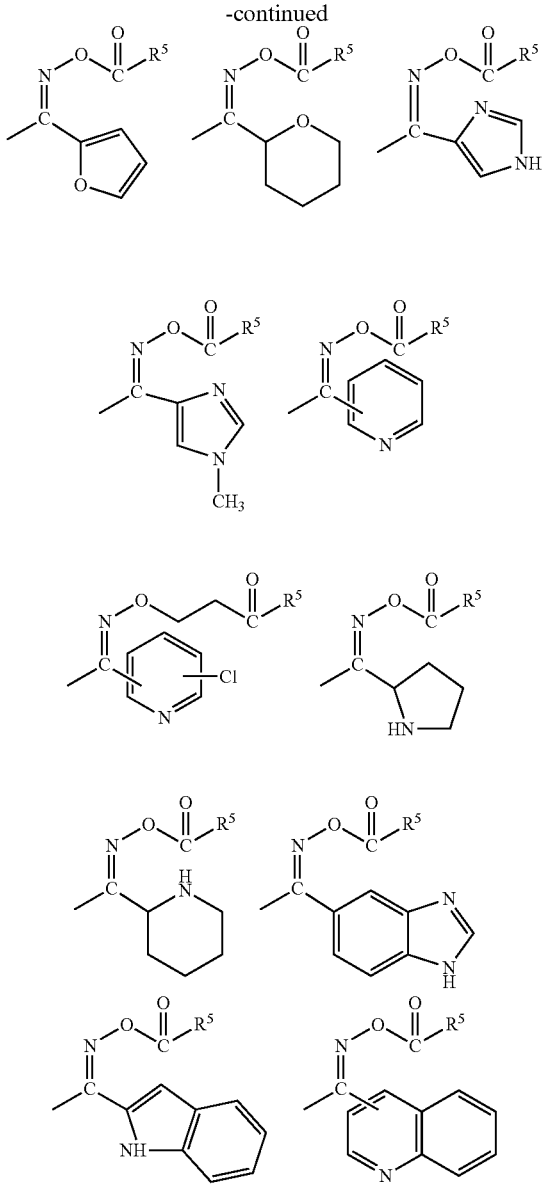

R[26] preferably represents a linear or branched alkyl group having 1 to 7 carbon atoms, and more preferably represents a linear alkyl group having 1 to 3 carbon atoms. In addition, the cyclic alkyl group having 3 to 10 carbon atoms is preferably a cyclopropyl group, a cyclobutyl group, a cyclopentyl group, a cyclohexyl group, or an adamantyl group, more preferably a cyclohexyl group.

R[27] preferably represents a linear or branched alkyl group having 1 to 6 carbon atoms interrupted by one ether bond or thioether bond, a linear or branched alkyloxy group having 1 to 6 carbon atoms that may be interrupted by one ether bond or thioether bond (an oxygen atom of the alkyloxy group is bonded to the carbon atom in the formula), or a linear or branched alkylthio group having 1 to 6 carbon atoms that may be interrupted by one ether bond or thioether bond (a sulfur atom of the alkylthio group is bonded to the carbon atom in the formula).

R[28] preferably represents a methyl group.

R[30] to R[34] preferably each independently represent a hydrogen atom, a linear or branched alkyl group having 1 to 4 carbon atoms, a linear or branched alkoxy group having 1 to 4 carbon atoms, a nitro group, a halogen atom, a linear or branched halogenated alkyl group having 1 to 4 carbon atoms, a linear or branched alkyloxy group represented by $OCH(R^{36})CH_2OR^{37}$ (an oxygen atom of the alkyloxy group is bonded to the aromatic ring in the formula, and $R^{36}$ and $R^{37}$ each independently represent a hydrogen atom, a methyl group, or an ethyl group, and preferably each independently represent a hydrogen atom or a methyl group), or a linear or branched alkylthio group represented by $SR^{38}$ (a sulfur atom of the alkylthio group is bonded to the aromatic ring in the formula, and $R^{38}$ represents a linear or branched alkyl group having 1 to 4 carbon atoms and preferably represents a methyl group), and more preferably each independently represent a hydrogen atom, a methyl group, or a methoxy group.

$R^{53}$ and $R^{54}$ preferably each independently represent $R^{59}CO$ or $R^{60}COO$ (as described above, $R^{59}$ and $R^{60}$ each independently represent any one of the same groups as those given for the $R^5$).

$R^{39}$ and $R^{40}$ preferably each independently represent a hydrogen atom or a methyl group. $R^{41}$ and $R^{42}$ preferably each represent a methyl group.

$R^{43}$ preferably represents a hydrogen atom, a methyl group, an ethyl group, a methoxy group, an ethoxy group, or a hydroxyl group. $R^{44}$ preferably represents a hydrogen atom, a methyl group, a cyano group, or a halogen atom.

In the formula (3), $R^7$ represents a linear, branched, or cyclic alkyl group having 1 to 16 carbon atoms, a linear or branched halogenated alkyl group having 1 to 6 carbon atoms, a phenyl group that may be substituted, a phenylalkyl group having 7 to 10 carbon atoms that may be substituted, a phenylalkyl group having 7 to 9 carbon atoms that is interrupted by one or more ether bonds or thioether bonds and may be substituted, a condensed ring group that may be substituted, or a heterocyclic group that may be substituted. The $R^7$ preferably represents a linear, branched, or cyclic alkyl group having 1 to 6 carbon atoms, a linear or branched halogenated alkyl group having 1 to 4 carbon atoms, a phenyl group that may be substituted, a phenylalkyl group having 7 to 10 carbon atoms that may be substituted, a phenylalkyl group having 7 to 9 carbon atoms that is interrupted by one or more ether bonds or thioether bonds and may be substituted, a condensed ring group that may be substituted, or a heterocyclic group that may be substituted.

The formula (3) specifically represents a structure containing an alkyl group represented by the following formula:

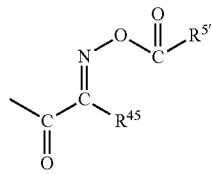

(in the formula, $R^{45}$ represents a linear, branched, or cyclic alkyl group having 1 to 16 carbon atoms, or a linear or branched halogenated alkyl group having 1 to 6 carbon atoms), a structure containing a phenyl group that may be substituted, the structure being represented by the following formula:

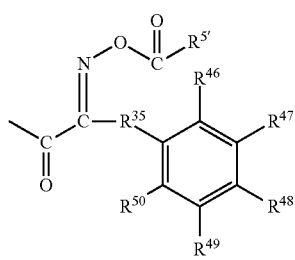

(in the formula, $R^{35}$ represents a single bond, a linear or branched alkylene group having 1 to 4 carbon atoms, a linear or branched alkylene group having 1 to 4 carbon atoms interrupted by one or more ether bonds or thioether bonds, a linear or branched alkyleneoxy group having 1 to 4 carbon atoms that may be interrupted by one or more ether bonds or thioether bonds (an oxygen atom of the alkyleneoxy group is bonded to an aromatic ring in the formula), or a linear or branched alkylenethio group having 1 to 4 carbon atoms that may be interrupted by one or more ether bonds or thioether bonds (a sulfur atom of the alkylenethio group is bonded to the aromatic ring in the formula), and $R^{46}$ to $R^{50}$ each independently represent a hydrogen atom, a linear or branched alkyl group having 1 to 4 carbon atoms, a linear or branched alkyloxy group having 1 to 4 carbon atoms, a linear or branched alkylthio group having 1 to 4 carbon atoms, a linear or branched halogenated alkyl group having 1 to 4 carbon atoms, a halogen atom, a nitro group, an aryl group, a benzyl group, or a benzyloxy group), a structure containing a condensed ring group that may be substituted, the structure being represented by the following formula:

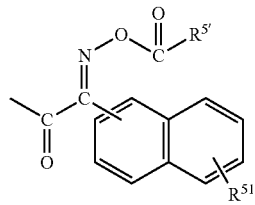

(in the formula, $R^{51}$ represents a hydrogen atom, a linear or branched alkyl group having 1 to 4 carbon atoms, a linear or branched alkoxy group having 1 to 4 carbon atoms, or a hydroxyl group), or a structure containing a heterocyclic group that may be substituted, the structure being represented by any one of the following formulae.

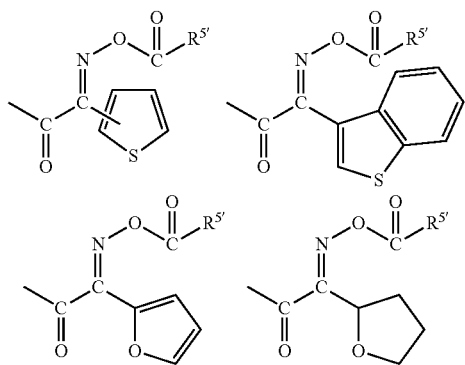

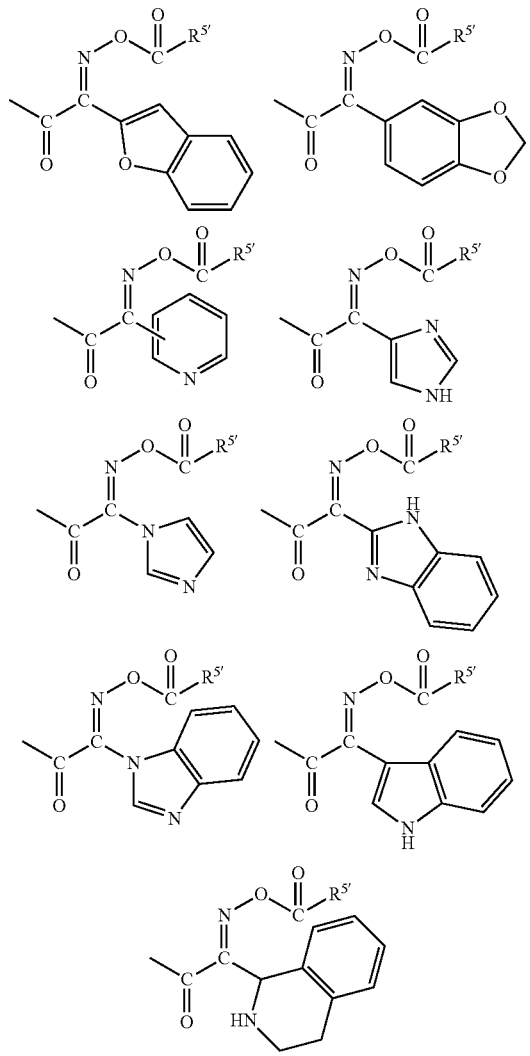

$R^{45}$ preferably represents a linear, branched, or cyclic alkyl group having 1 to 6 carbon atoms, or a linear or branched halogenated alkyl group having 1 to 4 carbon atoms, and more preferably represents a linear alkyl group having 1 to 3 carbon atoms, or a linear halogenated alkyl group having 1 to 2 carbon atoms.

$R^{46}$ to $R^{50}$ preferably each independently represent a hydrogen atom, a methyl group, or a methoxy group.

$R^{51}$ preferably represents a hydrogen atom, a methyl group, an ethyl group, a methoxy group, an ethoxy group, or a hydroxyl group.

In the general formula (1), m represents the number of phenylene groups. The m represents 0 or 1. In addition, in the general formula (1), n represents the number of carbonyl groups. The n represents 0 or 1. It is preferred that in the general formula (1), the m and the n each represent 0, or the m represent 0 and the n represent 1.

Specific examples of the fluorene-based compound represented by the general formula (1) include the following compounds. It should be noted that: in the following list of the compounds, the character "化合物" represents "Compound".

化合物 1
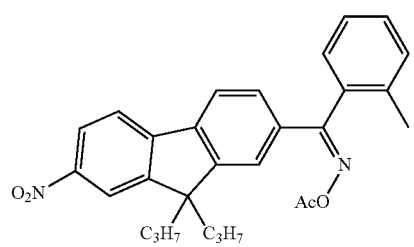
化合物 2
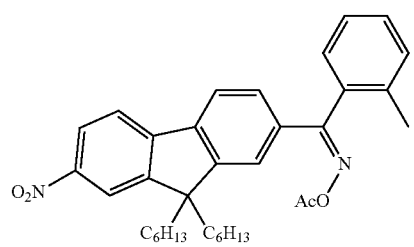
化合物 3
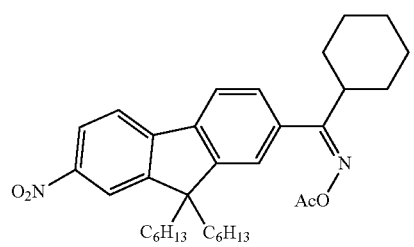
化合物 4
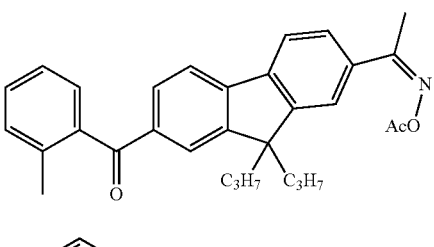
化合物 5
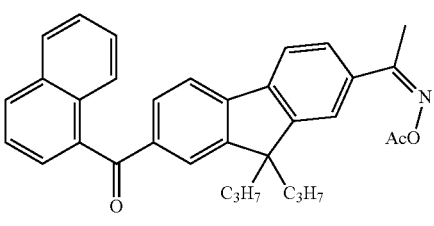
化合物 6
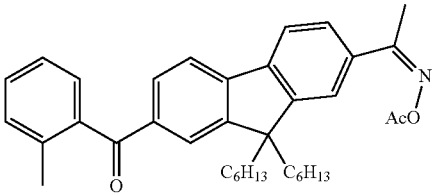
化合物 7
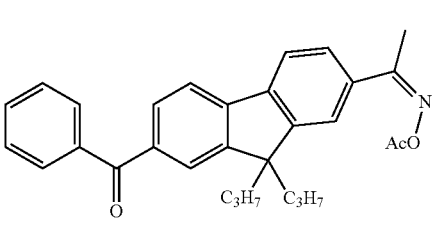
-continued
化合物 8
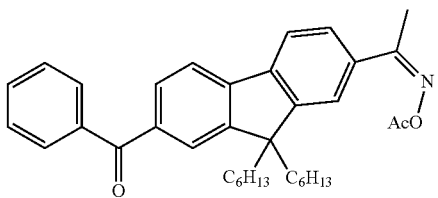
化合物 9
化合物 10
化合物 11
化合物 12
化合物 13
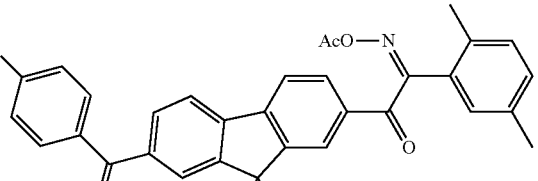

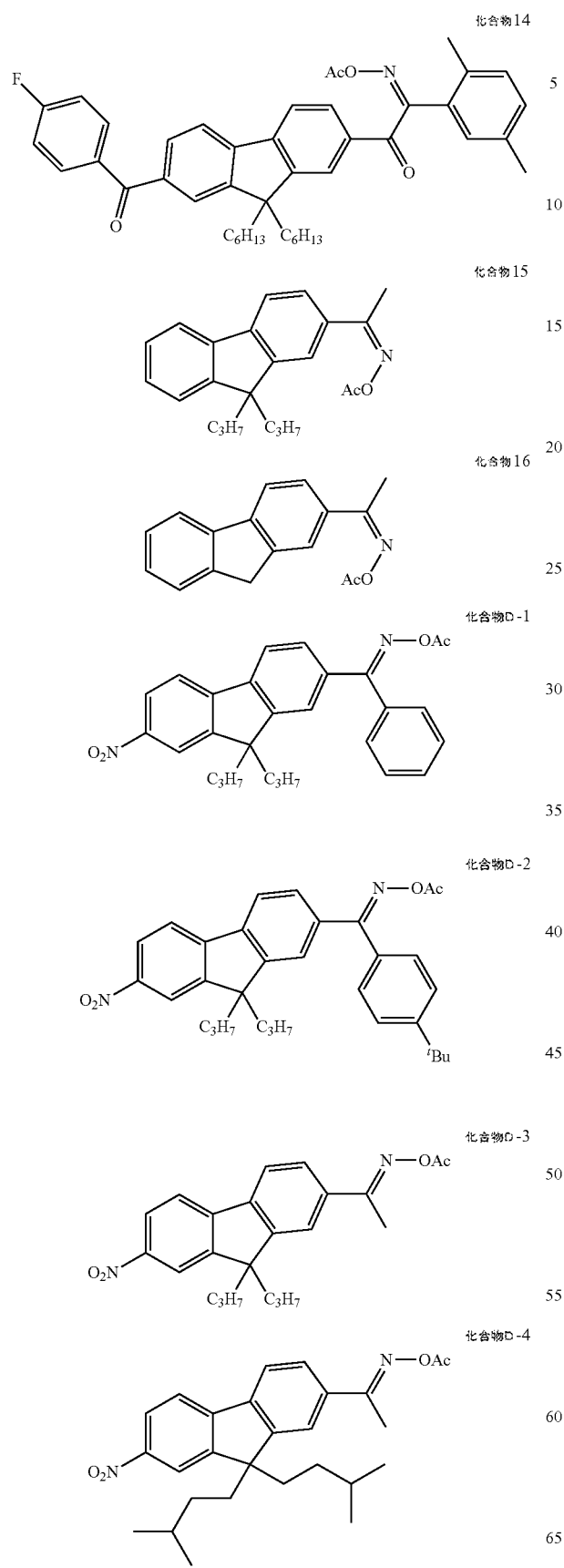
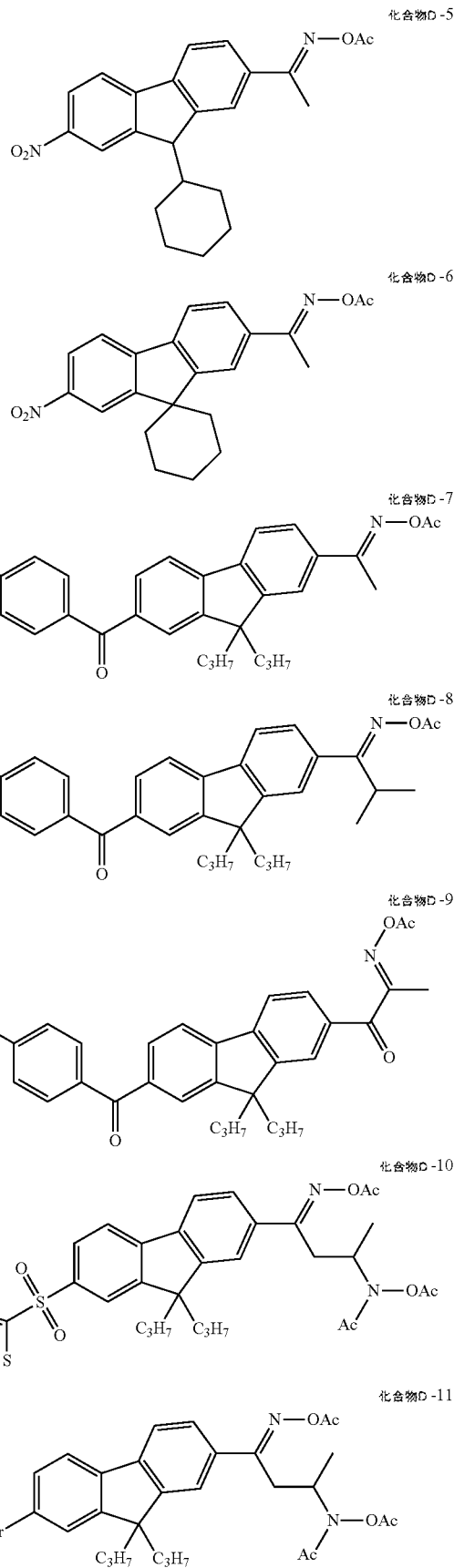

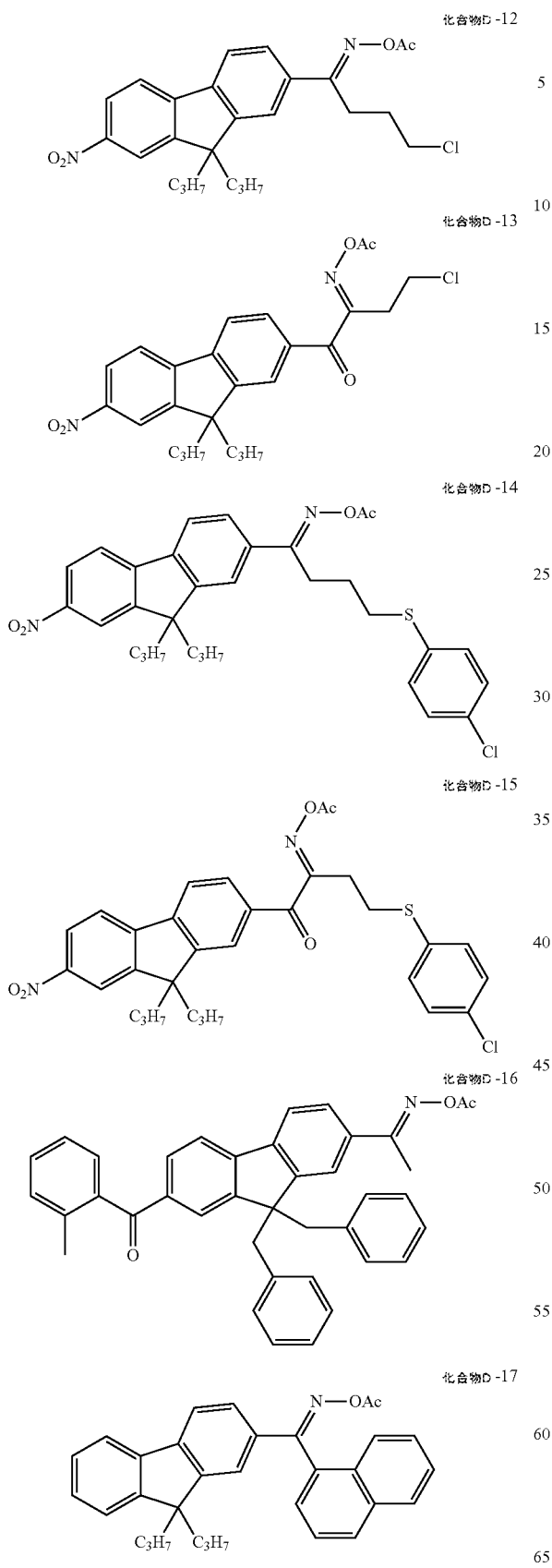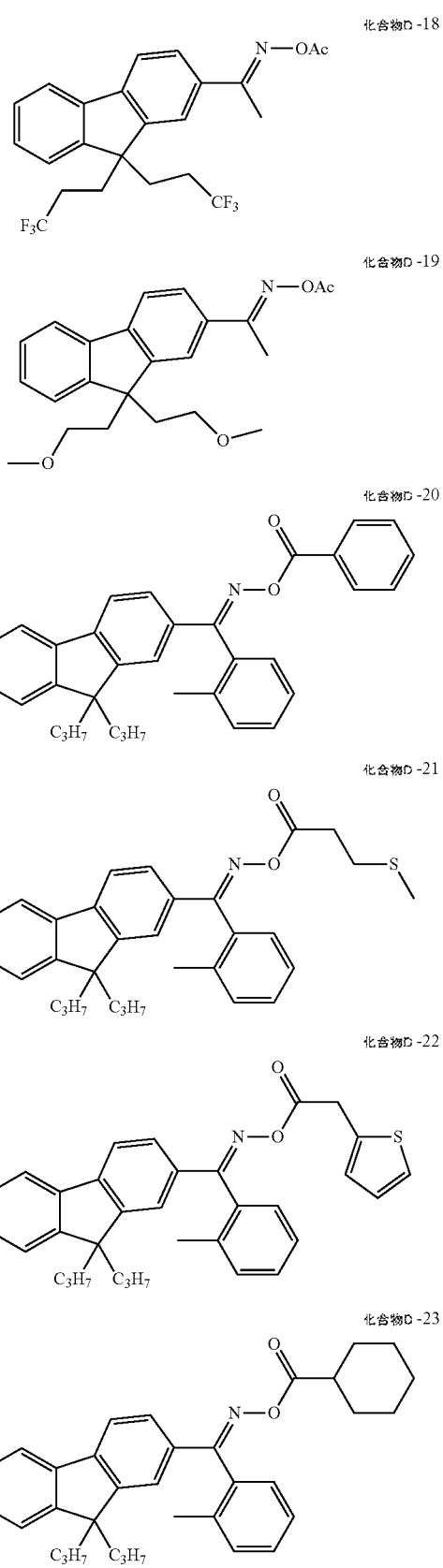

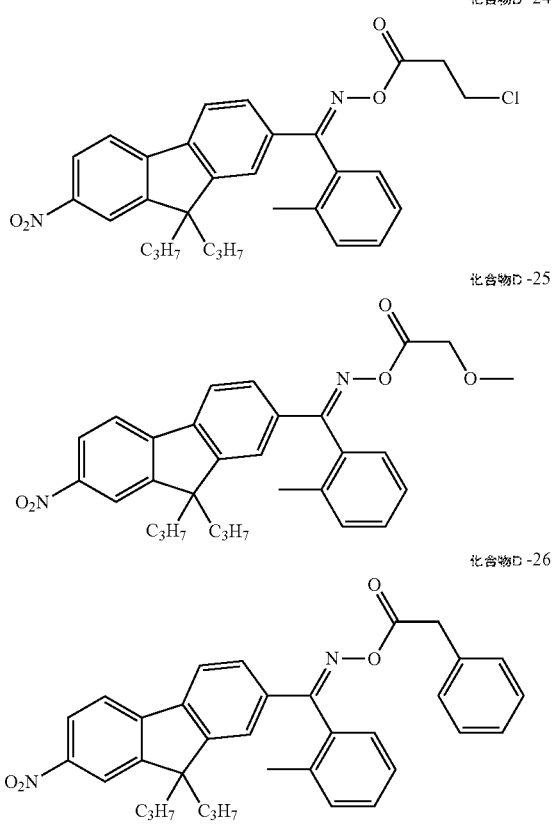

A-2. Synthesis of Fluorene-Based Compound

The fluorene-based compound of the present invention can be synthesized by, for example, the following reaction scheme.

First, a fluorene-based compound having desired $R^2$ and desired $R^3$ can be obtained by, for example, causing fluorene, halides each containing $R^2$ or $R^3$ ($X^1$—$R^2$ and $X^2$—$R^3$ where $X^1$ and $X^2$ each independently represent bromine, chlorine, or iodine, and $R^2$ and $R^3$ are as described above), and any appropriate base to react with one another (reaction I).

[Reaction I]

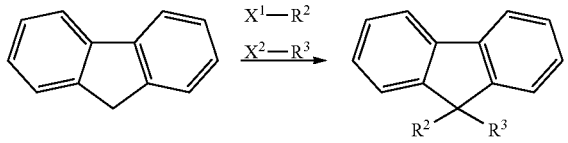

The halogen atom represented by the $X^2$ or $X^2$ is preferably bromine or iodine.

Any appropriate base can be used as the base, and examples thereof include an inorganic base and an organic base. Specific examples thereof include lithium hydroxide, sodium hydroxide, calcium hydroxide, potassium hydroxide, magnesium hydroxide, sodium hydrogen carbonate, potassium hydrogen carbonate, sodium carbonate, potassium carbonate, triethylamine, pyridine, piperidine, diazabicycloundecene, butyllithium, potassium tert-butoxide, sodium tert-butoxide, sodium methoxide, and sodium ethoxide. Of those, butyllithium, potassium tert-butoxide, sodium tert-butoxide, sodium methoxide, and sodium ethoxide are preferred as the base.

Any appropriate halide can be used as each of the $X^1$—$R^2$ and the $X^2$—$R^3$. Examples of the halide include: an alkyl halide having a linear, branched, or cyclic alkyl group having 1 to 22 carbon atoms; a halide having a linear or branched halogenated alkyl group having 1 to 10 carbon atoms substituted with a halogen atom; a halide having a linear or branched alkyl group having 2 to 15 carbon atoms interrupted by one or more ether bonds or thioether bonds; a benzene halide substituted with an alkyl group having 1 to 11 carbon atoms; a benzene halide having an alkyl group having 1 to 5 carbon atoms interrupted by one or more ether bonds or thioether bonds; a benzene halide substituted with a halogen atom; a benzene halide substituted with an amino group; a phenylalkyl halide having 7 to 11 carbon atoms; and an alkyl dihalide having a linear or branched alkyl group having 2 to 12 carbon atoms.

More specifically, examples of the halide to be used in the case where a linear, branched, or cyclic alkyl group having 1 to 22 carbon atoms is introduced as each of $R^2$ and $R^3$ include methyl iodide, ethyl bromide, propyl bromide, cyclopropyl bromide, butyl bromide, 2-methylpropyl bromide, tert-butyl bromide, cyclobutyl bromide, pentyl bromide, 1-methylbutyl bromide, 2-methylbutyl bromide, 3-methylbutyl bromide, cyclobutylmethyl bromide, cyclopentyl bromide, hexyl bromide, cyclohexyl bromide, 4-methylpentyl bromide, 1-ethylbutyl bromide, 2-ethylbutyl bromide, heptyl bromide, cycloheptyl bromide, 1-ethylpentyl bromide, cyclohexylmethyl bromide, octyl bromide, 1-methylheptyl bromide, 2-ethylhexyl bromide, nonyl bromide, decyl bromide, undecyl bromide, dodecyl bromide, tridecyl bromide, tetradecyl bromide, pentadecyl bromide, hexadecyl bromide, heptadecyl bromide, octadecyl bromide, eicosyl bromide, and docosyl bromide.

In addition, examples of the halide to be used in the case where a linear or branched halogenated alkyl group having 1 to 10 carbon atoms is introduced as each of $R^2$ and $R^3$ include 2-chloroethyl bromide, 3-chloro-2-methylpropyl bromide, 3-chloropropyl bromide, 4-chlorobutyl bromide, 5-chloropentyl bromide, 6-chlorohexyl bromide, 7-chloropentyl bromide, 3,4-dichlorobutyl bromide, 2,2,2-trifluoroethyl bromide, 3,3,3-trifluoropropyl bromide, 4,4,4-trifluorobutyl bromide, heptafluoropropyl bromide, nonafluorobutyl bromide, tridecafluorohexyl bromide, pentadecafluoroheptyl bromide, heptadecafluorooctyl bromide, nonadecafluorononyl bromide, perfluorodecyl bromide, 2-chloroethyl iodide, 3-chloropropyl iodide, 4-chlorobutyl iodide, 5-chloropentyl iodide, 6-chlorohexyl iodide, 2,2,2-trifluoroethyl iodide, 3,3,3-trifluoropropyl iodide, 4,4,4-trifluorobutyl iodide, heptafluoropropyl iodide, nonafluorobutyl iodide, tridecafluorohexyl iodide, heptadecafluorooctyl iodide, and perfluorodecyl iodide.

In addition, examples of the halide to be used in the case where a linear or branched alkyl group having 2 to 15 carbon atoms interrupted by one or more ether bonds or thioether bonds is introduced as each of $R^2$ and $R^3$ include bromoethyl methyl ether, bromoethyl ethyl ether, bromomethoxypropane, 3-(2-methoxyethoxy)propyl bromide, 2-[2-(2-methoxyethoxy)ethoxy]ethyl bromide, 2-[2-[2-(2-methoxyethoxy)ethoxy]ethoxy]ethyl bromide, 2-chloroethyl methyl sulfide, 2-chloroethyl ethyl sulfide, and 3-chloropropyl dodecyl sulfide.

In addition, examples of the halide to be used in the case where a phenyl group that may be substituted is introduced as each of $R^2$ and $R^3$ include bromobenzene, iodotoluene, bromofluorobenzene, bromothioanisole, bromoanisole, bromobenzonitrile, bromoethylbenzene, bromo-tert-butylbenzene, bromocumene, bromo-N,N-dimethylaniline, bromotrimethylsilylbenzene, bromoethynylbenzene, bromobenzyl cyanide, bromonitrobenzene, bromophenylpiperidine, bromobiphenyl, bromomethanesulfonylbenzene, benzyloxybromobenzene, and (trifluoromethyl)iodobenzene.

In addition, examples of the halide to be used in the case where a phenylalkyl group having 7 to 11 carbon atoms is introduced as each of $R^2$ and $R^3$ include benzyl bromide, (bromoethyl)benzene, phenylpropyl bromide, phenylbutyl bromide, phenylpentyl bromide, (trifluoromethyl)benzyl bromide, and (trifluoromethoxy)benzyl bromide.

In addition, examples of the halide to be used in the case where $R^2$ and $R^3$ form a ring together include dibromoethane, dibromopentane, dibromohexane, and dibromododecane.

When $R^2$ and $R^3$ each represent a linear or branched alkyl group having 2 to 15 carbon atoms interrupted by one or more ether bonds, the fluorene-based compound having desired $R^2$ and desired $R^3$ can also be obtained by performing, for example, a reaction involving introducing an ester group, then a reaction involving reducing the introduced ester group to provide a hydroxyl group, and then a reaction involving alkylating the hydroxyl group. The reactions can be represented by the following reaction scheme (reaction I').

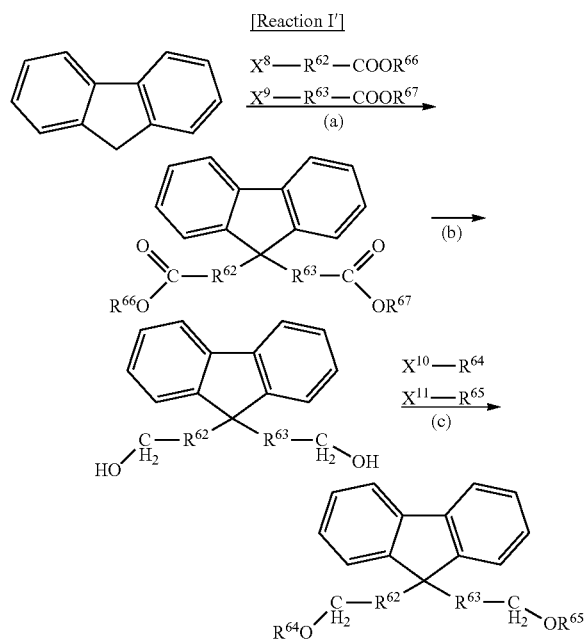

The ester group-introducing reaction can be performed by, for example, causing fluorene and a halogenated alkyl carboxylic acid alkyl ester to react with each other (reaction I' (a)). The reaction can be performed in the presence of any appropriate base.

Any appropriate compound can be used as the halogenated alkyl carboxylic acid alkyl ester. When $R^2$ represents a group represented by $R^{62}$—$CH_2$—O—$R^{64}$ (where $R^{62}$ represents a group to be bonded to a fluorene ring and represents a linear or branched alkyl group having 1 to 7 (preferably 1 to 4) carbon atoms that may be interrupted by one or more ether bonds, and $R^{64}$ represents a linear or branched alkyl group having 1 to 13 (preferably 1 to 4) carbon atoms that may be interrupted by one or more ether bonds), and $R^3$ represents a group represented by $R^{63}$—$CH_2$—O—$R^{65}$ (where $R^{63}$ represents a group to be bonded to the fluorene ring and represents a linear or branched alkyl group having 1 to 7 (preferably 1 to 4) carbon atoms that may be interrupted by one or more ether bonds, and $R^{65}$ represents a linear or branched alkyl group having 1 to 13 (preferably 1 to 4) carbon atoms that may be interrupted by one or more ether bonds), the halogenated alkyl carboxylic acid alkyl ester preferably contains $R^{62}$ or $R^{63}$. The halogenated alkyl carboxylic acid alkyl ester containing $R^{62}$ or $R^{63}$ is, for example, a halogenated alkyl carboxylic acid alkyl ester represented by $X^8$—$R^{62}$—$COOR^{66}$ or $X^9$—$R^{63}$—$COOR^{67}$ (where $X^8$ and $X^9$ each independently represent a halogen atom, preferably bromine, chlorine, or iodine, $R^{66}$ and $R^{67}$ each independently represent a linear or branched alkyl group having 1 to 7 carbon atoms, and $R^{62}$ and $R^{63}$ are as described above).

Examples of the base include an inorganic base and an organic base. The base is specifically, for example, the base used in the reaction I. The base is preferably butyllithium, potassium tert-butoxide, sodium tert-butoxide, sodium methoxide, or sodium ethoxide.

The reaction involving reducing the introduced ester group to provide a hydroxyl group can be performed by, for example, causing a reducing agent to act on a compound obtained by the reaction I' (a) (reaction I' (b)).

Any appropriate reducing agent can be used as the reducing agent. Examples of the reducing agent include lithium aluminum hydride, sodium borohydride, and a borane.

The reaction involving alkylating the hydroxyl group can be performed by, for example, causing an alkylating agent to act on a compound obtained by the reaction I'(b) (reaction I'(c)). The reaction can be performed in the presence of any appropriate base.

Any appropriate alkylating agent can be used as the alkylating agent. When $R^2$ represents a group represented by $R^{62}$—$CH_2$—O—$R^{64}$ and $R^3$ represents a group represented by $R^{63}$—$CH_2$—O—$R^{65}$, the alkylating agent is, for example, an alkyl halide represented by $X^{10}$—$R^{64}$ or $X^{11}$—$R^{65}$ (where $X^{10}$ and $X^{11}$ each independently represent a halogen atom, preferably bromine, chlorine, or iodine, and $R^{64}$ and $R^{65}$ are as described above).

Examples of the base include an inorganic base and an organic base. Specific examples of the base include sodium hydride, a Grignard reagent such as an alkylmagnesium bromide, and the base used in the reaction I. The base is preferably sodium hydride.

It should be noted that when $R^2$ and $R^3$ represent hydrogen atoms, the reactions I and I' are omitted.

Next, the fluorene-based compound having desired $R^2$ and desired $R^3$, and a carboxylic halide containing the $R^6$ when the $R^4$ represents a group represented by the formula (2), or a carboxylic halide containing the $R^7$ when the $R^4$ represents a group represented by the formula (3), are caused to react with each other in the presence of any appropriate Lewis acid (reaction II).

[Reaction II]

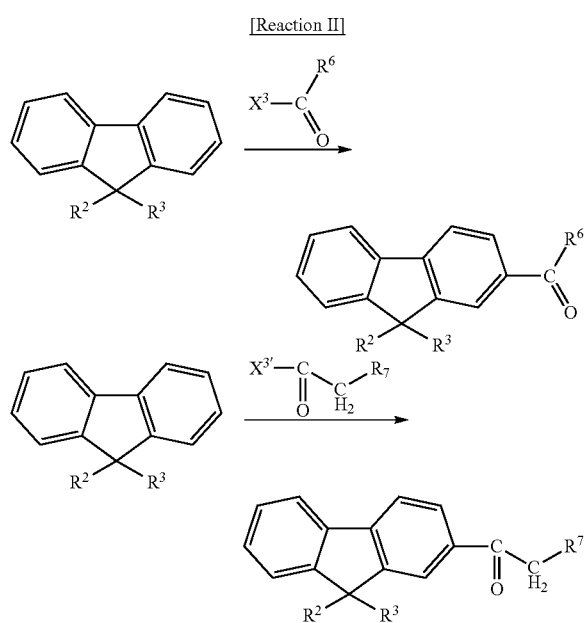

Halogen atoms ($X^3$ and $X^{3'}$) in the carboxylic halide containing the $R^6$ and the carboxylic halide containing the $R^7$ are each preferably chlorine, bromine, or iodine.

Any appropriate Lewis acid can be used as the Lewis acid. Examples of the Lewis acid include aluminum chloride, iron chloride, and titanium tetrachloride. The Lewis acid is preferably aluminum chloride.

Any appropriate carboxylic halide can be used as the carboxylic halide containing the $R^6$. Examples thereof include: a linear, branched, or cyclic alkyl carboxylic halide having 1 to 17 carbon atoms; a linear or branched halogenated alkyl carboxylic halide having 1 to 7 carbon atoms; a linear or branched alkyl carboxylic halide having 2 to 7 carbon atoms interrupted by one or more ether bonds or thioether bonds; a phenyl carboxylic halide that may be substituted; a phenylalkyl carboxylic halide having 7 to 11 carbon atoms that may be substituted; a phenoxyalkyl carboxylic halide having 7 to 10 carbon atoms that may be substituted; a condensed ring carboxylic halide that may be substituted; and a heterocyclic carboxylic halide that may be substituted.

It should be noted that when the $R^6$ represents an aminoalkyl group having 2 to 4 carbon atoms that may be substituted, the group is derived by: causing the fluorene-based compound having desired $R^2$ and desired $R^3$, and an alkyl carboxylic halide having 2 to 4 carbon atoms and having an unsaturated bond to react with each other; and then performing an oximation reaction and an acylation reaction. Alternatively, the group is derived by: causing the fluorene-based compound having desired $R^2$ and desired $R^3$, and a halogenated alkyl carboxylic halide having 2 to 4 carbon atoms to react with each other; and then performing an amination reaction. The halogenated alkyl carboxylic halide is, for example, 4-chlorobutyryl chloride.

Any appropriate carboxylic halide can be used as the carboxylic halide containing the $R^7$. Examples thereof include: a linear, branched, or cyclic alkyl carboxylic halide having 2 to 17 carbon atoms; a linear or branched halogenated alkyl carboxylic halide having 2 to 7 carbon atoms; a phenylalkyl carboxylic halide having 7 to 11 carbon atoms that may be substituted; a phenoxyalkyl carboxylic halide having 7 to 10 carbon atoms that may be substituted; a condensed ring acetyl halide that may be substituted; and a heterocyclic acetyl halide that may be substituted.

When the $R^4$ represents a group represented by the formula (2), and the $R^6$ represents a phenylalkyl group having 7 to 10 carbon atoms that is interrupted by one or more ether bonds or thioether bonds and may be substituted, or when the $R^4$ represents a group represented by the formula (3), and the $R^7$ represents a phenylalkyl group having 7 to 9 carbon atoms that is interrupted by one or more ether bonds or thioether bonds and may be substituted, the below-indicated compound obtained by the reaction II may be further subjected to the following reaction II'.

[Reaction II']

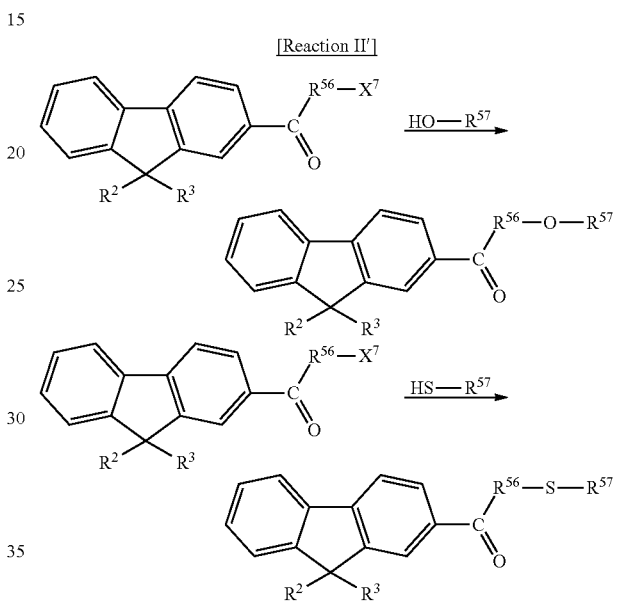

In the reaction II', $R^{56}$ represents a linear or branched alkylene group, or an alkylene group interrupted by one or more ether bonds or thioether bonds, $R^{57}$ represents a phenyl group that may be substituted or a phenylalkyl group that may be substituted, —$R^{56}$—O—$R^{57}$ and —$R^{56}$—S—$R^{57}$ each correspond to —$R^6$ or —$CH_2$—$R^7$, and $X^7$ represents a halogen atom.

The halogen atom ($X^7$) is preferably chlorine, bromine, or iodine.

The reaction II' may be performed in the presence of a halogen exchanger. Any appropriate halogen exchanger can be used as the halogen exchanger. Examples of the halogen exchanger include alkali metal halides (such as sodium iodide, potassium iodide, sodium bromide, and potassium bromide), and quaternary ammonium salts (such as tetrabutylammonium bromide and tetrabutylammonium iodide).

The reaction II' may be performed in the presence of a base. Any appropriate base can be used as the base. Examples of the base include an inorganic base and an organic base. Examples of the base include alkali metal hydroxides (such as sodium hydroxide and potassium hydroxide), sodium carbonate, potassium carbonate, potassium tert-butoxide, sodium hydride, and diazabicycloundecene.

Next, a fluorene-based compound having desired $R^1$ is obtained by causing the fluorene-based compound obtained by the reaction II and/or the reaction II', and a compound capable of providing the desired $R^1$ to react with each other (reaction III).

When the m represents 0 and the n represents 0, i.e., when such a compound that the $R^1$ is directly bonded to a fluorene skeleton is synthesized, and the $R^1$ represents a group except a sulfonyl group substituted with an alkyl group having 1 to 8 carbon atoms that may be substituted with a halogen atom and a phenylsulfonyl group that may be substituted, the fluorene-based compound having desired $R^1$ is obtained by, for example, causing the fluorene-based compound obtained by the reaction II and/or the reaction II', and the compound capable of providing the desired $R^1$ to react with each other (reaction III-i).

When the m represents 0 and the n represents 0, and the $R^1$ represents a sulfonyl group substituted with an alkyl group having 1 to 8 carbon atoms that may be substituted with a halogen atom, a phenylsulfonyl group that may be substituted, a condensed ring sulfonyl group that may be substituted, or a heterocyclic sulfonyl group that may be substituted, the fluorene-based compound having desired $R^1$ is obtained by, for example, causing the fluorene-based compound obtained by the reaction II and/or the reaction II', and a sulfonic halide capable of providing the desired $R^1$ to react with each other (reaction III-ii). Any one of the same halogen atoms as those of the $X^3$ and the $X^{3'}$ can be suitably used as a halogen $X^4$ in the sulfonic halide capable of providing the desired $R^1$.

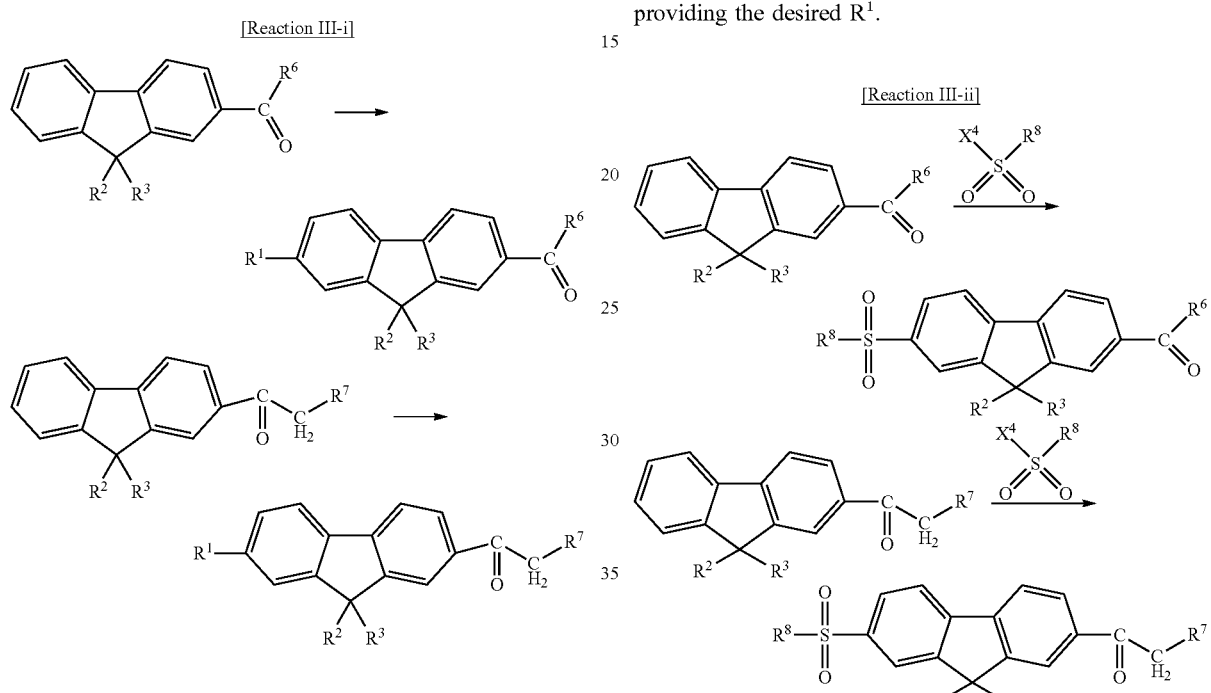

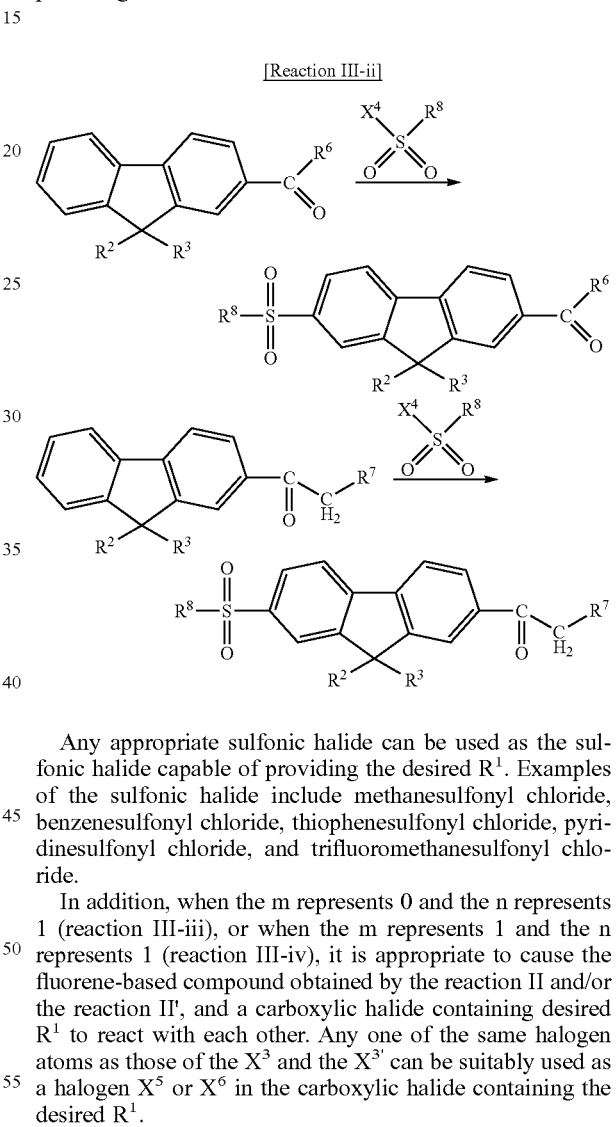

For example, when a fluorene-based compound having a nitro group as $R^1$ is synthesized, the fluorene-based compound having a nitro group as $R^1$ is obtained by nitrating the fluorene-based compound having desired $R^2$, desired $R^3$, and desired $R^4$ according to an ordinary method.

In addition, for example, when a fluorene-based compound having a halogen atom as $R^1$ is synthesized, the fluorene-based compound having a halogen atom as $R^1$ is obtained by nitrating the fluorene-based compound obtained by the reaction II and/or the reaction II' according to an ordinary method, then reducing the resultant, and subjecting the reduced product to the Sandmeyer reaction.

In addition, for example, when a fluorene-based compound having, as $R^1$, an alkylsulfonyloxy group or a phenylsulfonyloxy group that may be substituted is synthesized, the fluorene-based compound having an alkylsulfonyloxy group or a phenylsulfonyloxy group that may be substituted is obtained by nitrating the fluorene-based compound obtained by the reaction II and/or the reaction II' according to an ordinary method, then reducing the resultant, and subjecting the reduced product to the Sandmeyer reaction to introduce a hydroxyl group, followed by a reaction with any appropriate compound. Examples of the compound to be caused to react with the fluorene-based compound after the introduction of the hydroxyl group include methanesulfonyl chloride, ethanesulfonyl chloride, benzenesulfonyl chloride, p-toluenesulfonyl chloride, and trifluoromethanesulfonyl chloride.

Any appropriate sulfonic halide can be used as the sulfonic halide capable of providing the desired $R^1$. Examples of the sulfonic halide include methanesulfonyl chloride, benzenesulfonyl chloride, thiophenesulfonyl chloride, pyridinesulfonyl chloride, and trifluoromethanesulfonyl chloride.

In addition, when the m represents 0 and the n represents 1 (reaction III-iii), or when the m represents 1 and the n represents 1 (reaction III-iv), it is appropriate to cause the fluorene-based compound obtained by the reaction II and/or the reaction II', and a carboxylic halide containing desired $R^1$ to react with each other. Any one of the same halogen atoms as those of the $X^3$ and the $X^{3'}$ can be suitably used as a halogen $X^5$ or $X^6$ in the carboxylic halide containing the desired $R^1$.

[Reaction III-iii]

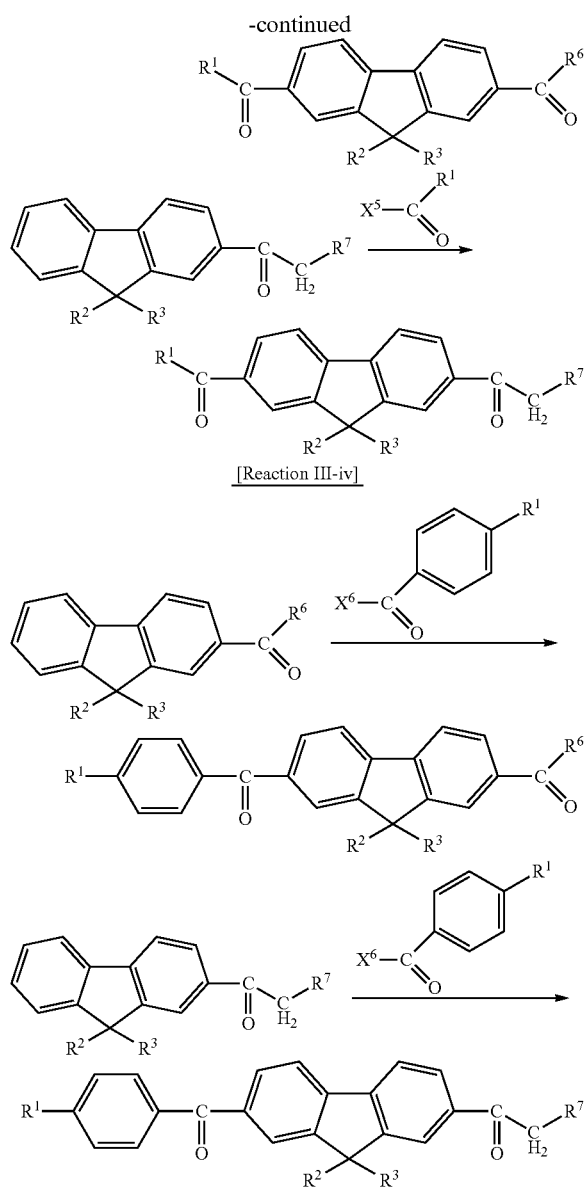

[Reaction III-iv]

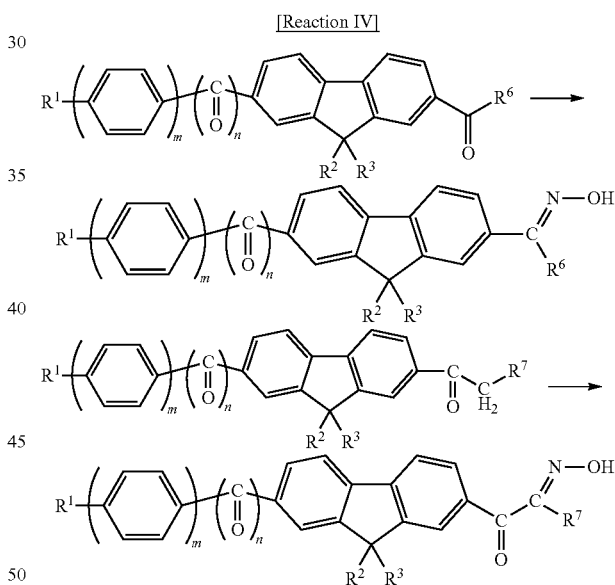

Any appropriate carboxylic halide can be used as the carboxylic halide containing the $R^1$. Examples of the carboxylic halide to be used in the reaction III-iii include benzoyl chloride, toluoyl chloride, methoxybenzoyl chloride, thenoyl chloride, and naphthoyl chloride.

In addition, when a fluorene-based compound having, as $R^1$, an alkylsulfonyloxy group that may be substituted with a halogen atom or a phenylsulfonyloxy group that may be substituted is synthesized, a carboxylic halide having, at its para position, a hydroxyl group protected with any appro-priate protective group is preferably used in the reaction III-iv. Examples of the protective group include an acetyl group and a pivaloyl group.

In addition, when the carboxylic halide having a protected hydroxyl group is used, the fluorene-based compound having an alkylsulfonyloxy group or a phenylsulfonyloxy group can be obtained by deprotecting the group with a base such as sodium hydroxide, potassium carbonate, or triethylamine, and causing the resultant to react with a desired sulfonic halide. Examples of the sulfonic halide for introducing the alkylsulfonyloxy group include methanesulfonyl chloride, isopropylsulfonyl chloride, 1-octanesulfonyl chloride, and 2-chloroethanesulfonyl chloride. In addition, examples of the sulfonic halide for introducing the phenylsulfonyloxy group include benzenesulfonyl chloride, p-toluenesulfonyl chloride, 4-methoxybenzenesulfonyl chloride, 4-isopropoxyphenylsulfonyl chloride, 2,4-dichlorobenzenesulfonyl chloride, 4-cyanobenzenesulfonyl chloride, and 4-nitrobenzenesulfonyl chloride.

Next, a carbonyl group adjacent to $R^6$ is transformed into an oxime group, or an oxime group is introduced to carbon adjacent to $R^7$, by causing the fluorene-based compound substituted with desired $R^1$ and hydroxylamine hydrochloride, a nitrite, nitrosyl chloride, or the like to react with each other (reaction IV).

[Reaction IV]

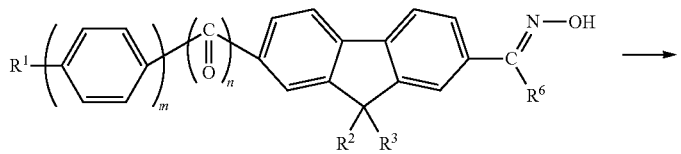

Next, a hydroxyl group at the terminal of the oxime group can be substituted with a desired $R^5$ or $R^{5'}$ group by causing a fluorene-based compound obtained by the reaction IV and a compound capable of providing the desired $R^5$ or $R^{5'}$ group to react with each other (reaction V).

[Reaction V]

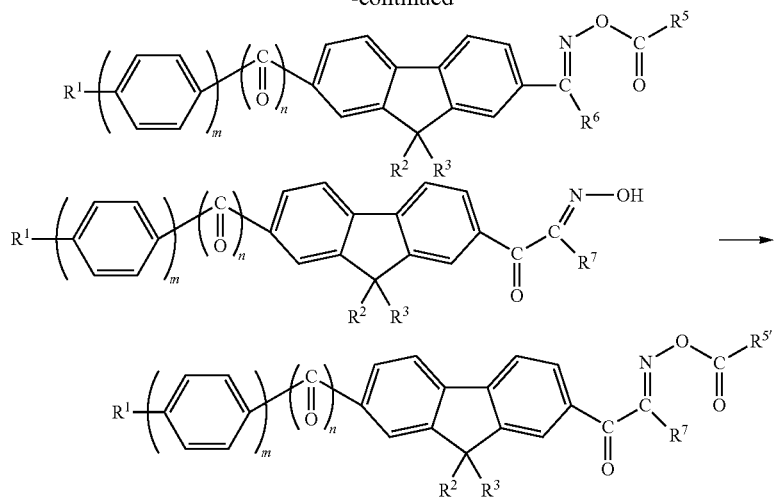

Any appropriate compound can be used as the compound capable of providing the desired $R^5$ or $R^{5'}$. As a compound capable of providing a linear, branched, or cyclic alkyl group having 1 to 17 carbon atoms, there are given, for example: acid anhydrides such as acetic anhydride, propionic anhydride, decanoic anhydride, stearic anhydride, isobutyric anhydride, and pivalic anhydride; and acid halides such as cyclohexanecarbonyl chloride, 2-propylvaleryl chloride, and 3,5,5-trimethylhexanoyl chloride. In addition, as a compound capable of providing a linear or branched halogenated alkyl group having 2 to 5 carbon atoms, there are given, for example, acid halides such as 3-chloropropionyl chloride, 5-chlorovaleryl chloride, 3-chloropivaloyl chloride, and 6-bromohexanoyl chloride. In addition, as a compound capable of providing a linear or branched alkyl group having 2 to 7 carbon atoms interrupted by one or more ether bonds or thioether bonds, there are given, for example, acid halides such as methoxyacetyl chloride, ethoxyacetyl chloride, butoxyacetyl chloride, 3-(methylthio)propionyl chloride, and (2-butoxyethoxy)acetyl chloride. In addition, as a compound capable of providing a phenyl group that may be substituted, there are given, for example: acid anhydrides such as 4-methoxyphenylacetic anhydride; and acid halides such as benzoyl chloride, toluoyl chloride, 3,5-dimethylbenzoyl chloride, 4-methoxybenzoyl chloride, 4-cyanobenzoyl chloride, 4-nitrobenzoyl chloride, 4-phenylbenzoyl chloride, and chlorobenzoyl chloride. In addition, as a compound capable of providing a phenylalkyl group having 7 to 11 carbon atoms that may be substituted, there are given, for example, acid halides such as phenylacetyl chloride, phenylpropionyl chloride, chlorophenylacetyl chloride, 4-phenylbutyryl chloride, 6-phenylhexanoyl chloride, and nitrophenylacetyl chloride. In addition, as a compound capable of providing a phenoxyalkyl group having 7 to 10 carbon atoms that may be substituted, there are given, for example, phenoxyacetyl chloride, phenoxypropionyl chloride, chlorophenoxyacetyl chloride, and nitrophenoxyacetyl chloride. In addition, as a compound capable of providing a heterocyclic group that may be substituted, there are given, for example, acid halides such as 2-thenoyl chloride, thiophene-2-acetyl chloride, chloronicotinoyl chloride, 2-furoyl chloride, and quinolinecarbonyl chloride. In addition, as a compound capable of providing a condensed ring group that may be substituted, there are given, for example, acid halides such as naphthoyl chloride, 2-ethoxy-1-naphthoyl chloride, and anthracenecarboxylic chloride.

It should be noted that there is no need to perform the reactions I to III in the stated order, and the reaction steps may be performed while their order is appropriately changed.

Any appropriate solvent can be used as a solvent to be used in each of the reactions depending on, for example, a compound to be used in the reaction. In addition, each of the reactions may be performed in the presence of any appropriate catalyst as required.

B. Photopolymerization Initiator

A photopolymerization initiator of the present invention contains at least one kind of the fluorene-based compound. The photopolymerization initiator of the present invention can have sensitivity to an active energy ray higher than that of a conventional photopolymerization initiator (such as a compound containing a carbazole skeleton) by containing the fluorene-based compound. In addition, a photopolymerization initiator also having a characteristic (such as solubility or transparency) more excellent than that of the conventional photopolymerization initiator can be provided.

In addition, the photopolymerization initiator of the present invention can provide a photopolymerization initiator having characteristics more excellent that those of the conventional photopolymerization initiator by appropriately selecting a functional group to be bonded to its fluorene skeleton. For example, a photopolymerization initiator containing at least one kind of the compounds 1, 4, 8, D-4, D-8, and D-12 can have additionally excellent solubility. In addition, a photopolymerization initiator containing at least one kind of the compounds 1, 2, 8, 11, D-1, D-2, D-3, D-4, D-12, and D-14 can have additionally high sensitivity to the active energy ray. Further, for example, a photopolymerization initiator containing at least one kind of the compounds 4, 6, 8, 9, 11, and D-8 can provide a photosensitive composition and a formed product each having additionally excellent transparency.

The photopolymerization initiator of the present invention may contain two or more kinds of the fluorene-based compounds depending on, for example, desired characteristics and desired sensitivity. In addition, the initiator may be used in combination with any appropriate other photopolymerization initiator except the fluorene-based compound.

C. Photosensitive Composition

A photosensitive composition of the present invention contains a compound having at least one ethylenically unsaturated bond and the photopolymerization initiator. As described above, the photopolymerization initiator of the present invention has high sensitivity to an active energy ray. Accordingly, a photosensitive composition having high reactivity with the active energy ray can be provided at an additionally low cost.

Any appropriate compound applicable to a photosensitive composition can be used as the compound having at least one ethylenically unsaturated bond. Examples of the compound include: unsaturated aliphatic hydrocarbons such as ethylene and propylene; unsaturated monobasic acids such as (meth)acrylic acid and crotonic acid; unsaturated polybasic acids such as a polyfunctional (meth)acrylate having one carboxyl group and two or more (meth)acryloyl groups; esters of unsaturated monobasic acids and alcohols, polyhydric alcohols, or polyhydric phenols such as 2-hydroxyethyl (meth)acrylate, glycidyl (meth)acrylate, methyl (meth)acrylate, and ethylene glycol di(meth)acrylate; acid anhydrides of unsaturated polybasic acids such as maleic anhydride; amides of unsaturated monobasic acids and polyvalent amines such as (meth)acrylamide; unsaturated aldehydes such as acrolein; unsaturated nitriles such as (meth)acrylonitrile; unsaturated aromatic compounds such as styrene and vinylbenzyl glycidyl ether; unsaturated ketones such as methyl vinyl ketone; unsaturated amine compounds such as vinylamine and allylamine; vinyl alcohols such as allyl alcohol; vinyl ethers such as vinyl methyl ether and allyl glycidyl ether; unsaturated imides such as maleimide and N-phenylmaleimide; indenes; aliphatic conjugated dienes such as 1,3-butadiene; and macromonomers each having a mono(meth)acryloyl group at a terminal of a molecular chain of a polymer such as polystyrene or polysiloxane; vinyl chloride; vinylurethane compounds of hydroxyl group-containing vinyl monomers and polyisocyanate compounds; vinylepoxy compounds of hydroxyl group-containing vinyl monomers and polyepoxy compounds; and a cardo resin. They may be used alone or in combination. In addition, when two or more kinds of the compounds are used, the compounds may be used as a copolymer by copolymerizing the compounds in advance.

In addition, the photosensitive composition of the present invention may be provided as an alkali-developable photosensitive resin composition by using an alkali-developable compound having an ethylenically unsaturated bond as the polymerizable compound having at least one ethylenically unsaturated bond. A resin obtained as described below can be used as the alkali-developable compound having an ethylenically unsaturated bond: an unsaturated monobasic acid is caused to act on a copolymer of an acrylate, a phenol novolac epoxy resin and/or a cresol novolac epoxy resin, a polyphenylmethane-type epoxy resin having a polyfunctional epoxy group, or an epoxy compound, and a polybasic acid anhydride is further caused to act on the resultant.

Examples of the unsaturated monobasic acid include acrylic acid, methacrylic acid, crotonic acid, cinnamic acid, and sorbic acid. In addition, examples of the polybasic acid anhydride include biphenyltetracarboxylic anhydride, succinic anhydride, maleic anhydride, trimellitic anhydride, and pyromellitic anhydride.

The content of the photopolymerization initiator in the photosensitive composition can be set to any appropriate value depending on applications and the characteristics of the fluorene-based compound to be used. The content of the photopolymerization initiator in the photosensitive composition is, for example, from 0.1 part by weight to 30 parts by weight, preferably from 1 part by weight to 20 parts by weight with respect to 100 parts by weight of the compound containing at least one ethylenically unsaturated bond.

The photosensitive composition of the present invention can contain any appropriate other additive other than the compound having at least one ethylenically unsaturated bond and the photopolymerization initiator. Examples of the other additive include a surfactant, a plasticizer, a filler, a leveling agent, an antioxidant, a UV absorber, a catalyst, a dispersing aid, a sensitizer, a cross-linking agent, a pigment, a dyestuff, an inorganic compound, a coloring material, a solvent, and a polymerization inhibitor.

Examples of the solvent include: ketones such as acetone, methyl ethyl ketone, and cyclohexanone; ether-based solvents such as ethyl ether, dioxane, tetrahydrofuran, 1,2-dimethoxyethane, propylene glycol monomethyl ether (PGME), dipropylene glycol dimethyl ether, and diethylene glycol dibutyl ether; ester-based solvents such as methyl acetate, ethyl acetate, butyl acetate, and ethyl lactate; cellosolve-based solvents such as ethylene glycol monomethyl ether, 3-methoxybutyl acetate, and propylene glycol monomethyl ether acetate (PGMEA); alcohol-based solvents such as methanol, ethanol, propanol, and amyl alcohol; ether ester-based solvents such as ethylene glycol monomethyl acetate and propylene glycol methyl acetate; aromatic hydrocarbon-based solvents such as benzene, toluene, and xylene; aliphatic hydrocarbon-based solvents such as hexane, heptane, and cyclohexane; halogenated aliphatic hydrocarbon-based solvents such as methylene chloride, chloroform, carbon tetrachloride, and 1,2-dichloroethane; halogenated aromatic hydrocarbon-based solvents such as chlorobenzene; and aniline, triethylamine, pyridine, acetic acid, acetonitrile, N,N-dimethylformamide, N-methylpyrrolidone, dimethyl sulfoxide, and water. The solvents may be used alone or as a mixed solvent of two or more kinds thereof. The solvent is preferably a ketone, a cellosolve-based solvent, or an ether ester-based solvent. The use of any such solvent provides excellent compatibility.

The photosensitive composition of the present invention can be applied to any appropriate application. As described above, the photopolymerization initiator of the present invention can have excellent characteristics by appropriately selecting a functional group with which its fluorene-based compound is substituted. Accordingly, there can be provided a photosensitive composition capable of exhibiting an additionally excellent effect in the application to which the photosensitive composition is applicable.

The application of the photosensitive composition is not particularly limited, and the composition can be used in any appropriate application. The composition can be used in various applications such as: a photocurable paint; a photocurable ink; a photocurable adhesive; a printing plate; a printing ink; a dental composition; a material for holographic recording; a recording material, e.g., an image recording material; a printed circuit board; a color filter in a liquid crystal display element for color display, e.g., a color television, a PC monitor, a personal digital assistant, or a digital camera; a mask for plating; a solder resist; a magnetic recording material; an optical switch; an electronic circuit; and various photoresist materials or protective films.

EXAMPLES

Hereinafter, the present invention is specifically described by way of Examples. However, the present invention is by no means limited by Examples described below. In addition, the term "part(s)" means "part(s) by weight." In each of the reaction schemes in Examples section, the character "化合物" represents "Compound".

Synthesis Example 1

Synthesis of Compound 1

A fluorene-based compound (the compound 1) was synthesized by the following synthesis method.

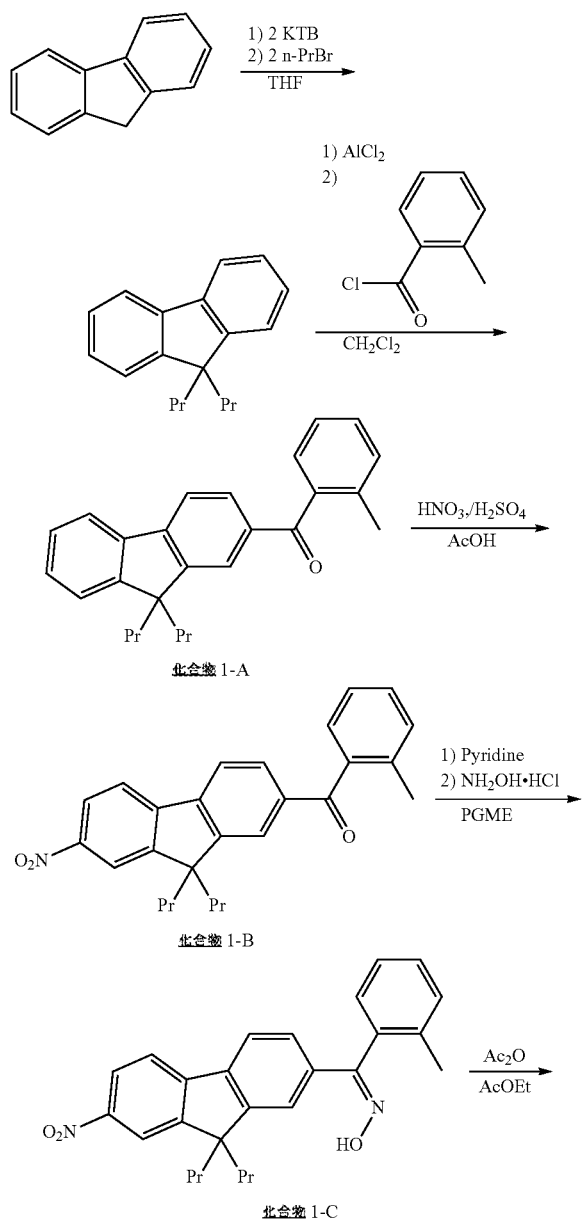

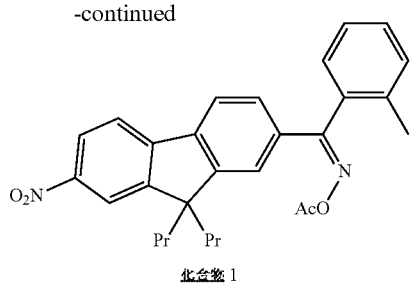

250.0 Parts by weight of tetrahydrofuran (THF) and 42.2 parts by weight of potassium tert-butoxide (KTB) were loaded into a reaction vessel, and 25.0 parts by weight of fluorene was added to the mixture. Next, 40.7 parts by weight of propyl bromide was dropped to the reaction vessel. The liquid was heated to 40° C. and stirred for 3 hours. Next, the liquid was cooled to room temperature, ethyl acetate and water were injected into the liquid to separate an oil layer, and the oil layer was repeatedly washed with water twice. Next, the oil layer was dried with anhydrous magnesium sulfate and then anhydrous magnesium sulfate was separated by filtration. The filtrate was concentrated to provide 37.7 parts by weight (yield: 100%, HPLC purity: 92%) of 9,9-dipropylfluorene.

37.0 Parts by weight of 9,9-dipropylfluorene thus obtained, 370.0 parts by weight of methylene chloride, and 29.6 parts by weight of aluminum chloride were loaded into a reaction vessel, and the mixture was stirred. The liquid was cooled to 10° C., 22.8 parts by weight of o-toluoyl chloride was dropped to the liquid, and the mixture was further stirred for 4 hours. The reaction liquid was injected into 370.0 parts by weight of water cooled to 10° C. or less, and an oil layer was separated and washed with an aqueous solution of potassium carbonate. Next, the oil layer was dried with anhydrous magnesium sulfate. After that, anhydrous magnesium sulfate was separated by filtration and the filtrate was concentrated to provide 51.2 parts by weight (yield: 94%, HPLC purity: 85%) of a compound 1-A.

50.0 Parts by weight of the resultant compound 1-A and 500.0 parts by weight of acetic acid were loaded into a reaction vessel, 10.8 parts by weight of fuming nitric acid was dropped to the mixture, and the liquid was heated to 80° C. 13.3 Parts by weight of concentrated sulfuric acid was dropped to the reaction liquid and the mixture was stirred at 80° C. for 3 hours. After the stirring, the mixture was cooled to room temperature, and water and ethyl acetate were injected into the mixture to separate an oil layer. The oil layer was repeatedly washed with water and an aqueous solution of potassium carbonate. Next, the oil layer was dried with anhydrous magnesium sulfate and then anhydrous magnesium sulfate was separated by filtration, followed by the concentration of the filtrate. The resultant oily matter was isolated and purified by silica gel column chromatography to provide 33.7 parts by weight (yield: 60%, HPLC purity: 99%) of a compound 1-B.

30.0 Parts by weight of the resultant compound 1-B, 90.0 parts by weight of propylene glycol monomethyl ether (PGME), and 34.4 parts by weight of pyridine were loaded into a reaction vessel, and the mixture was stirred. Next, 30.3 parts by weight of hydroxylamine hydrochloride was added to the mixture, and the whole was heated to 140° C. and stirred for 4 hours. The reaction liquid was cooled to room temperature, and water and ethyl acetate were injected into the reaction liquid to separate an oil layer. The oil layer was washed with water, dilute hydrochloric acid, and an aqueous solution of sodium chloride again. Next, the oil layer was dried with anhydrous magnesium sulfate and then anhydrous magnesium sulfate was separated by filtration. The filtrate was concentrated to provide 28.0 parts by weight (yield: 90%, HPLC purity: 96%) of a compound 1-C.

25.0 Parts by weight of the resultant compound 1-C and 125.0 parts by weight of ethyl acetate were loaded into a reaction vessel, and 13.8 parts by weight of acetic anhydride was dropped to the mixture, followed by stirring at room temperature for 5 hours. Water and ethyl acetate were injected into the reaction liquid to separate an oil layer, and the oil layer was washed with an aqueous solution of potassium carbonate and an aqueous solution of sodium chloride. Next, the oil layer was dried with anhydrous magnesium sulfate. Anhydrous magnesium sulfate was separated by filtration and the filtrate was concentrated. The resultant product was recrystallized with ethyl acetate and hexane to provide 17.3 parts by weight (yield: 63%, HPLC purity: 99%) of the compound 1. The structure of the resultant compound 1 was confirmed by a $^1$H-NMR spectrum (CDCl$_3$). The $^1$H-NMR spectrum is described below.

δ [ppm]: 8.20-8.27 (m: 2H), 7.77-7.82 (m: 2H), 7.70-7.73 (d: 1H), 7.28-7.45 (m: 4H), 7.12 (dd: 1H), 2.17 (s: 3H), 2.06 (s: 3H), 2.00 (t: 4H), 0.52-0.72 (m: 10H)

Synthesis Example 2

Synthesis of Compound 2

The compound 2 was synthesized in the same manner as in Synthesis Example 1 except that propyl bromide was changed to hexyl bromide. The resultant compound 2 had a yield of 40% and a HPLC purity of 99%. The structure of the resultant compound was confirmed by a $^1$H-NMR spectrum (CDCl$_3$). The $^1$H-NMR spectrum is described below.

δ [ppm]: 8.27 (dd: 1H), 8.20 (d: 1H), 7.81 (d: 1H), 7.73 (d: 1H), 7.67 (d: 1H), 7.54 (dd: 1H), 7.40 (dt: 1H), 7.28-7.36 (m: 2H), 7.13 (d: 1H), 2.15 (s: 3H), 2.08 (s: 3H), 2.00 (t: 4H), 0.97-1.12 (m: 12H), 0.78 (t: 6H), 0.50-0.60 (m: 4H)

Synthesis Example 3

Synthesis of Compound 3

The compound 3 was synthesized in the same manner as in Synthesis Example 1 except that o-toluoyl chloride was changed to cyclohexanecarbonyl chloride. The resultant compound 3 had a yield of 17% and a HPLC purity of 97%. The structure of the resultant compound was confirmed by a $^1$H-NMR spectrum (CDCl$_3$). The $^1$H-NMR spectrum is described below.

δ [ppm]: 8.20-8.30 (m: 2H), 7.76-7.85 (m: 2H), 7.40-7.45 (m: 1H), 7.18-7.22 (m: 1H), 3.24-3.34 (m: 0.5H, isomer), 2.68-2.78 (m: 0.5H, isomer), 1.12-2.20 (m: 17H), 0.58-0.74 (m: 10H)

Synthesis Example 4

Synthesis of Compound 4

A fluorene-based compound (the compound 4) was synthesized by the following synthesis method.

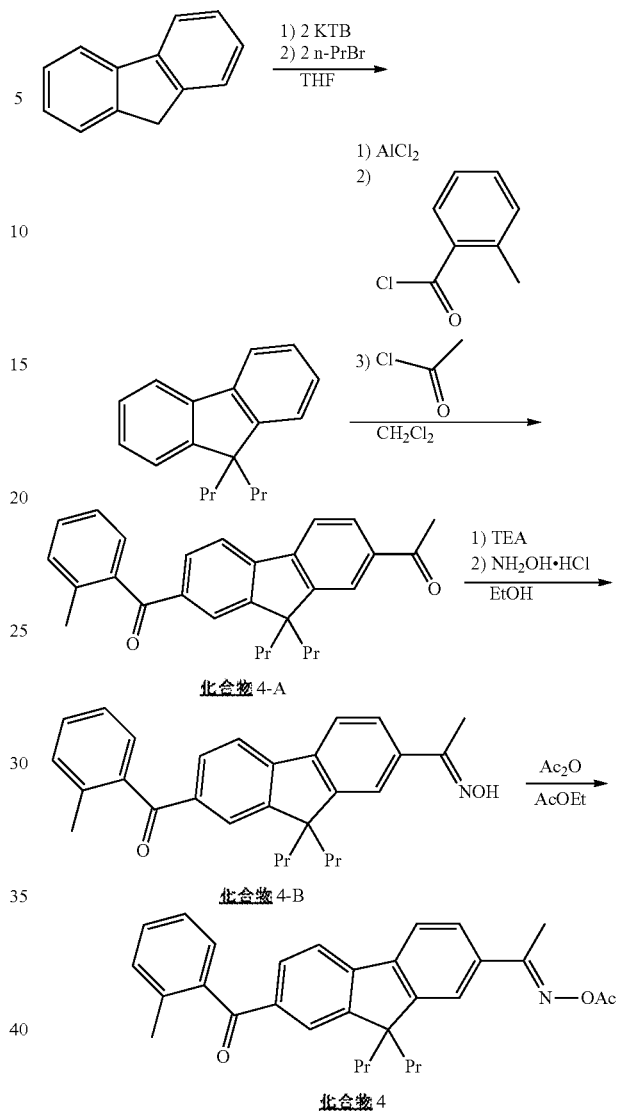

37.0 Parts by weight of 9,9-dipropylfluorene obtained in the same manner as in Synthesis Example 1, 370.0 parts by weight of methylene chloride, and 29.6 parts by weight of aluminum chloride were loaded into a reaction vessel, and the mixture was stirred. The liquid was cooled to 10° C., and 22.8 parts by weight of o-toluoyl chloride was dropped to the liquid. After the completion of the dropping, the mixture was stirred for 1 hour. Next, 29.6 parts by weight of aluminum chloride and 12.8 parts by weight of acetyl chloride were added to the reaction liquid, and the mixture was heated to room temperature and stirred for 3 hours. The reaction liquid was injected into cold water, and an oil layer was separated and washed with an aqueous solution of potassium carbonate and an aqueous solution of sodium chloride. Next, the oil layer was dried with anhydrous magnesium sulfate. After that, anhydrous magnesium sulfate was separated by filtration and the filtrate was concentrated. The resultant oily matter was isolated and purified by silica gel column chromatography to provide 43.7 parts by weight (yield: 72%, HPLC purity: 99%) of a compound 4-A.

30.0 Parts by weight of the compound 4-A, 300.0 parts by weight of ethanol, and 8.1 parts by weight of triethylamine (TEA) were loaded into a reaction vessel, and the mixture was stirred. Next, 7.6 parts by weight of hydroxylamine hydrochloride was added to the mixture, and the whole was stirred for 3 hours. Water and ethyl acetate were injected into the reaction liquid to separate an oil layer. The oil layer was washed with water, dilute hydrochloric acid, and an aqueous solution of sodium chloride. Next, the oil layer was dried with anhydrous magnesium sulfate and then anhydrous magnesium sulfate was separated by filtration. The filtrate was concentrated to provide 28.2 parts by weight (yield: 90%, HPLC purity: 99%) of a compound 4-B.

25.0 Parts by weight of the resultant compound 4-B and 125.0 parts by weight of ethyl acetate were loaded into a reaction vessel, and 13.9 parts by weight of acetic anhydride was dropped to the mixture, followed by stirring at room temperature for 3 hours. Water and ethyl acetate were injected into the reaction liquid to separate an oil layer, and the oil layer was washed with an aqueous solution of potassium carbonate and an aqueous solution of sodium chloride. Next, the oil layer was dried with anhydrous magnesium sulfate. Anhydrous magnesium sulfate was then separated by filtration and the filtrate was concentrated. The resultant product was recrystallized with methanol to provide 19.2 parts by weight (yield: 70%, HPLC purity: 98%) of the compound 4. The structure of the resultant compound 4 was confirmed by a $^1$H-NMR spectrum (CDCl$_3$). The $^1$H-NMR spectrum is described below.

δ [ppm]: 7.91 (s: 1H), 7.76 (dd: 3H), 7.70 (d: 1H), 7.42 (dd: 1H), 7.26-7.37 (m: 4H), 2.46 (s: 3H), 2.36 (s: 3H), 2.30 (s: 3H), 2.00 (t: 4H), 0.62-0.72 (m: 10H)

Synthesis Example 5

Synthesis of Compound 5

The compound 5 was synthesized in the same manner as in Synthesis Example 4 except that o-toluoyl chloride was changed to 1-naphthoyl chloride. The resultant compound 5 had a yield of 25% and a HPLC purity of 97%. The structure of the resultant compound was confirmed by a $^1$H-NMR spectrum (CDCl$_3$). The $^1$H-NMR spectrum is described below.

δ [ppm]: 8.52 (s: 1H), 7.26-7.91 (m: 12H), 2.36 (s: 3H), 2.30 (s: 3H), 2.00 (t: 4H), 0.62-0.72 (m: 10H)

Synthesis Example 6

Synthesis of Compound 6

The compound 6 was synthesized in the same manner as in Synthesis Example 4 except that propyl bromide was changed to hexyl bromide. The resultant compound 6 had a yield of 30% and a HPLC purity of 99%. The structure of the resultant compound was confirmed by a $^1$H-NMR spectrum (CDCl$_3$). The $^1$H-NMR spectrum is described below.

δ [ppm]: 7.87 (s: 1H), 7.79 (d: 2H), 7.72-7.60 (m: 3H), 7.25-7.47 (m: 4H), 2.47 (s: 3H), 2.36 (s: 3H), 2.31 (s: 3H), 1.97-2.05 (m: 4H), 0.96-1.18 (m: 12H), 0.77 (t: 6H), 0.53-0.65 (m: 4H)

Synthesis Example 7

Synthesis of Compound 7

The compound 7 was synthesized in the same manner as in Synthesis Example 4 except that o-toluoyl chloride was changed to benzoyl chloride. The resultant compound 7 had a yield of 30% and a HPLC purity of 99%. The structure of the resultant compound was confirmed by a $^1$H-NMR spectrum (CDCl$_3$). The $^1$H-NMR spectrum is described below.

δ [ppm]: 7.78-7.87 (m: 7H), 7.75 (brs: 1H), 7.58-7.63 (m: 1H), 7.48-7.66 (m: 2H), 2.48 (s: 3H), 2.31 (s: 3H), 2.00 (t: 4H), 0.62-0.72 (m: 10H)

Synthesis Example 8

Synthesis of Compound 8

The compound 8 was synthesized in the same manner as in Synthesis Example 4 except that propyl bromide and o-toluoyl chloride were changed to hexyl bromide and benzoyl chloride, respectively. The resultant compound 8 had a yield of 32% and a HPLC purity of 99%. The structure of the resultant compound was confirmed by a $^1$H-NMR spectrum (CDCl$_3$). The $^1$H-NMR spectrum is described below.

δ [ppm]: 7.79-7.86 (m: 7H), 7.75 (s: 1H), 7.59-7.66 (m: 1H), 7.48-7.55 (m: 2H), 2.47 (s: 3H), 2.31 (s: 3H), 1.98-2.07 (m: 4H), 0.98-1.18 (m: 12H), 0.77 (t: 6H), 0.55-0.68 (m: 4H)

Synthesis Example 9

Synthesis of Compound 9

A fluorene-based compound (the compound 9) was synthesized by the following synthesis method.

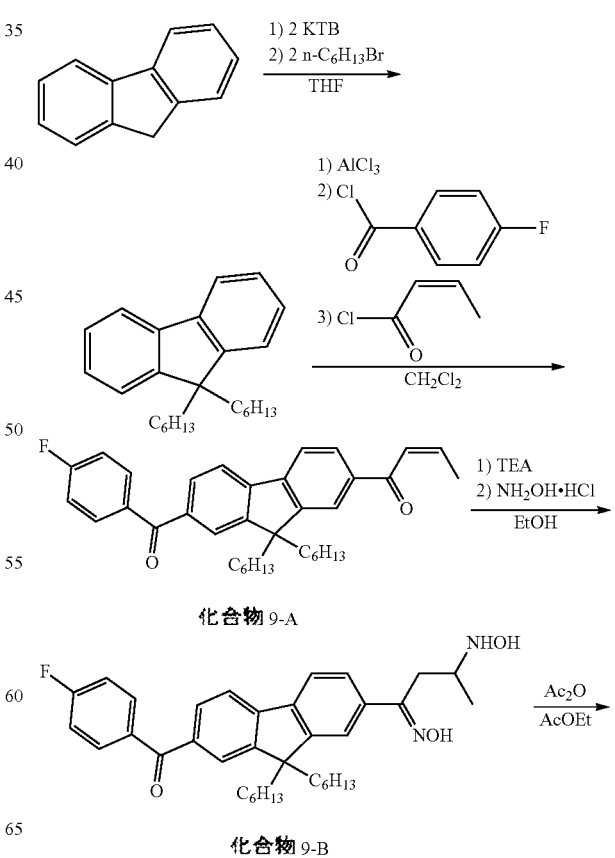

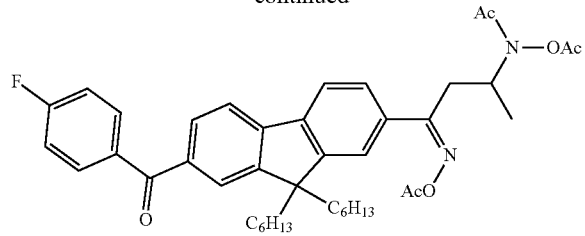

化合物 9

50.0 Parts by weight of 9,9-dihexylfluorene obtained in the same manner as in Synthesis Example 1 except that hexyl bromide was used instead of propyl bromide, 500.0 parts by weight of methylene chloride, and 29.9 parts by weight of aluminum chloride were loaded into a reaction vessel, and the mixture was stirred. The liquid was cooled to 10° C. and 26.1 parts by weight of p-fluorobenzoyl chloride was dropped to the liquid. After the completion of the dropping, the reaction liquid was warmed to room temperature and stirred for 3 hours. Next, 29.9 parts by weight of aluminum chloride and 15.6 parts by weight of crotonoyl chloride were added to the reaction liquid, and the mixture was stirred for 20 hours. The reaction liquid was injected into cold water, and an oil layer was separated and washed with an aqueous solution of potassium carbonate and an aqueous solution of sodium chloride. Next, the oil layer was dried with anhydrous magnesium sulfate and then anhydrous magnesium sulfate was separated by filtration, followed by the concentration of the filtrate. The resultant oily matter was isolated and purified by silica gel column chromatography to provide 21.1 parts by weight (yield: 35%, HPLC purity: 99%) of a compound 9-A.

20.0 Parts by weight of the compound 9-A, 200.0 parts by weight of ethanol, and 7.7 parts by weight of triethylamine were loaded into a reaction vessel, and the mixture was stirred. Next, 6.0 parts by weight of hydroxylamine hydrochloride was added to the mixture, and the whole was warmed to 80° C. and stirred for 3 hours. The reaction liquid was cooled to room temperature, and then water and ethyl acetate were injected into the reaction liquid to separate an oil layer. The oil layer was washed with water, dilute hydrochloric acid, and an aqueous solution of sodium chloride. Next, the oil layer was dried with anhydrous magnesium sulfate and then anhydrous magnesium sulfate was separated by filtration. The filtrate was concentrated to provide 21.8 parts by weight (yield: 100%, HPLC purity: 80%) of a compound 9-B.

20.0 Parts by weight of the resultant compound 9-B and 100.0 parts by weight of ethyl acetate were loaded into a reaction vessel, and 13.8 parts by weight of acetic anhydride was dropped to the mixture, followed by stirring at room temperature for 20 hours. Water and ethyl acetate were injected into the reaction liquid to separate an oil layer, and the oil layer was washed with an aqueous solution of potassium carbonate and an aqueous solution of sodium chloride. Next, the oil layer was dried with anhydrous magnesium sulfate. Anhydrous magnesium sulfate was then separated by filtration and the filtrate was concentrated. The resultant oily product was isolated and purified by silica gel column chromatography to provide 7.5 parts by weight (yield: 30%, HPLC purity: 97%) of the compound 9. The structure of the resultant compound was confirmed by a $^1$H-NMR spectrum (CDCl$_3$). The $^1$H-NMR spectrum is described below.

δ [ppm]: 7.86 (q: 2H), 7.75-7.83 (m: 6H), 7.18 (t: 2H), 4.84 (brs: 1H), 3.14-3.36 (m: 2H), 2.33 (s: 3H), 2.25 (s: 3H), 2.00-2.10 (m: 4H), 1.92 (s: 3H), 0.98-1.20 (m: 15H), 0.76 (t: 6H), 0.58-0.67 (m: 4H)

Synthesis Example 10

Synthesis of Compound 10

The compound 10 was synthesized in the same manner as in Synthesis Example 9 except that p-fluorobenzoyl chloride was changed to p-trifluoromethylbenzoyl chloride. The resultant compound 10 had a yield of 22% and a HPLC purity of 97%. The structure of the resultant compound was confirmed by a $^1$H-NMR spectrum (CDCl$_3$). The $^1$H-NMR spectrum is described below.

δ [ppm]: 7.70-7.88 (m: 10H), 4.84 (brs: 1H), 3.14-3.36 (m: 2H), 2.33 (s: 3H), 2.25 (s: 3H), 2.00-2.10 (m: 4H), 1.92 (s: 3H), 0.98-1.20 (m: 15H), 0.76 (t: 6H), 0.58-0.67 (m: 4H)

Synthesis Example 11

Synthesis of Compound 11

The compound 11 was synthesized in the same manner as in Synthesis Example 9 except that p-fluorobenzoyl chloride was changed to 2-thenoyl chloride. The resultant compound 11 had a yield of 28% and a HPLC purity of 96%. The structure of the resultant compound was confirmed by a $^1$H-NMR spectrum (CDCl$_3$). The $^1$H-NMR spectrum is described below.

δ [ppm]: 7.73-7.93 (m: 7H), 7.67 (dd: 1H), 7.20 (q: 1H), 4.74-4.96 (brs: 1H), 3.14-3.36 (m: 2H), 2.34 (s: 3H), 2.24 (s: 3H), 2.02-2.10 (m: 4H), 1.91 (s: 3H), 0.94-1.20 (m: 15H), 0.76 (t: 6H), 0.56-0.68 (m: 4H)

Synthesis Example 12

Synthesis of Compound 12

The compound 12 was synthesized in the same manner as in Synthesis Example 9 except that p-fluorobenzoyl chloride was changed to p-nitrobenzoyl chloride. The resultant compound 12 had a yield of 19% and a HPLC purity of 97%. The structure of the resultant compound was confirmed by a $^1$H-NMR spectrum (CDCl$_3$). The $^1$H-NMR spectrum is described below.

δ [ppm]: 8.37 (m: 2H), 7.97 (d: 1H), 7.50-7.88 (m: 6H), 7.25-7.50 (m: 1H), 4.84 (brs: 1H), 3.10-3.36 (m: 2H), 2.23-2.40 (m: 4H), 1.90-2.16 (m: 9H), 0.98-1.20 (m: 15H), 0.76 (t: 6H), 0.50-0.67 (m: 4H)

Synthesis Example 13

Synthesis of Compound 13

A fluorene-based compound (the compound 13) was synthesized by the following synthesis method.

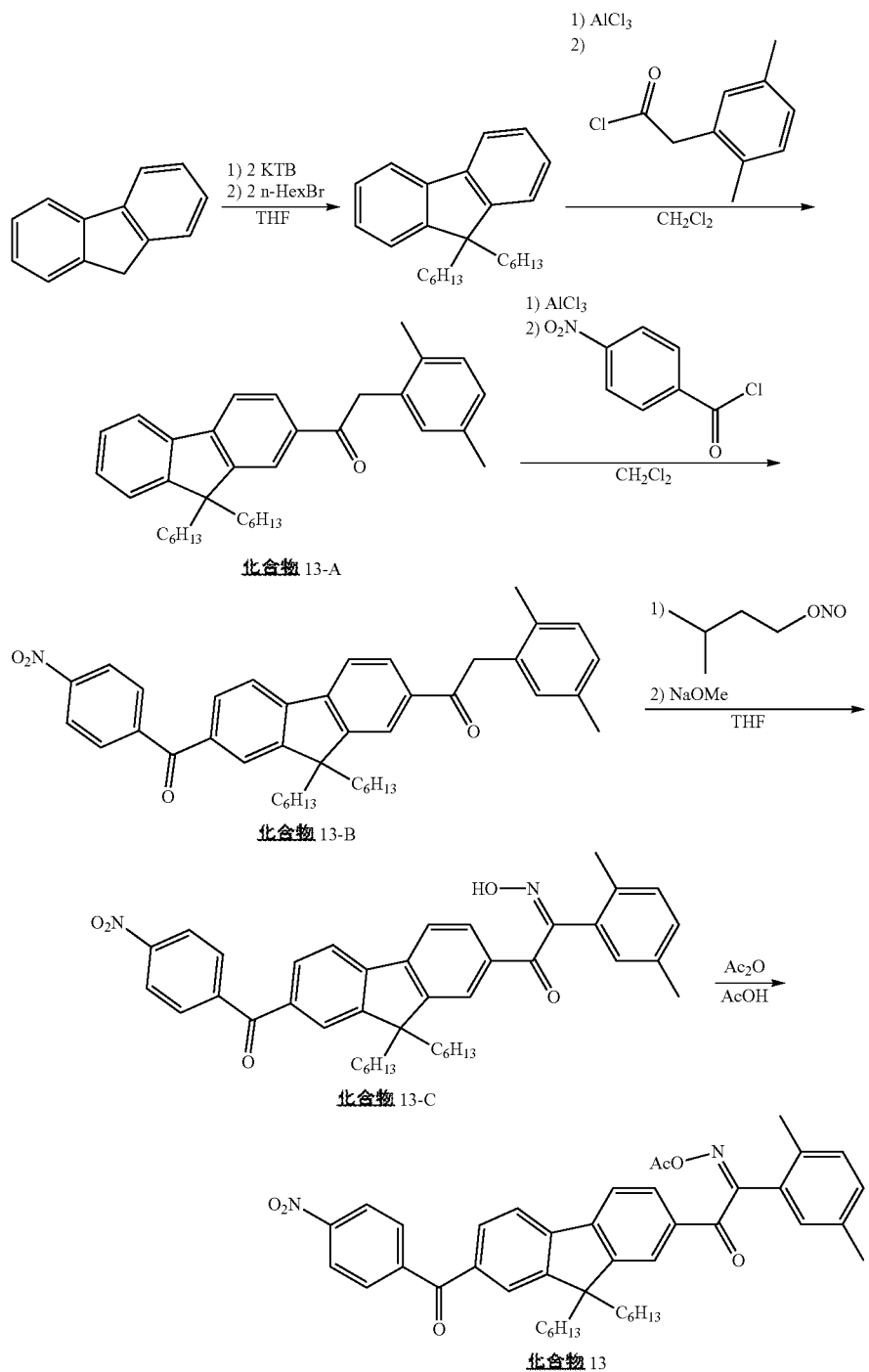

50.0 Parts by weight of 9,9-dihexylfluorene obtained in the same manner as in Synthesis Example 1 except that hexyl bromide was used instead of propyl bromide, 500.0 parts by weight of methylene chloride, and 29.9 parts by weight of aluminum chloride were loaded into a reaction vessel, and the mixture was stirred. The liquid was cooled to 10° C. and 30.0 parts by weight of 2,5-dimethylphenylacetyl chloride was dropped to the liquid. After the completion of the dropping, the reaction liquid was warmed to room temperature and stirred for 3 hours. The reaction liquid was injected into cold water, and an oil layer was separated and washed with an aqueous solution of potassium carbonate and an aqueous solution of sodium chloride. Next, the oil layer was dried with anhydrous magnesium sulfate and then anhydrous magnesium sulfate was separated by filtration, followed by the concentration of the filtrate. 120 Parts by weight of methanol was added to the resultant solid matter, and the mixture was warmed to 60° C. and stirred for 1 hour. After the solution had been cooled, 25 parts by weight of water was added to the solution and the mixture was filtered to provide 50.2 parts by weight (yield: 70%, HPLC purity: 90%) of a compound 13-A.

50.0 Parts by weight of the compound 13-A, 500.0 parts by weight of methylene chloride, and 34.7 parts by weight of aluminum chloride were loaded into a reaction vessel, and the mixture was stirred. The liquid was cooled to 10° C., and 19.3 parts by weight of p-nitrobenzoyl chloride was dropped to the liquid. After the completion of the dropping, the reaction liquid was warmed to 40° C. and stirred for 5 hours. The reaction liquid was injected into cold water, and an oil layer was separated and washed with an aqueous solution of potassium carbonate and an aqueous solution of sodium chloride. Next, the oil layer was dried with anhydrous magnesium sulfate. After that, anhydrous magnesium sulfate was separated by filtration and the filtrate was concentrated to provide 63.5 parts by weight (yield: 97%, HPLC purity: 80%) of a compound 13-B.

60.0 Parts by weight of the compound 13-B and 300.0 parts by weight of tetrahydrofuran were loaded into a reaction vessel, and the mixture was stirred. 12.3 Parts by weight of isoamyl nitrite (isopentyl nitrite) was added to the solution, 18.4 parts by weight of a 28% solution of sodium methoxide in methanol was added to the solution, and the mixture was stirred at room temperature for 1 hour. Ethyl acetate and water were added to the liquid to separate an oil layer, and the oil layer was washed with water twice. Next, the oil layer was dried with anhydrous magnesium sulfate and then anhydrous magnesium sulfate was separated by filtration. Oily matter obtained by concentrating the filtrate was isolated and purified by silica gel column chromatography to provide 22.0 parts by weight (yield: 35%, HPLC purity: 95%) of a compound 13-C.

20.0 Parts by weight of the compound 13-C and 60.0 parts by weight of glacial acetic acid were loaded into a reaction vessel, and the mixture was stirred. 6.2 Parts by weight of acetic anhydride was added to the solution, and the mixture was warmed to 40° C. and stirred for 5 hours. The reaction liquid cooled to room temperature was injected into a mixed liquid of 800.0 parts by weight of water and 80.0 parts by weight of methanol, and the precipitated crystal was filtered to provide 15.1 parts by weight (yield: 71%, HPLC purity: 98%) of the compound 13. The structure of the resultant compound was confirmed by a $^1$H-NMR spectrum (CDCl$_3$). The $^1$H-NMR spectrum is described below.

δ [ppm]: 8.29-8.38 (m: 4H), 8.24 (d: 1H), 7.87-8.03 (m: 2H), 7.78-7.90 (m: 2H), 7.37-7.46 (m: 3H), 7.25 (s: 1H), 2.35 (s: 6H), 2.22 (s: 3H), 1.97-2.10 (m: 4H), 0.98-1.20 (m: 12H), 0.76 (t: 6H), 0.57-0.70 (m: 4H)

Synthesis Example 14

Synthesis of Compound 14

The compound 14 was synthesized in the same manner as in Synthesis Example 13 except that p-nitrobenzoyl chloride was changed to p-fluorobenzoyl chloride. The resultant compound 14 had a yield of 14% and a HPLC purity of 95%. The structure of the resultant compound was confirmed by a $^1$H-NMR spectrum (CDCl$_3$). The $^1$H-NMR spectrum is described below.

δ [ppm]: 8.15 (d: 1H), 7.85-8.00 (m: 2H), 7.78-7.90 (m: 4H), 7.37-7.46 (m: 3H), 7.25 (s: 1H), 7.01-7.10 (m: 2H), 2.35 (s: 6H), 2.22 (s: 3H), 1.97-2.10 (m: 4H), 0.98-1.20 (m: 12H), 0.76 (t: 6H), 0.57-0.70 (m: 4H)

Synthesis Example 15

Synthesis of Compound 15

A fluorene-based compound (the compound 15) was synthesized by the following synthesis method.

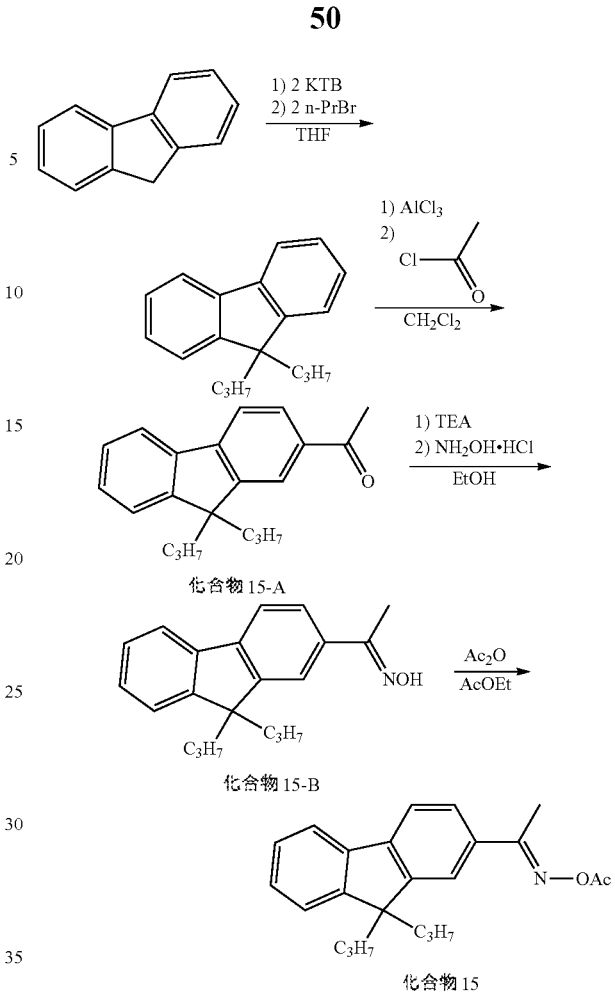

50.0 Parts by weight of 9,9-dipropylfluorene obtained in the same manner as in Synthesis Example 1, 500.0 parts by weight of methylene chloride, and 29.9 parts by weight of aluminum chloride were loaded into a reaction vessel, and the mixture was stirred. The liquid was cooled to 10° C., and 15.7 parts by weight of acetyl chloride was dropped to the liquid. After the completion of the dropping, the reaction liquid was warmed to room temperature and stirred for 3 hours. The reaction liquid was injected into cold water, and an oil layer was separated and washed with an aqueous solution of potassium carbonate and an aqueous solution of sodium chloride. Next, the oil layer was dried with anhydrous magnesium sulfate. After that, anhydrous magnesium sulfate was separated by filtration and the filtrate was concentrated. The resultant oily matter was isolated and purified by silica gel column chromatography to provide 26.3 parts by weight (yield: 45%, HPLC purity: 100%) of a compound 15-A.

25.0 Parts by weight of the compound 15-A and 125.0 parts by weight of methanol were loaded into a reaction vessel, and the mixture was stirred. 17.3 Parts by weight of triethylamine and 17.8 parts by weight of hydroxylamine hydrochloride were added to the solution, and the mixture was stirred at room temperature for 3 hours. A crystal precipitated by adding 125.0 parts by weight of water to the liquid was filtered to provide 18.4 parts by weight (yield: 70%, HPLC purity: 99%) of a compound 15-B.

15.0 Parts by weight of the compound 15-B and 75.0 parts by weight of tetrahydrofuran were loaded into a reaction vessel, 10.0 parts by weight of acetic anhydride was gradually added to the solution, and the mixture was stirred at room temperature for 3 hours. The reaction liquid was injected into a mixed liquid of 80.0 parts by weight of water and 20.0 parts by weight of methanol, and the precipitated crystal was filtered to provide 11.9 parts by weight (yield: 70%, HPLC purity: 100%) of the compound 15. The structure of the resultant compound was confirmed by a $^1$H-NMR spectrum (CDCl$_3$). The $^1$H-NMR spectrum is described below.

δ [ppm]: 7.78 (s: 1H), 7.72 (s: 3H), 7.30-7.40 (m: 3H), 2.35 (s: 3H), 2.28 (s: 3H), 1.92-2.02 (m: 4H), 0.55-0.70 (m: 10H)

Synthesis Example 16

Synthesis of Compound 16

The compound 16 was synthesized in the same manner as in Synthesis Example 15 except that dipropylation was omitted. The resultant compound 16 had a yield of 33% and a HPLC purity of 98%. The structure of the resultant compound was confirmed by a $^1$H-NMR spectrum (CDCl$_3$). The $^1$H-NMR spectrum is described below.

δ [ppm]: 8.00 (s: 1H), 7.72-7.85 (m: 3H), 7.58 (d: 1H), 7.30-7.43 (m: 2H), 3.95 (s: 2H), 2.46 (s: 3H), 2.26 (s: 3H)

Synthesis Example D-1

Synthesis of Compound D-1

The compound D-1 was synthesized in the same manner as in Synthesis Example 1 except that o-toluoyl chloride was changed to benzoyl chloride. The resultant compound D-1 had a yield of 15% and a HPLC purity of 99%. The structure of the resultant compound was confirmed by a $^1$H-NMR spectrum (CDCl$_3$). The $^1$H-NMR spectrum is described below.

δ [ppm]: 8.20-8.32 (m: 2H), 7.32-7.88 (m: 9H), 1.95-2.15 (m: 7H), 0.55-0.75 (m: 10H)

Synthesis Example D-2

Synthesis of Compound D-2

The compound D-2 was synthesized in the same manner as in Synthesis Example 1 except that o-toluoyl chloride was changed to 4-tert-butylbenzoyl chloride. The resultant compound D-2 had a yield of 12% and a HPLC purity of 93%. The structure of the resultant compound was confirmed by a $^1$H-NMR spectrum (CDCl$_3$). The $^1$H-NMR spectrum is described below.

δ [ppm]: 8.20-8.32 (m: 2H), 7.67-7.87 (m: 3H), 7.28-7.56 (m: 5H), 1.97-2.08 (m: 7H), 1.36 (d: 9H), 0.58-0.72 (m: 10H)

Synthesis Example D-3

Synthesis of Compound D-3

A fluorene-based compound (the compound D-3) was synthesized by the following synthesis method.

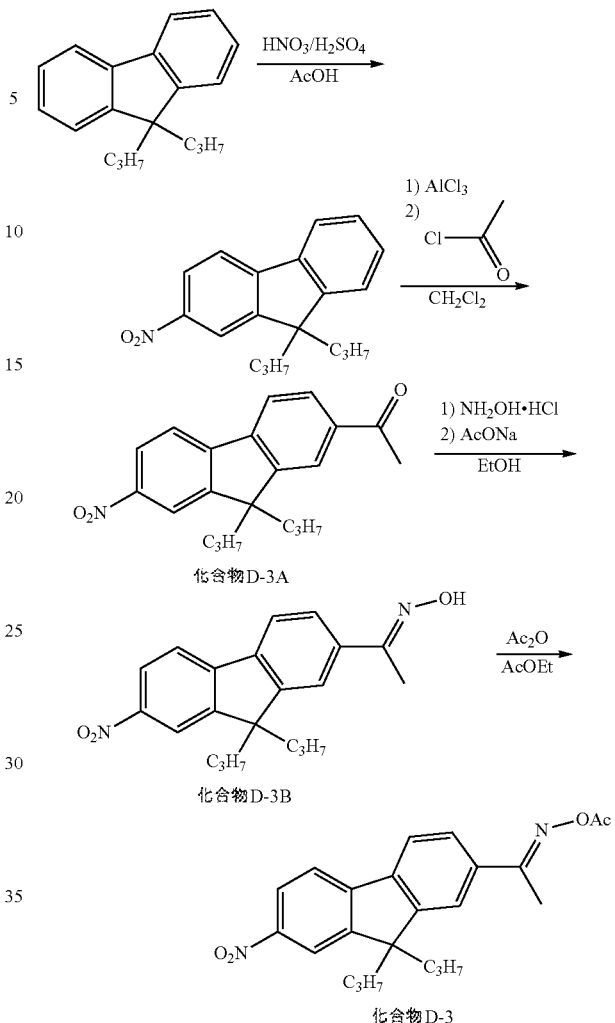

250 Parts by weight of acetic acid was added to 50.0 parts by weight of 9,9-dipropylfluorene obtained in the same manner as in Synthesis Example 1 to dissolve 9,9-dipropylfluorene. After that, 29.4 parts by weight of concentrated sulfuric acid was added to the solution and the mixture was warmed to 40° C. 29.0 Parts by weight of concentrated nitric acid was added to the mixture and the whole was stirred for 1 hour. After that, the reaction liquid was injected into water. The precipitated crystal was filtered to provide 54.3 parts by weight (yield: 92%, HPLC purity: 100%) of 2-nitro-9,9-dipropylfluorene.

500 Parts by weight of methylene chloride and 45.1 parts by weight of anhydrous aluminum chloride were added to 50.0 parts by weight of 2-nitro-9,9-dipropylfluorene. After that, 26.6 parts by weight of acetyl chloride was added to the mixture, and the whole was warmed to 40° C. and stirred for 4 hours. After the reaction liquid had been cooled, the reaction liquid was injected into ice water to be subjected to liquid separation. An oil layer was washed with 5% sodium bicarbonate water and water, and was then concentrated to provide 25.1 parts by weight (yield: 44%, HPLC purity: 99%) of a compound D-3A.

200 Parts by weight of ethanol, 16.5 parts by weight of hydroxylamine hydrochloride, and 19.4 parts by weight of anhydrous sodium acetate were added to 20 parts by weight of the compound D-3A, and the mixture was warmed to 40° C. and stirred for 2 hours. The reaction liquid was cooled with ice and the precipitated crystal was filtered to provide 20.9 parts by weight (yield: 100%, HPLC purity: 94%) of a compound D-3B.

200 Parts by weight of ethyl acetate was added to 20 parts by weight of the compound D-3B to dissolve the compound. After that, 17.4 parts by weight of acetic anhydride was added to the solution and the mixture was stirred at room temperature for 5 hours. Water was added to subject the mixture to liquid separation, and an oil layer was washed with 5% sodium bicarbonate water and water. The oil layer was concentrated and recrystallized with methanol to provide 16.9 parts by weight (yield: 75%, HPLC purity: 99%) of the compound D-3. The structure of the resultant compound D-3 was confirmed by a $^1$H-NMR spectrum (CDCl$_3$). The $^1$H-NMR spectrum is described below.

δ [ppm]: 8.27 (dd: 1H), 8.23 (d: 1H), 7.78-7.85 (m: 4H), 2.47 (s: 3H), 2.30 (s: 3H), 2.05 (t: 4H), 0.55-0.72 (m: 10H)

Synthesis Example D-4

Synthesis of Compound D-4

The compound D-4 was synthesized in the same manner as in Synthesis Example D-3 except that propyl bromide was changed to 3-methylbutyl bromide to provide 9,9-di(3-methylbutyl)fluorene. The resultant compound D-4 had a yield of 30% and a HPLC purity of 98%. The structure of the resultant compound was confirmed by a $^1$H-NMR spectrum (CDCl$_3$). The $^1$H-NMR spectrum is described below.

δ [ppm]: 8.28 (dd: 1H), 8.20 (d: 1H), 7.82 (t: 3H), 7.70 (s: 1H), 2.46 (s: 3H), 2.30 (s: 3H), 2.02-2.13 (m: 4H), 1.28 (sep: 2H), 0.62 (d: 12H), 0.34-0.50 (m: 4H)

Synthesis Example D-5

Synthesis of Compound D-5

The compound D-5 was synthesized in the same manner as in Synthesis Example D-3 except that propyl bromide was changed to cyclohexyl bromide to provide 9-cyclohexylfluorene. The resultant compound D-5 had a yield of 20% and a HPLC purity of 97%. The structure of the resultant compound was confirmed by a $^1$H-NMR spectrum (CDCl$_3$). The $^1$H-NMR spectrum is described below.

δ [ppm]: 8.40 (s: 1H), 8.30 (d: 1H), 8.00 (s: 1H), 7.75-7.90 (m: 3H), 4.03 (s: 1H), 2.45 (s: 3H), 2.26 (s: 3H), 0.8-1.8 (m: 11H)

Synthesis Example D-6

Synthesis of Compound D-6

The compound D-6 was synthesized in the same manner as in Synthesis Example D-3 except that propyl bromide was changed to 1,5-dibromopentane to provide spiro[cyclohexane-1,9'-fluorene]. The resultant compound D-6 had a yield of 5% and a HPLC purity of 99%. The structure of the resultant compound was confirmed by a $^1$H-NMR spectrum (CDCl$_3$). The $^1$H-NMR spectrum is described below.

δ [ppm]: 8.56 (d: 1H), 8.30 (dd: 1H), 8.03 (d: 1H), 7.78-7.88 (m: 3H), 2.47 (s: 3H), 2.30 (s: 3H), 1.62-2.00 (m: 10H)

Synthesis Example D-7

Synthesis of Compound D-7

A fluorene-based compound (the compound D-7) was synthesized by the following synthesis method.

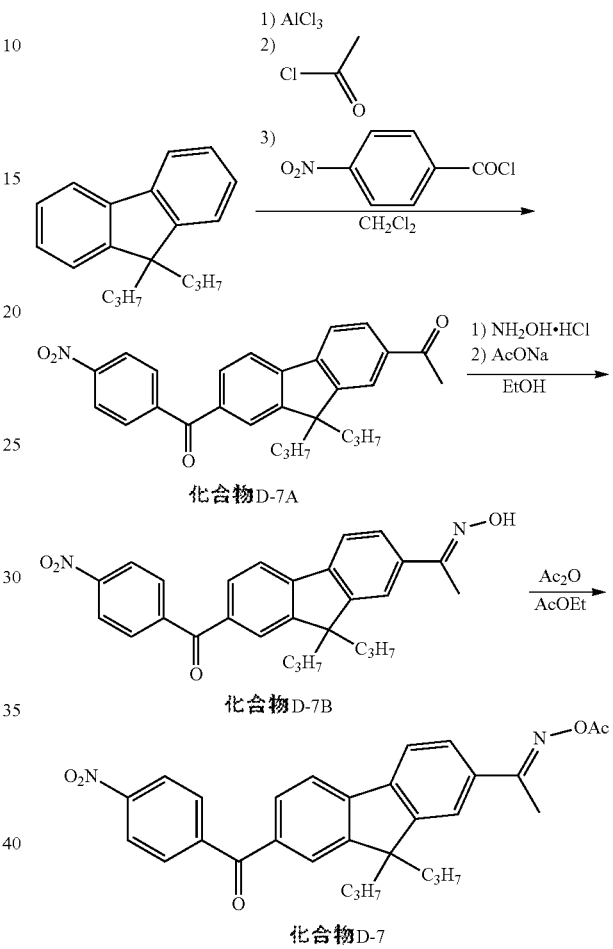

500 Parts by weight of methylene chloride was added to 50.0 parts by weight of 9,9-dipropylfluorene obtained in the same manner as in Synthesis Example 1 to dissolve 9,9-dipropylfluorene. After that, the solution was cooled with ice and 39.9 parts by weight of aluminum chloride was added to the solution. After that, 16.0 parts by weight of acetyl chloride was dropped to the mixture and the whole was stirred for 2 hours. 79.9 Parts by weight of aluminum chloride and 55.6 parts by weight of 4-nitrobenzoyl chloride were added to the resultant, and the mixture was warmed to 40° C. and stirred for 5 hours. After the reaction liquid had been cooled, the liquid was injected into ice water to be subjected to liquid separation. After that, an oil layer was washed with water twice and the oil layer was concentrated. The resultant solid was suspended in methanol and filtered to provide 61.0 parts by weight (yield: 69%, HPLC purity: 89%) of a compound D-7A.

500 Parts by weight of ethanol, 31.5 parts by weight of hydroxylamine hydrochloride, and 37.2 parts by weight of anhydrous sodium acetate were added to 50 parts by weight of the compound D-7A, and the mixture was warmed to 40° C. and stirred for 2 hours. The reaction liquid was cooled with ice and the precipitated crystal was filtered to provide 51.7 parts by weight (yield: 100%, HPLC purity: 80%) of a compound D-7B.

500 Parts by weight of ethyl acetate was added to 50 parts by weight of the compound D-7B to dissolve the compound. After that, 33.5 parts by weight of acetic anhydride was added to the solution and the mixture was stirred at room temperature for 5 hours. Water was added to subject the mixture to liquid separation, and an oil layer was washed with 5% sodium bicarbonate water and water. The oil layer was concentrated and recrystallized with methanol to provide 12.2 parts by weight (yield: 22%, HPLC purity: 98%) of the compound D-7. The structure of the resultant compound D-7 was confirmed by a $^1$H-NMR spectrum (CDCl$_3$). The $^1$H-NMR spectrum is described below.

δ [ppm]: 8.37 (d: 2H), 7.96 (d: 2H), 7.89 (s: 1H), 7.73-7.84 (m: 5H), 2.47 (s: 3H), 2.30 (s: 3H), 2.00-2.07 (m: 4H), 0.60-0.72 (m: 10H)

Synthesis Example D-8

Synthesis of Compound D-8

The compound D-8 was synthesized in the same manner as in Synthesis Example D-7 except that acetyl chloride was changed to 2-methylpropionyl chloride. The resultant compound D-8 had a yield of 33% and a HPLC purity of 98%. The structure of the resultant compound was confirmed by a $^1$H-NMR spectrum (CDCl$_3$). The $^1$H-NMR spectrum is described below.

δ [ppm]: 8.35-8.42 (m: 2H), 7.70-8.00 (m: 6H), 7.43-7.50 (m: 1H), 7.18-7.23 (m: 1H), 3.60 (sep: 0.5H, isomer), 3.08 (sep: 0.5H, isomer), 2.28 (s: 1.5H, isomer), 1.97-2.10 (m: 4H), 1.94 (s: 1.5H, isomer), 1.20-1.30 (m: 6H), 0.60-0.75 (m: 10H)

Synthesis Example D-9

Synthesis of Compound D-9

A fluorene-based compound (the compound D-9) was synthesized by the following synthesis method.

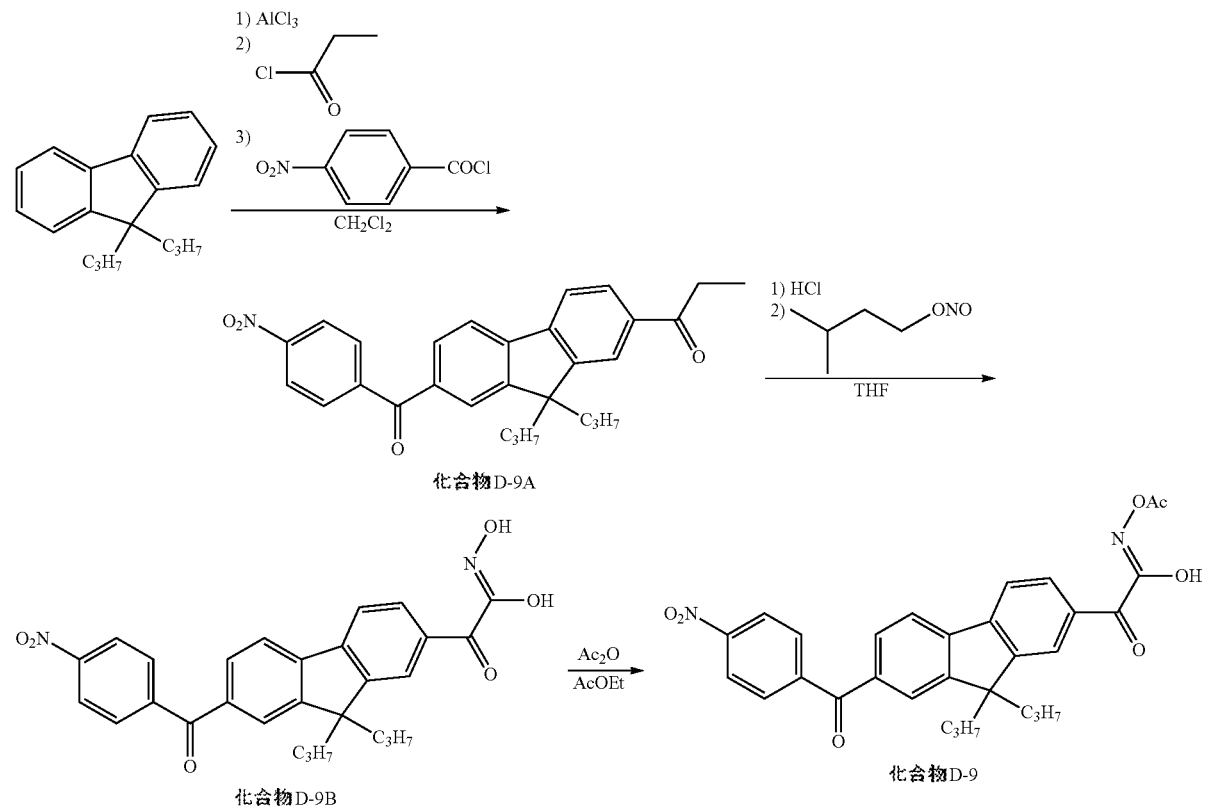

200 Parts by weight of methylene chloride and 16.0 parts by weight of anhydrous aluminum chloride were added to 20.0 parts by weight of 9,9-dipropylfluorene obtained in the same manner as in Synthesis Example 1. After that, 7.5 parts by weight of propionyl chloride was added to the mixture and the whole was stirred at room temperature for 2 hours. 32.0 Parts by weight of aluminum chloride and 22.2 parts by weight of 4-nitrobenzoyl chloride were added to the resultant, and the mixture was warmed to 40° C. and stirred for 5 hours. After the reaction liquid had been cooled, the liquid was injected into ice water to be subjected to liquid separation. After that, an oil layer was washed with water twice and the oil layer was concentrated. The resultant solid was suspended in methanol and filtered to provide 29.1 parts by weight (yield: 80%, HPLC purity: 95%) of a compound D-9A.

250 Parts by weight of tetrahydrofuran, 85.8 parts by weight of concentrated hydrochloric acid, and 19.3 parts by weight of isoamyl nitrite were added to 25 parts by weight of the compound D-9A, and the mixture was stirred at room temperature for 12 hours. The reaction liquid was injected into water and ethyl acetate was added to subject the liquid to liquid separation. After an oil layer had been washed with water twice, the oil layer was concentrated to provide yellow oily matter. The oily matter was isolated and purified by silica gel column chromatography to provide 16.0 parts by weight (yield: 60%, HPLC purity: 95%) of a compound D-9B.

150 Parts by weight of ethyl acetate was added to 15 parts by weight of the compound D-9B to dissolve the compound. After that, 9.5 parts by weight of acetic anhydride was added to the solution and the mixture was stirred at room temperature for 24 hours. Water was added to subject the mixture to liquid separation, and an oil layer was washed with 5% sodium bicarbonate water and water. The oil layer was concentrated to provide 14.7 parts by weight (yield: 90%, HPLC purity: 98%) of the compound D-9. The structure of the resultant compound D-9 was confirmed by a $^1$H-NMR spectrum (CDCl$_3$). The $^1$H-NMR spectrum is described below.

δ [ppm]: 8.37 (d: 2H), 8.25-8.20 (m: 2H), 7.97 (d: 2H), 7.88 (t: 3H), 7.77 (dd: 1H), 2.35 (s: 3H), 2.30 (s: 3H), 1.98-2.22 (m: 4H), 0.62-0.74 (m: 10H)

Synthesis Example D-10

Synthesis of Compound D-10

A fluorene-based compound (the compound D-10) was synthesized by the following synthesis method.

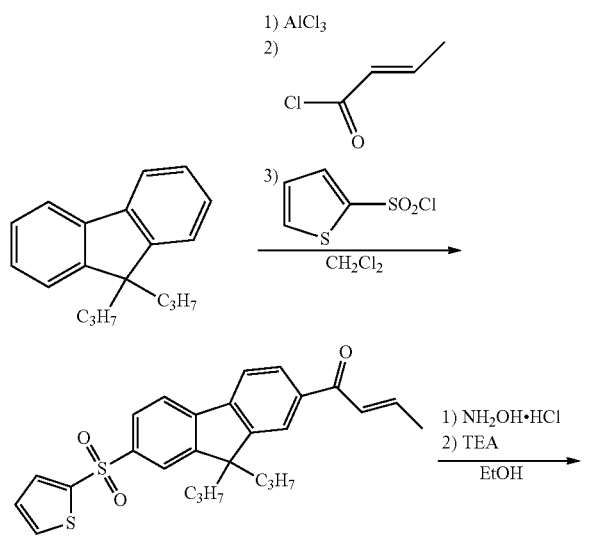

化合物D-10A

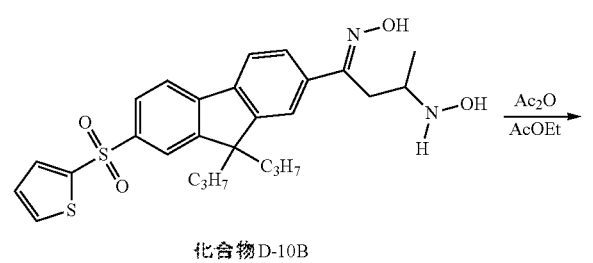

化合物D-10B

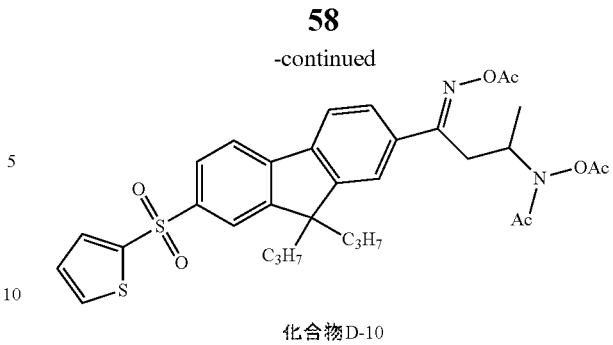

化合物D-10

500 Parts by weight of methylene chloride and 39.9 parts by weight of anhydrous aluminum chloride were added to 50.0 parts by weight of 9,9-dipropylfluorene obtained in the same manner as in Synthesis Example 1. After that, 21.3 parts by weight of crotonoyl chloride was added to the mixture and the whole was stirred at room temperature for 2 hours. 39.9 Parts by weight of anhydrous aluminum chloride and 54.7 parts by weight of 2-thiophenesulfonyl chloride were added to the resultant, and the mixture was stirred at room temperature for 24 hours. The reaction liquid was injected into ice water to be subjected to liquid separation. After that, an oil layer was washed with water twice and the oil layer was concentrated. The resultant solid was suspended in methanol and filtered to provide 15.8 parts by weight (yield: 17%, HPLC purity: 90%) of a compound D-10A.

150 Parts by weight of ethanol, 5.6 parts by weight of hydroxylamine hydrochloride, and 6.6 parts by weight of triethylamine were added to 15 parts by weight of the compound D-10A, and the mixture was heated to 78° C. and stirred for 5 hours. The reaction liquid was cooled to room temperature and then dropped into water. The precipitated crystal was filtered to provide 16.2 parts by weight (yield: 98%, HPLC purity: 96%) of a compound D-10B.

150 Parts by weight of ethyl acetate was added to 15 parts by weight of the compound D-10B to dissolve the compound. After that, 20.9 parts by weight of acetic anhydride was added to the solution and the mixture was warmed to 35° C. and stirred for 5 hours. Water was added to subject the mixture to liquid separation, and an oil layer was washed with 5% sodium bicarbonate water and water. The oil layer was concentrated and recrystallized with methanol to provide 15.5 parts by weight (yield: 83%, HPLC purity: 97%) of the compound D-10. The structure of the resultant compound D-10 was confirmed by a $^1$H-NMR spectrum (CDCl$_3$). The $^1$H-NMR spectrum is described below.

δ [ppm]: 8.02 (d: 1H), 7.93-7.98 (m: 1H), 7.84-7.77 (m: 4H), 7.72 (dd: 1H), 7.64 (dd: 1H), 7.08-7.11 (m: 1H), 4.84 (brs: 1H), 3.15-3.30 (m: 2H), 2.33 (s: 3H), 2.24 (s: 3H), 1.95-2.10 (m: 4H), 1.80 (s: 3H), 1.13-1.24 (m: 3H), 0.50-0.72 (m: 10H)

Synthesis Example D-11

Synthesis of Compound D-11

A fluorene-based compound (the compound D-11) was synthesized by the following synthesis method.

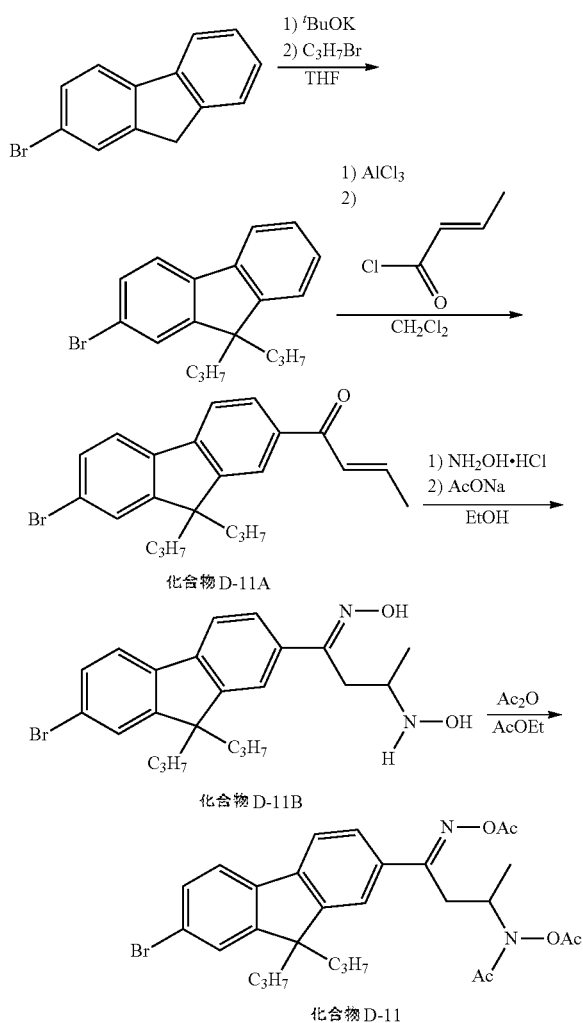

化合物 D-11A

化合物 D-11B

化合物 D-11

500.0 Parts by weight of tetrahydrofuran and 68.7 parts by weight of potassium tert-butoxide were loaded into a reaction vessel, and 50.0 parts by weight of 2-bromofluorene was added to the mixture. Next, 56.1 parts by weight of propyl bromide was dropped to the reaction vessel. The liquid was heated to 40° C. and stirred for 3 hours. After the reaction liquid had been cooled to room temperature, ethyl acetate and water were injected to subject the liquid to liquid separation, and an oil layer was washed with water twice. The oil layer was concentrated to provide 67.2 parts by weight (yield: 100%, HPLC purity: 92%) of 2-bromo-9,9-dipropylfluorene.

50.0 Parts by weight of 2-bromo-9,9-dipropylfluorene thus obtained, 500.0 parts by weight of methylene chloride, and 30.4 parts by weight of anhydrous aluminum chloride were loaded into a reaction vessel, and the mixture was cooled to 0° C. 20.6 Parts by weight of crotonoyl chloride was dropped to the mixture, and the whole was warmed to room temperature and stirred for 4 hours. The reaction liquid was injected into ice water to be subjected to liquid separation, and an oil layer was washed with 5% sodium bicarbonate water and water. The oil layer was concentrated, and was isolated and purified by silica gel column chromatography to provide 15.1 parts by weight (yield: 25%, HPLC purity: 80%) of a compound D-11A.

150.0 Parts by weight of ethanol, 10.5 parts by weight of hydroxylamine hydrochloride, and 12.4 parts by weight of anhydrous sodium acetate were added to 15.0 parts by weight of the resultant compound D-11A, and the mixture was heated to 40° C. and stirred for 5 hours. The reaction liquid was cooled to room temperature, water and ethyl acetate were injected to subject the liquid to liquid separation, and an oil layer was washed with water and dilute hydrochloric acid. The oil layer was concentrated to provide 10.9 parts by weight (yield: 65%, HPLC purity: 83%) of a compound D-11B.

100.0 Parts by weight of ethyl acetate and 18.3 parts by weight of acetic anhydride were added to 10.0 parts by weight of the resultant compound D-11B, and the mixture was warmed to 40° C. and stirred for 5 hours. After the reaction liquid had been cooled to room temperature, water was added to subject the liquid to liquid separation, and an oil layer was washed with water and 5% sodium bicarbonate water, followed by its concentration. The resultant solid was isolated and purified by silica gel column chromatography to provide 7.1 parts by weight (yield: 55%, HPLC purity: 96%) of the compound D-11. The structure of the resultant compound D-11 was confirmed by a $^1$H-NMR spectrum (CDCl$_3$). The $^1$H-NMR spectrum is described below.

δ [ppm]: 7.67-7.78 (m: 3H), 7.58 (d: 1H), 7.45-7.50 (m: 2H), 4.82 (brs: 1H), 3.14-3.32 (m: 2H), 2.32 (s: 3H), 2.24 (s: 3H), 1.92-2.30 (m: 4H), 1.89 (s: 3H), 1.2 (d: 3H), 0.55-0.72 (m: 10H)

Synthesis Example D-12

Synthesis of Compound D-12

A fluorene-based compound (the compound D-12) was synthesized by the following synthesis method.

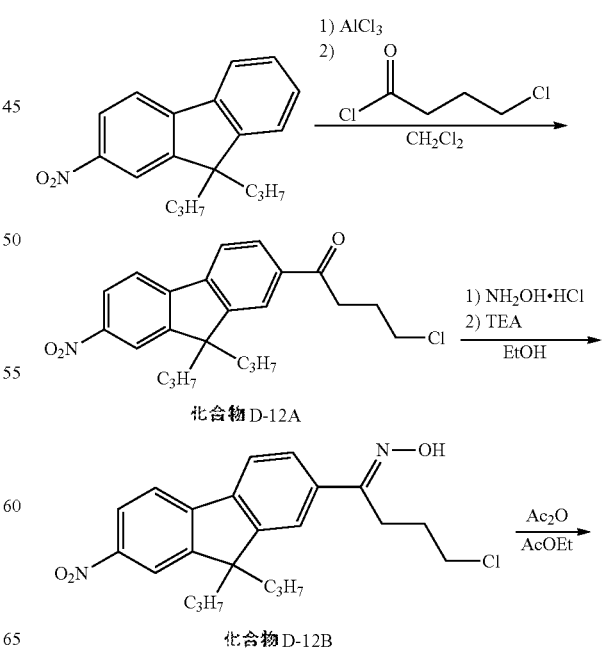

化合物 D-12A

化合物 D-12B

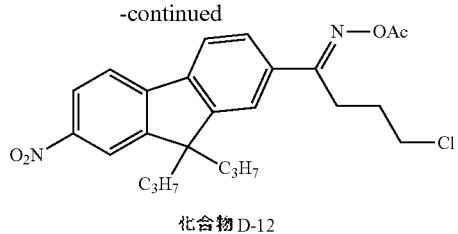

化合物 D-12

500 Parts by weight of methylene chloride and 45.1 parts by weight of anhydrous aluminum chloride were added to 50.0 parts by weight of 2-nitro-9,9-dipropylfluorene obtained in the same manner as in Synthesis Example D-3. After that, 47.7 parts by weight of 4-chlorobutyryl chloride was added to the mixture and the whole was stirred at room temperature for 2 hours. The reaction liquid was injected into ice water to be subjected to liquid separation, and then an oil layer was washed with water twice and concentrated. The resultant solid was suspended in methanol and filtered to provide 50.8 parts by weight (yield: 100%, HPLC purity: 98%) of a compound D-12A.

200 Parts by weight of ethanol, 8.7 parts by weight of hydroxylamine hydrochloride, and 10.3 parts by weight of triethylamine were added to 20.0 parts by weight of the compound D-12A, and the mixture was stirred at 60° C. for 3 hours. The reaction liquid was injected into water, ethyl acetate was added to subject the liquid to liquid separation, and an oil layer was washed with water twice. After that, the oil layer was concentrated to dryness. The resultant solid was recrystallized with methanol to provide 25.6 parts by weight (yield: 100%, HPLC purity: 92%) of a compound D-12B.

250 Parts by weight of ethyl acetate was added to 25 parts by weight of the compound D-12B to dissolve the compound. After that, 18.5 parts by weight of acetic anhydride was added to the solution and the mixture was stirred at room temperature for 5 hours. Water was added to subject the mixture to liquid separation, and an oil layer was washed with 5% sodium bicarbonate water and water. A solid obtained by concentrating the oil layer was isolated and purified by silica gel column chromatography to provide 17.9 parts by weight (yield: 65%, HPLC purity: 98%) of the compound D-12. The structure of the resultant compound D-12 was confirmed by a $^1$H-NMR spectrum (CDCl$_3$). The $^1$H-NMR spectrum is described below.

δ [ppm]: 8.28 (dd: 1H), 8.23 (d: 1H), 7.79-7.86 (m: 4H), 3.62 (t: 2H), 3.12 (t: 2H), 2.31 (s: 3H), 2.01-2.14 (m: 6H), 0.56-0.72 (m: 10H)

Synthesis Example D-13

Synthesis of Compound D-13

A fluorene-based compound (the compound D-13) was synthesized by the following synthesis method.

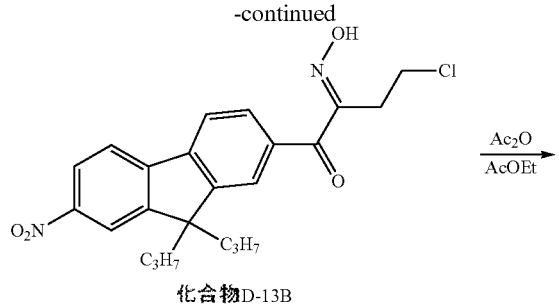

化合物 D-13B

化合物 D-13

200 Parts by weight of tetrahydrofuran, 78.1 parts by weight of concentrated hydrochloric acid, and 8.8 parts by weight of isoamyl nitrite were added to 20 parts by weight of the compound D-12A obtained in Synthesis Example D-12, and the mixture was stirred at room temperature for 5 hours. The reaction liquid was injected into water and ethyl acetate was added to subject the liquid to liquid separation. After an oil layer had been washed with water twice, the oil layer was concentrated to provide 20.8 parts by weight (yield: 97%, HPLC purity: 88%) of a compound D-13B.

200 Parts by weight of ethyl acetate was added to 20 parts by weight of the compound D-13B to dissolve the compound. After that, 14.8 parts by weight of acetic anhydride was added to the solution and the mixture was stirred at room temperature for 16 hours. Water was added to subject the mixture to liquid separation, and an oil layer was washed with 5% sodium bicarbonate water and water. The oil layer was concentrated, and the resultant oily matter was isolated and purified by silica gel column chromatography to provide 14.1 parts by weight (yield: 62%, HPLC purity: 98%) of the compound D-13. The structure of the resultant compound D-13 was confirmed by a $^1$H-NMR spectrum (CDCl$_3$). The $^1$H-NMR spectrum is described below.

δ [ppm]: 8.29 (dd: 1H), 8.25 (d: 1H), 8.17-8.21 (m: 2H), 7.88 (dd: 2H), 3.83 (t: 2H), 3.36-3.41 (m: 2H), 2.31 (s: 3H), 2.00-2.12 (m: 4H), 0.58-0.72 (m: 10H)

Synthesis Example D-14

Synthesis of Compound D-14

A fluorene-based compound (the compound D-14) was synthesized by the following synthesis method.

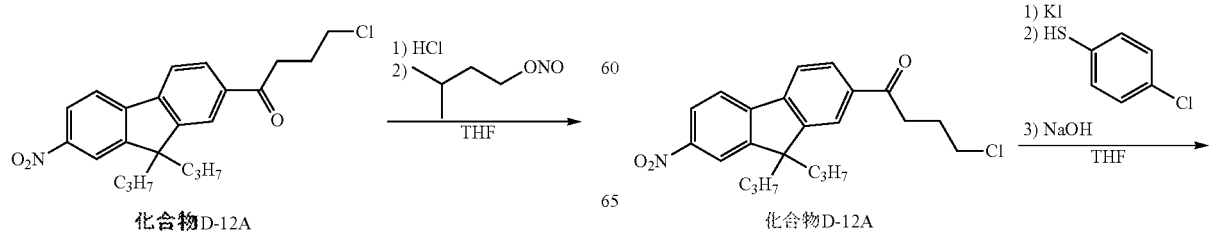

化合物 D-12A     化合物 D-12A

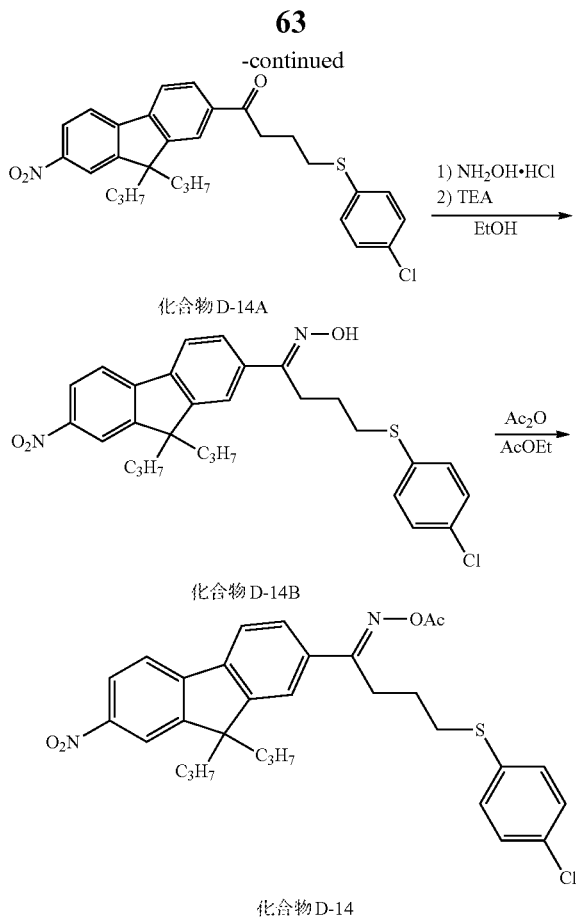

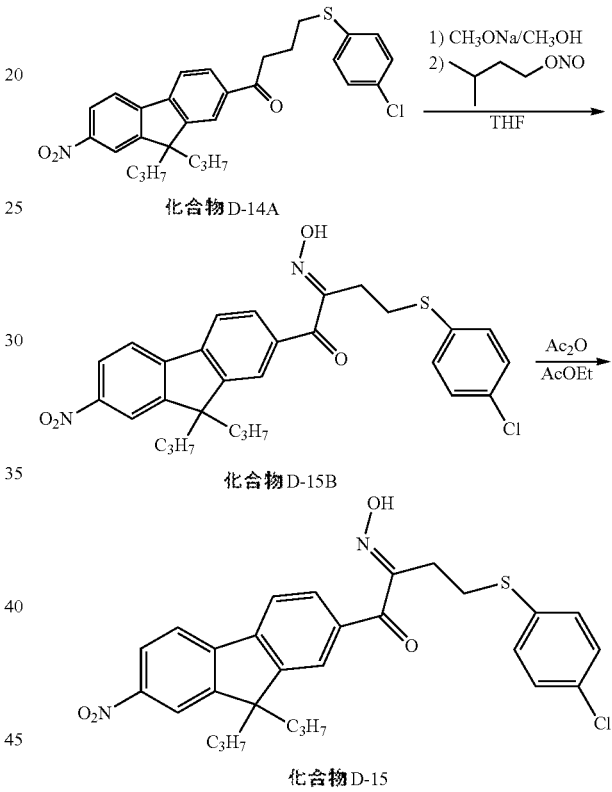

200 Parts by weight of tetrahydrofuran, 2.1 parts by weight of potassium iodide, and 7.6 parts by weight of 4-chlorobenzenethiol were added to 20 parts by weight of the compound D-12A obtained in Synthesis Example D-12, and 2.1 parts by weight of sodium hydroxide was added to the mixture while the mixture was stirred at room temperature. The mixed liquid was warmed to 50° C. and stirred for 2 hours. After that, the mixed liquid was cooled to room temperature, and water and ethyl acetate were added to subject the liquid to liquid separation. After an oil layer had been washed with water and dilute hydrochloric acid, a product obtained by concentrating the oil layer was isolated and purified by silica gel column chromatography to provide 16.0 parts by weight (yield: 63%, HPLC purity: 93.8%) of a compound D-14A.

150 Parts by weight of ethanol, 5.1 parts by weight of hydroxylamine hydrochloride, and 6.1 parts by weight of triethylamine were added to 15 parts by weight of the compound D-14A, and the mixture was warmed to 60° C. and stirred for 10 hours. After that, the mixture was cooled to room temperature. Water and ethyl acetate were added to the reaction liquid to subject the liquid to liquid separation. After an oil layer had been washed with water twice, the oil layer was concentrated to provide 15.4 parts by weight (yield: 100%, HPLC purity: 87%) of a compound D-14B.

150 Parts by weight of ethyl acetate and 8.8 parts by weight of acetic anhydride were added to 15 parts by weight of the compound D-14B, and the mixture was stirred at room temperature for 5 hours. Water was added to subject the liquid to liquid separation, and an oil layer was washed with 5% sodium bicarbonate water and water, followed by its concentration. The resultant solid was isolated and purified by silica gel column chromatography to provide 10.5 parts by weight (yield: 65%, HPLC purity: 98%) of the compound D-14. The structure of the resultant compound D-14 was confirmed by a $^1$H-NMR spectrum (CDCl$_3$). The $^1$H-NMR spectrum is described below.

δ [ppm]: 8.29 (dd: 1H), 8.22 (d: 1H), 7.71-7.85 (m: 4H), 7.20-7.27 (m: 4H), 3.07 (t: 2H), 2.98 (t: 2H), 2.27 (s: 3H), 1.85-2.08 (m: 6H), 0.55-0.72 (m: 10H)

Synthesis Example D-15

Synthesis of Compound D-15

A fluorene-based compound (the compound D-15) was synthesized by the following synthesis method.

200 Parts by weight of tetrahydrofuran, 9.5 parts by weight of a 28% solution of sodium methoxide in methanol, and 5.8 parts by weight of isoamyl nitrite were added to 20 parts by weight of the compound D-14A obtained in Synthesis Example D-14, and the mixture was stirred at room temperature for 2 hours. The reaction liquid was injected into water and ethyl acetate was added to subject the liquid to liquid separation. After an oil layer had been washed with water twice, the oil layer was concentrated to provide 17.3 parts by weight (yield: 82%, HPLC purity: 65%) of a compound D-15B.

150 Parts by weight of ethyl acetate was added to 15 parts by weight of the compound D-15B to dissolve the compound. After that, 8.6 parts by weight of acetic anhydride was added to the solution and the mixture was stirred at room temperature for 4 hours. Water was added to subject the mixture to liquid separation, and an oil layer was washed with 5% sodium bicarbonate water and water. The oil layer was concentrated, and the resultant oily matter was isolated and purified by silica gel column chromatography to provide 5.7 parts by weight (yield: 36%, HPLC purity: 100%) of the compound D-15. The structure of the resultant compound D-15 was confirmed by a $^1$H-NMR spectrum (CDCl$_3$). The $^1$H-NMR spectrum is described below.

δ [ppm]: 8.29 (dd: 1H), 8.25 (d: 1H), 8.16-8.21 (m: 2H), 7.88 (dd: 2H), 7.30 (d: 4H), 3.25 (m: 4H), 2.21 (s: 3H), 2.00-2.12 (m: 4H), 0.58-0.72 (m: 10H)

Synthesis Example D-16

Synthesis of Compound D-16

The compound D-16 was synthesized in the same manner as in Synthesis Example 4 except that propyl bromide was changed to benzyl bromide. The resultant compound D-16 had a yield of 10% and a HPLC purity of 98%. The structure of the resultant compound was confirmed by a $^1$H-NMR spectrum (CDCl$_3$). The $^1$H-NMR spectrum is described below.

δ [ppm]: 7.93 (s: 1H), 7.75 (d: 1H), 7.70 (s: 1H), 7.60 (d: 1H), 7.40-7.50 (m: 3H), 7.28-7.35 (m: 3H), 6.85-7.00 (m: 6H), 6.40 (d: 4H), 3.40 (q: 4H), 2.42 (s: 3H), 2.34 (s: 3H), 2.31 (s: 3H)

Synthesis Example D-17

Synthesis of Compound D-17

A fluorene-based compound (the compound D-17) was synthesized by the following synthesis method.

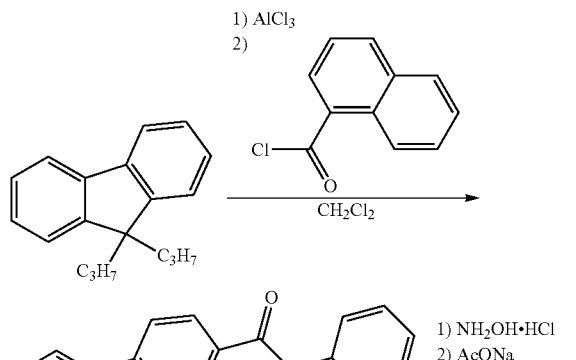

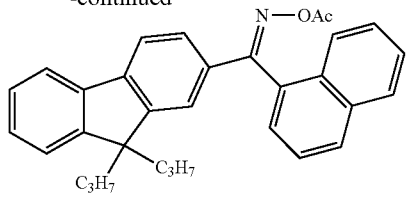

化合物 D-17

200 Parts by weight of methylene chloride and 12.8 parts by weight of anhydrous aluminum chloride were added to 20.0 parts by weight of 9,9-dipropylfluorene obtained in the same manner as in Synthesis Example 1. After that, 18.3 parts by weight of 1-naphthoyl chloride was added to the solution, and the mixture was stirred at room temperature for 2 hours. The reaction liquid was injected into ice water to be subjected to liquid separation. After that, an oil layer was washed with water twice and the oil layer was concentrated. The resultant solid was suspended in methanol and filtered to provide 35.9 parts by weight (yield: 100%, HPLC purity: 98%) of a compound D-17A.

300 Parts by weight of ethanol, 37.1 parts by weight of hydroxylamine hydrochloride, and 43.8 parts by weight of anhydrous sodium acetate were added to 30.0 parts by weight of the compound D-17A, and the mixture was stirred at 78° C. for 24 hours. After the reaction liquid had been cooled, the reaction liquid was injected into water and ethyl acetate was added to subject the liquid to liquid separation. After an oil layer had been washed with water twice, the oil layer was concentrated. The resultant solid was recrystallized with methanol to provide 25.0 parts by weight (yield: 81%, HPLC purity: 98%) of a compound D-17B.

200 Parts by weight of ethyl acetate was added to 20 parts by weight of the compound D-17B to dissolve the compound. After that, 13.2 parts by weight of acetic anhydride was added to the solution, and the mixture was stirred at room temperature for 6 hours. Water was added to subject the mixture to liquid separation, and an oil layer was washed with 5% sodium bicarbonate water and water. A solid obtained by concentrating the oil layer was recrystallized with methanol to provide 17.6 parts by weight (yield: 81%, HPLC purity: 97%) of the compound D-17. The structure of the resultant compound D-17 was confirmed by a $^1$H-NMR spectrum (CDCl$_3$). The $^1$H-NMR spectrum is described below.

δ [ppm]: 7.96 (q: 2H), 7.81 (s: 1H), 7.28-7.70 (m: 11H), 1.85-2.00 (m: 7H), 0.62 (d: 10H)

Synthesis Example D-18

Synthesis of Compound D-18

A fluorene-based compound (the compound D-18) was synthesized by the following synthesis method.

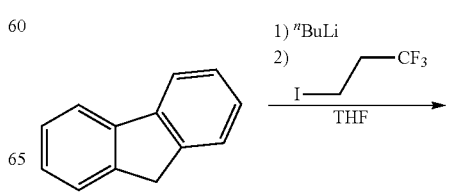

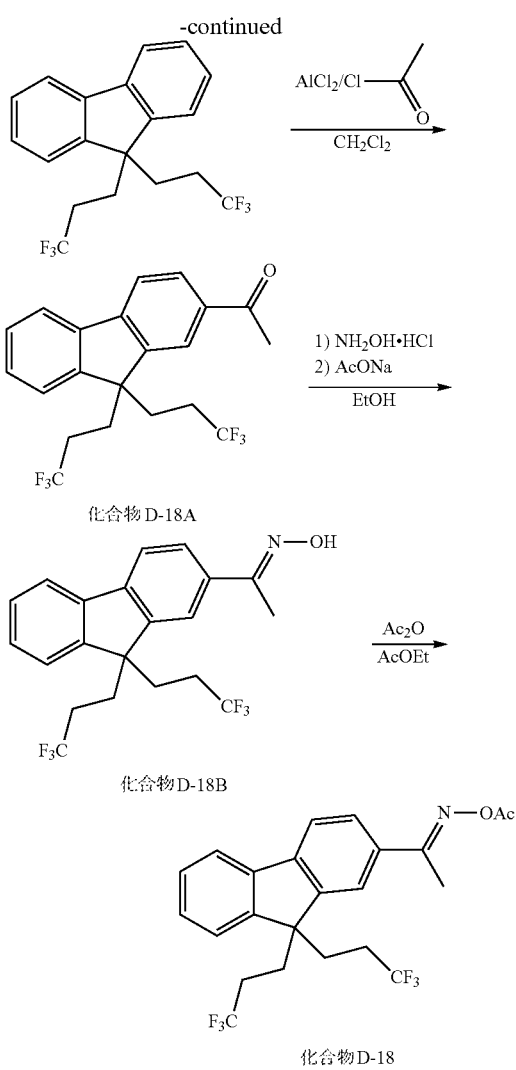

化合物 D-18A

化合物 D-18B

化合物 D-18

25.0 Parts by weight of fluorene and 300.0 parts by weight of anhydrous tetrahydrofuran were loaded into a reaction vessel, and air in the reaction vessel was replaced with a nitrogen gas. After that, the mixture was cooled to −20° C. 59.7 Parts by weight of normal butyllithium (1.6 M hexane solution) was added to the mixture and the whole was slowly warmed to room temperature, followed by stirring for 1 hour. The reaction liquid was cooled to −78° C. and 31.0 parts by weight of 1,1,1-trifluoro-3-iodopropane was added to the liquid. The mixture was slowly warmed to room temperature and then stirred for 1 hour. The mixture was cooled to −78° C. again and 59.7 parts by weight of normal butyllithium (1.6 M hexane solution) was added to the mixture. The resultant was warmed to room temperature and then stirred for 1 hour. The resultant was further cooled to −78° C. and 31.0 parts by weight of 1,1,1-trifluoro-3-iodopropane was added to the resultant. The mixture was warmed to room temperature and stirred for 1 hour. After 90% acetic acid had been added to the reaction liquid, a saturated saline solution and hexane were added to subject the liquid to liquid separation. An oil layer was washed with water and concentrated. The resultant solid was isolated and purified by silica gel column chromatography to provide 28.5 parts by weight (yield: 66%, HPLC purity: 98%) of 9,9-bis(3,3,3-trifluoropropyl)-9H-fluorene.

250 Parts by weight of methylene chloride was added to 14.0 parts by weight of anhydrous aluminum chloride, and 6.6 parts by weight of acetyl chloride was added to the mixture while the mixture was stirred, followed by cooling with ice. A solution prepared by dissolving 25.0 parts by weight of 9,9-bis(3,3,3-trifluoropropyl)-9H-fluorene in 25.0 parts by weight of methylene chloride was added to the mixed liquid, and the whole was warmed to room temperature and stirred for 1 hour. The reaction liquid was injected into ice water to be subjected to liquid separation. After that, an oil layer was washed with water twice and the oil layer was concentrated. The resultant solid was recrystallized with methanol to provide 25.9 parts by weight (yield: 93%, HPLC purity: 98%) of a compound D-18A.

250 Parts by weight of ethanol, 17.4 parts by weight of hydroxylamine hydrochloride, and 20.5 parts by weight of anhydrous sodium acetate were added to 25.0 parts by weight of the compound D-18A, and the mixture was warmed to 40° C. and stirred for 6 hours. Water was injected into the reaction liquid and then the precipitated crystal was filtered to provide 25.2 parts by weight (yield: 97%, HPLC purity: 99%) of a compound D-18B.

200 Parts by weight of ethyl acetate and 14.7 parts by weight of acetic anhydride were added to 20.0 parts by weight of the compound D-18B, and the mixture was stirred at room temperature for 24 hours. Water was added to subject the mixture to liquid separation and an oil layer was washed with water. After that, the oil layer was concentrated. The resultant solid was recrystallized with methanol to provide 21.6 parts by weight (yield: 98%, HPLC purity: 99%) of the compound D-18. The structure of the resultant compound D-18 was confirmed by a $^1$H-NMR spectrum (CDCl$_3$). The $^1$H-NMR spectrum is described below.

δ [ppm]: 7.72-7.86 (m: 4H), 7.36-7.47 (m: 3H), 2.46 (s: 3H), 2.22-2.39 (m: 7H), 1.16-1.40 (m: 4H)

Synthesis Example D-19

Synthesis of Compound D-19

A fluorene-based compound (the compound D-19) was synthesized by the following synthesis method.

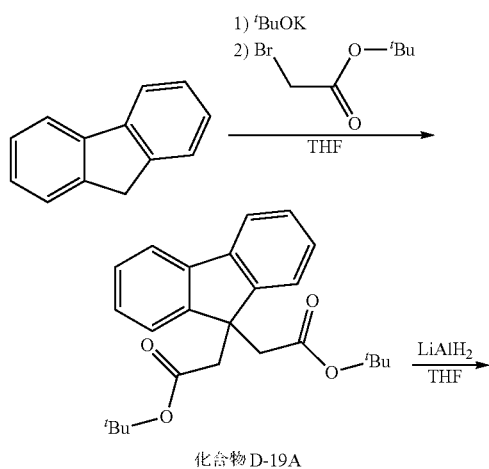

化合物 D-19A

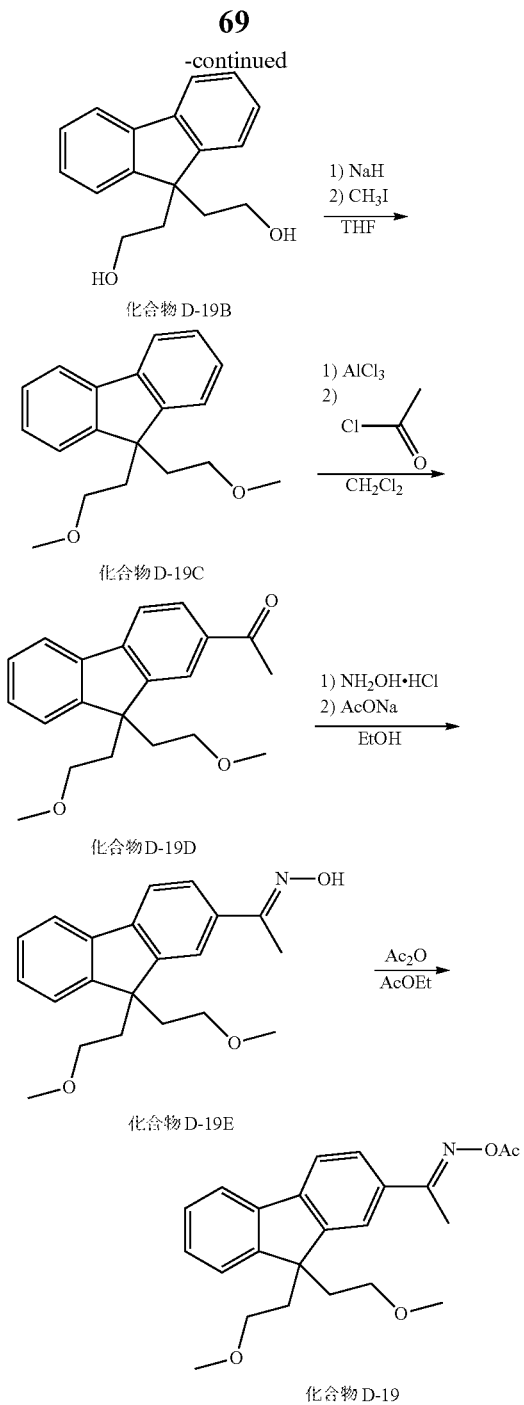

60.8 Parts by weight of potassium tert-butoxide and 300 parts by weight of tetrahydrofuran were loaded into a reaction vessel, and the mixture was cooled to 0° C. A solution prepared by dissolving 30 parts by weight of fluorene in 90 parts by weight of tetrahydrofuran was dropped to the potassium tert-butoxide solution. After the mixture had been stirred at 0° C. for 10 minutes, 105.6 parts by weight of tert-butyl bromoacetate was dropped to the mixture and the whole was stirred at 0° C. for 1 hour. After that, the resultant was warmed to room temperature and further stirred for 1 hour. Ethyl acetate and water were added to subject the resultant to liquid separation, and then an oil layer was concentrated to provide 71.2 parts by weight (yield: 100%, HPLC purity: 93%) of a compound D-19A.

13.0 Parts by weight of lithium aluminum hydride was added to 500 parts by weight of tetrahydrofuran and the mixture was cooled to 0° C. 70 Parts by weight of the compound D-19A dissolved in 100 parts by weight of tetrahydrofuran was dropped to the mixture. The resultant was warmed to room temperature and stirred for 1 hour. After that, the resultant was warmed to 40° C. and further stirred for 1 hour. After the reaction liquid had been cooled to room temperature, a saturated aqueous solution of Rochelle salt was added to quench the liquid, and the mixture was subjected to liquid separation. After that, an oil layer was washed with dilute hydrochloric acid and then concentrated to provide 29.8 parts by weight (yield: 60%, HPLC purity: 98%) of a compound D-19B.

25.0 Parts by weight of the compound D-19B was dissolved in 200 parts by weight of tetrahydrofuran, and the solution was cooled to 0° C. After that, 9.8 parts by weight of sodium hydride (60% oil dispersion) was added to the solution and the mixture was stirred for 10 minutes. 30.7 Parts by weight of methyl iodide was added to the mixture, and the whole was warmed to room temperature and stirred for 1 hour. After 90% acetic acid had been added to the resultant, ethyl acetate and water were added to subject the resultant to liquid separation, and an oil layer was washed with a saturated saline solution and then concentrated. The resultant solid was recrystallized with methanol to provide 27.8 parts by weight (yield: 100%, HPLC purity: 100%) of a compound D-19C.

250 Parts by weight of methylene chloride was added to 17.7 parts by weight of anhydrous aluminum chloride, and 8.3 parts by weight of acetyl chloride was added to the mixture, followed by cooling with ice. A solution prepared by dissolving 25.0 parts by weight of the compound D-19C in 25.0 parts by weight of methylene chloride was added to the mixed liquid, and the whole was warmed to room temperature and stirred for 1 hour. The reaction liquid was injected into ice water to be subjected to liquid separation, and an oil layer was washed with water twice and concentrated. The resultant solid was recrystallized with methanol to provide 22.4 parts by weight (yield: 78%, HPLC purity: 98%) of a compound D-19D.

200 Parts by weight of ethanol, 17.1 parts by weight of hydroxylamine hydrochloride, and 20.2 parts by weight of anhydrous sodium acetate were added to 20.0 parts by weight of the compound D-19D, and the mixture was warmed to 40° C. and stirred for 24 hours. Water was injected into the reaction liquid and then the precipitated crystal was filtered to provide 19.4 parts by weight (yield: 93%, HPLC purity: 99%) of a compound D-19E.

150 Parts by weight of ethyl acetate and 13.5 parts by weight of acetic anhydride were added to 15.0 parts by weight of the compound D-19E, and the mixture was stirred at room temperature for 3 hours. Water was added to subject the mixture to liquid separation, and an oil layer was washed with water. After that, the oil layer was concentrated. The resultant solid was recrystallized with methanol to provide 12.4 parts by weight (yield: 74%, HPLC purity: 100%) of the compound D-19. The structure of the resultant compound D-19 was confirmed by a $^1$H-NMR spectrum (CDCl$_3$). The $^1$H-NMR spectrum is described below.

δ [ppm]: 7.68-7.85 (m: 4H), 7.33-7.50 (m: 3H), 3.00 (s: 6H), 2.66 (q: 4H), 2.45 (s: 3H), 2.38 (q: 4H), 2.28 (s: 3H)

Synthesis Example D-20

Synthesis of Compound D-20

The compound D-20 was synthesized in the same manner as in Synthesis Example 1 except that acetic anhydride was changed to benzoyl chloride. The resultant compound D-20 had a yield of 30% and a HPLC purity of 98%. The structure of the resultant compound was confirmed by a ¹H-NMR spectrum (CDCl₃). The ¹H-NMR spectrum is described below.

δ [ppm]: 8.25 (d: 2H), 7.99 (d: 1H), 7.82 (d: 1H), 7.74 (d: 1H), 7.69 (dd: 2H), 7.33-7.55 (m: 7H), 7.23 (d: 1H), 2.21 (s: 3H), 2.00-2.12 (m: 4H), 0.54-0.74 (m: 10H)

Synthesis Example D-21

Synthesis of Compound D-21

The compound D-21 was synthesized in the same manner as in Synthesis Example 1 except that acetic anhydride was changed to 3-(methylthio) propionyl chloride. The resultant compound D-21 had a yield of 25% and a HPLC purity of 98%. The structure of the resultant compound was confirmed by a ¹H-NMR spectrum (CDCl₃). The ¹H-NMR spectrum is described below.

δ [ppm]: 8.21-8.28 (m: 2H), 7.86 (s: 1H), 7.81 (d: 1H), 7.73 (d: 1H), 7.29-7.45 (m: 4H), 7.14 (d: 1H), 2.58-2.69 (m: 4H), 2.17 (s: 3H), 1.98-2.07 (m: 7H), 0.55-0.71 (m: 10H)

Synthesis Example D-22

Synthesis of Compound D-22

The compound D-22 was synthesized in the same manner as in Synthesis Example 1 except that acetic anhydride was changed to thiophene-2-acetyl chloride. The resultant compound D-22 had a yield of 30% and a HPLC purity of 99%. The structure of the resultant compound was confirmed by a ¹H-NMR spectrum (CDCl₃). The ¹H-NMR spectrum is described below.

δ [ppm]: 8.25 (dd: 1H), 8.21 (d: 1H), 7.85 (d: 1H), 7.79 (d: 1H), 7.70 (d: 1H), 7.36-7.43 (m: 2H), 7.30 (d: 2H), 7.16 (dd: 1H), 7.08 (d: 1H), 6.88 (q: 1H), 6.73 (d: 1H), 3.82 (s: 2H), 2.07 (s: 3H), 2.01 (t: 4H), 0.52-0.70 (m: 10H)

Synthesis Example D-23

Synthesis of Compound D-23

The compound D-23 was synthesized in the same manner as in Synthesis Example 1 except that acetic anhydride was changed to cyclohexanecarbonyl chloride. The resultant compound D-23 had a yield of 30% and a HPLC purity of 97%.

Synthesis Example D-24

Synthesis of Compound D-24

The compound D-24 was synthesized in the same manner as in Synthesis Example 1 except that acetic anhydride was changed to 3-chloropropionyl chloride. The resultant compound D-24 had a yield of 30% and a HPLC purity of 98%.

Synthesis Example D-25

Synthesis of Compound D-25

The compound D-25 was synthesized in the same manner as in Synthesis Example 1 except that acetic anhydride was changed to methoxyacetyl chloride. The resultant compound D-25 had a yield of 30% and a HPLC purity of 98%.

Synthesis Example D-26

Synthesis of Compound D-26

The compound D-26 was synthesized in the same manner as in Synthesis Example 1 except that acetic anhydride was changed to phenylacetyl chloride. The resultant compound D-26 had a yield of 30% and a HPLC purity of 99%.

[Property Evaluation]

The fluorene-based compounds obtained in the foregoing synthesis examples were subjected to the property evaluations as described below. In addition, for comparison, photopolymerization initiators of Reference Example 1 and Reference Example 2 below were similarly subjected to the property evaluations. The results are shown in Table 1.

Reference Example 1

A compound C-1 represented by the following formula was used as a photopolymerization initiator.

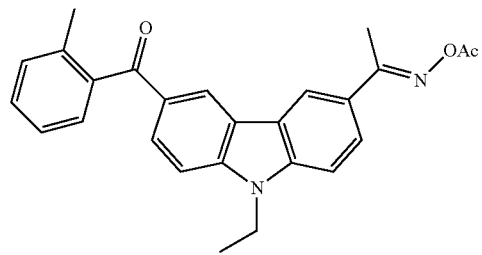 [SMILES: CCn1c2ccc(C(=O)c3ccccc3C)cc2c2cc(/C(C)=N/OC(C)=O)ccc21]

Reference Example 2

A compound C-2 represented by the following formula was used as a photopolymerization initiator.

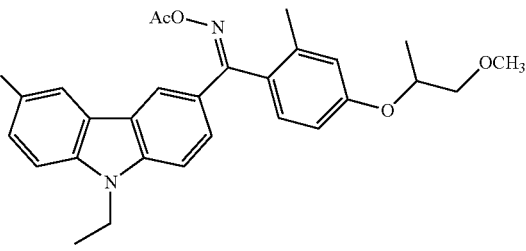

(Absorption Coefficient)

A 0.001% (wt/vol) solution of each of the compounds 1, 2, 4, 6, 8, 9, 11, 12, 13, 15, 16, D-1, D-3, D-4, D-7, D-8, D-9, D-12, D-14, D-15, D-20, C-1, and C-2 in tetrahydrofuran was prepared, and its absorbance was measured with a spectrophotometer (manufactured by Hitachi High-Technologies Corporation, trade name: "U-3900H"). An absorption maximum wavelength (λmax) at a wavelength of from 280 nm to 400 nm was read from an absorption spectrum obtained with the spectrophotometer.

(Melting Point and Decomposition Point)

The compounds 1, 2, 4, 6, 8, 9, 11, 12, 13, 15, 16, D-1, D-3, D-4, D-7, D-8, D-9, D-12, D-14, D-15, D-20, C-1, and C-2 were each subjected to measurement with a thermal analysis apparatus (TG-DTA) (manufactured by Rigaku Corporation, trade name: "Thermo Plus EVO TG 8120") by using 5.0 mg thereof.

(Solubility)

Each of the compounds 1, 4, 8, 15, 16, D-1, D-3, D-4, D-7, D-8, D-9, D-12, D-20, C-1, and C-2 was dissolved in 100 parts by weight of each of propylene glycol monomethyl ether (PGME), propylene glycol monomethyl ether acetate (PGMEA), and ethyl lactate at room temperature, and the amount of the photopolymerization initiator to be dissolved in each solvent was measured. An evaluation for solubility was performed in accordance with the following evaluation criteria based on the dissolution amount. It should be noted that the solubilities of the compounds 2, 9, 11, 12, 13, D-14, and D-15 were not measured because the resultant compounds were liquids.

A: 10 Parts by weight or more of the photopolymerization initiator is dissolved.

B: An amount in the range of from 5 parts by weight or more to less than 10 parts by weight of the photopolymerization initiator is dissolved.

C: An amount in the range of from 2 parts by weight or more to less than 5 parts by weight of the photopolymerization initiator is dissolved.

Figure 1B:
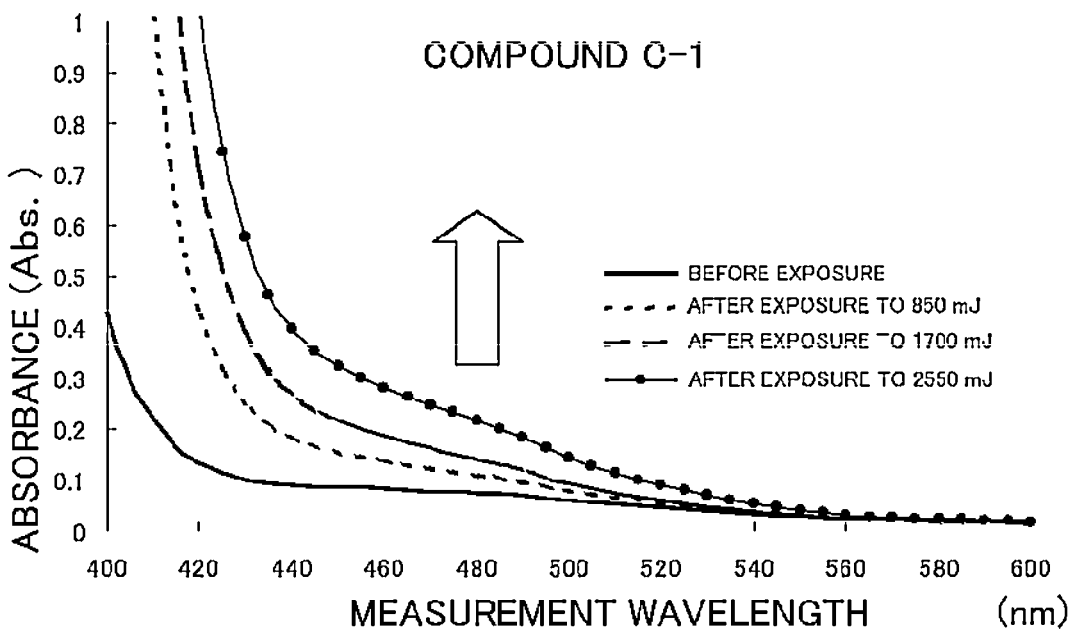
FIG. 1(B) is a graph for showing the results of the measurement of the degrees of coloring of a compound of Reference Example 1 before and after its exposure.

D: Less than 2 parts by weight of the photopolymerization initiator is dissolved.

exposure was measured with a spectrophotometer (manufactured by Hitachi High-Technologies Corporation, trade name: "U-3900H"). After that, the quartz surface of the UV cell was vertically irradiated with 850 mJ/cm$^2$ of UV light having a wavelength of 365 nm by using an exposure apparatus (manufactured by Ushio Inc., trade name: "MULTILIGHT" (ML-251A/B) and optical unit (PM25C-100)), and the absorption spectrum of the solution was measured again. The foregoing operations were repeatedly performed, and a change in absorbance of the solution by UV irradiation was measured. Further, the same experiment was performed by using the compound C-1 of Reference Example 1 instead of the compound 4 of Synthesis Example 4. FIG. 1(A) is a graph for showing the results of the measurement for the compound 4 and FIG. 1(B) is a graph for showing the results of the measurement for the compound C-1.

The axis of abscissa of the graph of FIG. 1(A) indicates the measurement wavelength (nm) of an absorption spectrum and the axis of ordinate thereof indicates an absorbance (Abs.) at the wavelength. The results of the measurement before UV irradiation are represented by a solid line, the results of the measurement after the irradiation with a total quantity of 850 mJ/cm$^2$ of UV light are represented by a dotted line, the results of the measurement after irradiation with a total quantity of 1,700 mJ/cm$^2$ of UV light are represented by a broken line, and the results of the mea-

TABLE 1

| Synthesis Example | Absorption coefficient at 365 nm [ml/(mg · cm)] | λ max nm | Absorption coefficient [ml/(mg · cm)] | Melting point (° C.) | Decomposition point (° C.) | Solubility PGME | PGMEA | Ethyl lactate |
|---|---|---|---|---|---|---|---|---|
| 1 | 45.2 | 347.0 | 63.4 | 146.9 | 225.9 | C | B | C |
| 2 | 37.3 | 347.5 | 51.3 | — | 229.9 | — | — | — |
| 4 | 2.2 | 330.5 | 85.7 | 146.5 | 277.0 | B | A | B |
| 6 | 1.9 | 330.0 | 71.7 | 97.1 | 212.1 | | No Data | |
| 8 | 3.3 | 329.5 | 69.7 | 121.7 | 246.1 | A | A | B |
| 9 | 3.0 | 330.0 | 54.0 | — | 192.7 | — | — | — |
| 11 | 6.6 | 333.5 | 55.0 | — | 257.3 | — | — | — |
| 12 | 11.8 | 335.5 | 43.0 | — | 195.2 | — | — | — |
| 13 | 9.2 | 338.5 | 36.3 | — | 167.1 | — | — | — |
| 15 | 0.0 | 315.0 | 70.0 | 154.8 | 280.0 | D | C | D |
| 16 | 0.1 | 296.5 | 97.7 | 106.6 | 240.9 | B | B | C |
| D-1 | 33.2 | 343.5 | 54.1 | 142.9 | 273.4 | D | C | D |
| D-3 | 46.3 | 345.5 | 67.8 | 155.9 | 272.2 | D | C | D |
| D-4 | 40.5 | 345.5 | 59.4 | 131.0 | 222.4 | B | A | B |
| D-7 | 21.9 | 341.5 | 62.9 | 181.8 | 250.3 | D | D | D |
| D-8 | 10.9 | 335.5 | 52.1 | 47.8 | 182.6 | A | A | A |
| D-9 | 29.1 | 343.0 | 63.7 | 120.4 | 228.9 | D | C | C |
| D-12 | 39.0 | 345.5 | 58.4 | 115.9 | 174.7 | A | A | B |
| D-14 | 36.3 | 345.5 | 53.9 | — | 186.9 | — | — | — |
| D-15 | 36.7 | 346.0 | 52.6 | — | 202.1 | — | — | — |
| D-20 | 44.8 | 348.0 | 61.1 | 187.4 | 242.1 | D | C | D |
| C-1 | 4.4 | 298.5 | 94.4 | 123.2 | 216.4 | B | B | C |
| C-2 | 26.8 | 369.0 | 27.2 | 135.7 | 264.0 | C | B | C |

(Transparency)

An influence on the coloring of a photopolymerization initiator after its exposure was confirmed because the photopolymerization initiator was required to have transparency. Specifically, as described below, the degrees of coloring (color change) of the photopolymerization initiator itself before and after its exposure were evaluated by measuring its absorbance. A 40 g/L solution of the compound 4 of Synthesis Example 4 in tetrahydrofuran was prepared, and the solution was loaded into a lidded UV cell made of quartz (12.5×12.5×58 mm) having an optical path length of 1 cm. The absorption spectrum of the solution before its surement after irradiation with a total quantity of 2,550 mJ/cm$^2$ of UV light are represented by a solid line with dots. The same holds true for the graph of FIG. 1(B). Comparison between the results of the measurement shown in FIG. 1(A) and the results of the measurement shown in FIG. 1(B) revealed that the degree to which the absorbance of the compound 4 increased after its exposure as compared with that before the exposure was lower than the degree to which the absorbance of the compound C-1 increased after its exposure as compared with that before the exposure. Therefore, it was shown that the influence on the coloring of the compound 4 by the exposure was small.

Evaluation of Transparent Photosensitive Composition

Example 1

0.192 Part by weight (0.4 mmol) of the fluorene-based compound (compound 1) obtained in Synthesis Example 1, 13.2 parts by weight of an acid group-containing acrylate (manufactured by Daicel-Allnex Ltd., trade name: "CYCLOMER P(ACA) 200M", its solid content had been adjusted to 20 wt % with PGMEA), 0.40 part by weight of dipentaerythritol hexaacrylate (manufactured by Nippon Kayaku Co., Ltd., trade name: "KAYARAD DPHA"), and 6.0 parts by weight of PGMEA were stirred and mixed at room temperature for 30 minutes. After that, the mixture was filtered with a membrane filter having an aperture of 5 μm to provide a photosensitive composition.

Examples 2 to 10 and Examples 2-1 to 2-10

Photosensitive compositions were each obtained in the same manner as in Example 1 except that the used fluorene-based compound and its usage were changed as shown in Table 2. It should be noted that the fluorene-based compound as a photopolymerization initiator was used in such an amount that its molar quantity was kept constant in the respective examples and comparative examples.

Comparative Examples 1 and 2

Photosensitive compositions were each obtained in the same manner as in Example 1 except that the photopolymerization initiator and its usage were changed as shown in Table 2.

Evaluation 1

Each of the photosensitive compositions obtained in Examples 1 to 9, Examples 2-1 to 2-10, and Comparative Example 1 was applied onto a glass substrate with a spin coater (manufactured by Kyowariken Co., Ltd., trade name: "K-359SD1") so that its thickness after drying became 1.0 μm. The glass substrate after the application was dried with a fan dryer at 90° C. for 10 minutes. Thus, a coating film (photosensitive layer) was formed. Next, the film was exposed to light having an exposure energy quantity of 5 mJ/cm$^2$, 10 mJ/cm$^2$, 20 mJ/cm$^2$, 40 mJ/cm$^2$, 60 mJ/cm$^2$, or 80 mJ/cm$^2$ by using a high-pressure mercury lamp (manufactured by Karl Suss, trade name: "MASK ALIGNER") through a negative mask (mask width: 20 μm). Next, the resultant was immersed in a 0.1 wt % aqueous solution of tetramethylammonium hydroxide (TMAH) and then rinsed with pure water. The remaining cured film was subjected to the following evaluation. The results are shown in Table 3. It should be noted that the composition of Comparative Example 1 could not form a cured film at an exposure energy quantity of 10 mJ/cm$^2$. FIGS. 2 to 11 show microscope photographs of transparent cured films obtained by using the photosensitive compositions of Examples 1, 2, 5, and 7, Comparative Example 1, and Examples 2-1, 2-2, 2-3, 2-7, and 2-8.

(20-μm Pattern Line Width)

A pattern image at each exposure energy quantity was observed with a color 3D laser microscope (manufactured by Keyence Corporation, trade name: "VK-X110") at a certain magnification (×2,000), and the width of the pattern was measured. A larger value for the line width means higher sensitivity.

TABLE 2

| | Photosensitive composition | | | |
|---|---|---|---|---|
| | | Photopolymerization initiator | | |
| Example | Photosensitive compound | Compound | Amount | Solvent |
| 1 | Acid group-containing acrylate | 1 | 0.192 part (0.4 mmol) | PGMEA |
| 2 | 13.2 parts | 2 | 0.226 part (0.4 mmol) | 6.0 parts |
| 3 | Dipentaerythritol hexaacrylate | 4 | 0.190 part (0.4 mmol) | |
| 4 | 0.4 part | 6 | 0.225 part (0.4 mmol) | |
| 5 | | 8 | 0.219 part (0.4 mmol) | |
| 6 | | 9 | 0.284 part (0.4 mmol) | |
| 7 | | 11 | 0.280 part (0.4 mmol) | |
| 8 | | 12 | 0.296 part (0.4 mmol) | |
| 9 | | 13 | 0.285 part (0.4 mmol) | |
| 2-1 | | D-1 | 0.188 part (0.4 mmol) | |
| 2-2 | | D-3 | 0.162 part (0.4 mmol) | |
| 2-3 | | D-4 | 0.185 part (0.4 mmol) | |
| 2-4 | | D-7 | 0.205 part (0.4 mmol) | |
| 2-5 | | D-8 | 0.205 part (0.4 mmol) | |
| 2-6 | | D-9 | 0.216 part (0.4 mmol) | |
| 2-7 | | D-12 | 0.188 part (0.4 mmol) | |
| 2-8 | | D-14 | 0.232 part (0.4 mmol) | |
| 2-9 | | D-15 | 0.238 part (0.4 mmol) | |
| 2-10 | | D-20 | 0.219 part (0.4 mmol) | |
| Comparative Example 1 | | C-1 | 0.168 part (0.4 mmol) | |
| Comparative Example 2 | | C-2 | 0.205 part (0.4 mmol) | |

TABLE 3

| | | | \multicolumn{6}{c|}{Example} |
|---|---|---|---|---|---|---|---|---|
| | | | 1 | 2 | 3 | 4 | 5 | 6 |
| | | | \multicolumn{6}{c|}{Compound (photopolymerization initiator)} |
| | | | 1 | 2 | 4 | 6 | 8 | 9 |
| 20-μm pattern line width | Exposure energy quantity (mJ/cm$^2$) | 10 | 20.7 | 21.4 | 19.4 | 19.7 | 19.6 | 19.9 |
| | | 20 | 21.6 | 22.3 | 20.0 | 20.2 | 20.1 | 20.5 |
| | | 40 | 22.6 | 22.9 | 21.3 | 21.1 | 21.7 | 21.3 |
| | | 60 | 23.3 | 23.9 | 22.1 | 21.7 | 22.7 | 22.2 |
| | | 80 | 23.8 | 24.4 | 22.4 | 22.7 | 23.0 | 22.8 |

| | | | \multicolumn{4}{c|}{Example} | \multicolumn{2}{c|}{Comparative Example} |
|---|---|---|---|---|---|---|---|---|
| | | | 7 | 8 | 9 | 2-1 | 1 | 2 |
| | | | \multicolumn{6}{c|}{Compound (photopolymerization initiator)} |
| | | | 11 | 12 | 13 | D-1 | C-1 | C-2 |
| 20-μm pattern line width | Exposure energy quantity (mJ/cm$^2$) | 10 | 19.9 | 19.8 | 19.4 | 20.2 | — | 21.3 |
| | | 20 | 20.5 | 20.0 | 19.6 | 20.9 | 20.4 | 22.3 |
| | | 40 | 21.9 | 21.0 | 19.8 | 22.4 | 22.1 | 23.6 |
| | | 60 | 22.5 | 21.2 | 20.6 | 22.8 | 22.3 | 23.5 |
| | | 80 | 22.8 | 21.5 | 21.0 | 23.1 | 22.4 | 24.0 |

| | | | \multicolumn{4}{c|}{Example} |
|---|---|---|---|---|---|---|
| | | | 2-2 | 2-3 | 2-4 | 2-5 |
| | | | \multicolumn{4}{c|}{Compound (photopolymerization initiator)} |
| | | | D-3 | D-4 | D-7 | D-8 |
| 20-μm pattern line width | Exposure energy quantity (mJ/cm$^2$) | 5 | 19.6 | 19.6 | 19.3 | 19.1 |
| | | 10 | 20.9 | 20.1 | 20.2 | 19.7 |
| | | 20 | 21.4 | 22.0 | 20.8 | 20.0 |
| | | 30 | \multicolumn{2}{c|}{No Data} | 21.4 | 21.3 |
| | | 40 | 22.5 | 22.7 | 22.6 | 21.9 |
| | | 80 | 23.8 | 23.4 | \multicolumn{2}{c|}{No Data} |

| | | | \multicolumn{5}{c|}{Example} |
|---|---|---|---|---|---|---|---|
| | | | 2-6 | 2-7 | 2-8 | 2-9 | 2-10 |
| | | | \multicolumn{5}{c|}{Compound (photopolymerization initiator)} |
| | | | D-9 | D-12 | D-14 | D-15 | D-20 |
| 20-μm pattern line width | Exposure energy quantity (mJ/cm$^2$) | 5 | 19.3 | 19.8 | 19.9 | 19.5 | 19.5 |
| | | 10 | 19.5 | 20.6 | 20.6 | 19.9 | 19.4 |
| | | 20 | 20.0 | 21.4 | 21.7 | 20.7 | 19.9 |
| | | 40 | 20.7 | 22.3 | 22.8 | 21.4 | 20.6 |
| | | 80 | 21.7 | 23.3 | 23.2 | 22.3 | 21.4 |

A photosensitive composition containing the fluorene-based compound of the present invention was able to form a pattern even when the exposure energy quantity was 10 mJ/cm$^2$. On the other hand, Comparative Example 1 as a photosensitive composition using a conventional photopolymerization initiator could not form a pattern when the exposure energy quantity was 10 mJ/cm$^2$. Further, when the exposure energy quantity was 80 mJ/cm$^2$, each of the photosensitive compositions of Examples 1 to 7, and Examples 2-1, 2-2, 2-3, 2-7, and 2-8 had sensitivity more excellent than that of the photosensitive composition of Comparative Example 1. Of those, the photosensitive compositions of Examples 1 and 2, and Example 2-2 each had particularly excellent sensitivity.

Evaluation 2

(Average Transmittance of Composition)

The average transmittance (%) of each of the photosensitive resin compositions obtained in Examples 1 to 9, Examples 2-1 to 2-10, and Comparative Examples 1 and 2 in the range of from 400 nm to 700 nm was measured with a spectrophotometer (manufactured by Hitachi High-Technologies Corporation, trade name: "U-3900H", quartz cell, optical path length; 1 cm). The results are shown in Table 4.

(Transmittance of Transparent Cured Film)

Transparent cured films were formed by using the photosensitive compositions obtained in Examples 1 to 9, Examples 2-1 to 2-10, and Comparative Examples 1 and 2 in the same manner as in the evaluation 1 except that the exposure energy quantity was set to 80 mJ/cm$^2$. The transmittance (%) of each of the resultant transparent cured films at 400 nm and the average transmittance (%) thereof in the range of from 400 to 700 nm were measured with a spectrophotometer (manufactured by Hitachi High-Technologies Corporation, trade name: "U-3900H", quartz cell, optical path length; 1 cm). A higher transmittance at 400 nm means less coloring with a yellow color. In addition, a higher transmittance of a coating film means a higher transmitting property of a pattern to be formed. The results are shown in Table 4.

TABLE 4

| Composition | Photo-polymerization initiator | Average transmittance (%) (700 nm to 400 nm) Solution | Transmittance (%) (400 nm) Transparent cured film |
|---|---|---|---|
| Example 1 | Compound 1 | 88.7 | 99.3 | 92.0 |
| Example 2 | Compound 2 | 87.5 | 99.3 | 92.8 |
| Example 3 | Compound 4 | 96.3 | 99.9 | 99.4 |
| Example 4 | Compound 6 | 95.4 | 97.3 | 99.6 |
| Example 5 | Compound 8 | 95.4 | 100.0 | 100.0 |
| Example 6 | Compound 9 | 94.0 | 100.0 | 99.4 |
| Example 7 | Compound 11 | 93.0 | 100.0 | 99.1 |
| Example 8 | Compound 12 | 77.8 | 99.8 | 99.7 |
| Example 9 | Compound 13 | 79.2 | 99.4 | 97.0 |
| Example 2-1 | Compound D-1 | 57.5 | 99.2 | 91.7 |
| Example 2-2 | Compound D-3 | 88.9 | 99.8 | 95.2 |
| Example 2-3 | Compound D-4 | 88.3 | 96.7 | 95.4 |
| Example 2-4 | Compound D-7 | 86.0 | 99.3 | 96.1 |
| Example 2-5 | Compound D-8 | 87.0 | 100.0 | 98.0 |
| Example 2-6 | Compound D-9 | 70.9 | 99.8 | 96.4 |
| Example 2-7 | Compound D-12 | 79.9 | 99.7 | 93.6 |
| Example 2-8 | Compound D-14 | 65.1 | 99.5 | 92.7 |
| Example 2-9 | Compound D-15 | 86.2 | 99.1 | 91.9 |
| Example 2-10 | Compound D-20 | 84.4 | 99.3 | 91.8 |
| Comparative Example 1 | Compound C-1 | 94.2 | 99.8 | 98.9 |
| Comparative Example 2 | Compound C-2 | 75.9 | 95.1 | 72.7 |

Each of the transparent cured films using Examples 1 to 9 and Examples 2-1 to 2-10 each using the fluorene-based compound of the present invention provided a coating film having transparency sufficient for practical use. In particular, when any one of the photosensitive compositions of Examples 3, 5, 6, 7, 8, and 2-5 was used, a transparent cured film having high transparency was obtained.

Evaluation of Black Photosensitive Composition

Example 10

0.196 Part by weight (0.4 mmol) of the fluorene-based compound (compound 1) obtained in Synthesis Example 1, 5.9 parts by weight of a cardo resin (whose solid content had been adjusted to 20 wt % with PGMEA), 0.4 part by weight of dipentaerythritol hexaacrylate (manufactured by Nippon Kayaku Co., Ltd., trade name: "KAYARAD DPHA"), 10 parts by weight of a PGMEA dispersion liquid of carbon black (solid content concentration: 20 wt %), and 3.5 parts by weight of PGMEA were mixed and stirred at room temperature for 30 minutes. The mixture was filtered with a membrane filter having an aperture of 5 μm to provide a photosensitive composition.

Examples 11 to 15 and Examples 2-11 to 2-20

Photosensitive compositions were each obtained in the same manner as in Example 10 except that the used fluorene-based compound and its usage were changed as shown in Table 5.

Comparative Example 3

Figure 2:
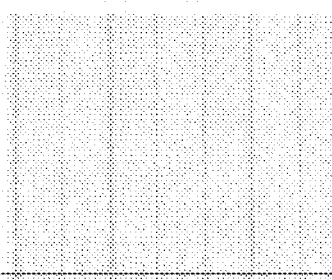
In FIG. 2, laser microscope photographs of a transparent cured film (Example 1) and a black cured film (Example 10) each obtained from a photosensitive composition containing a fluorene-based compound obtained in Synthesis Example 1 are shown.
Figure 3:
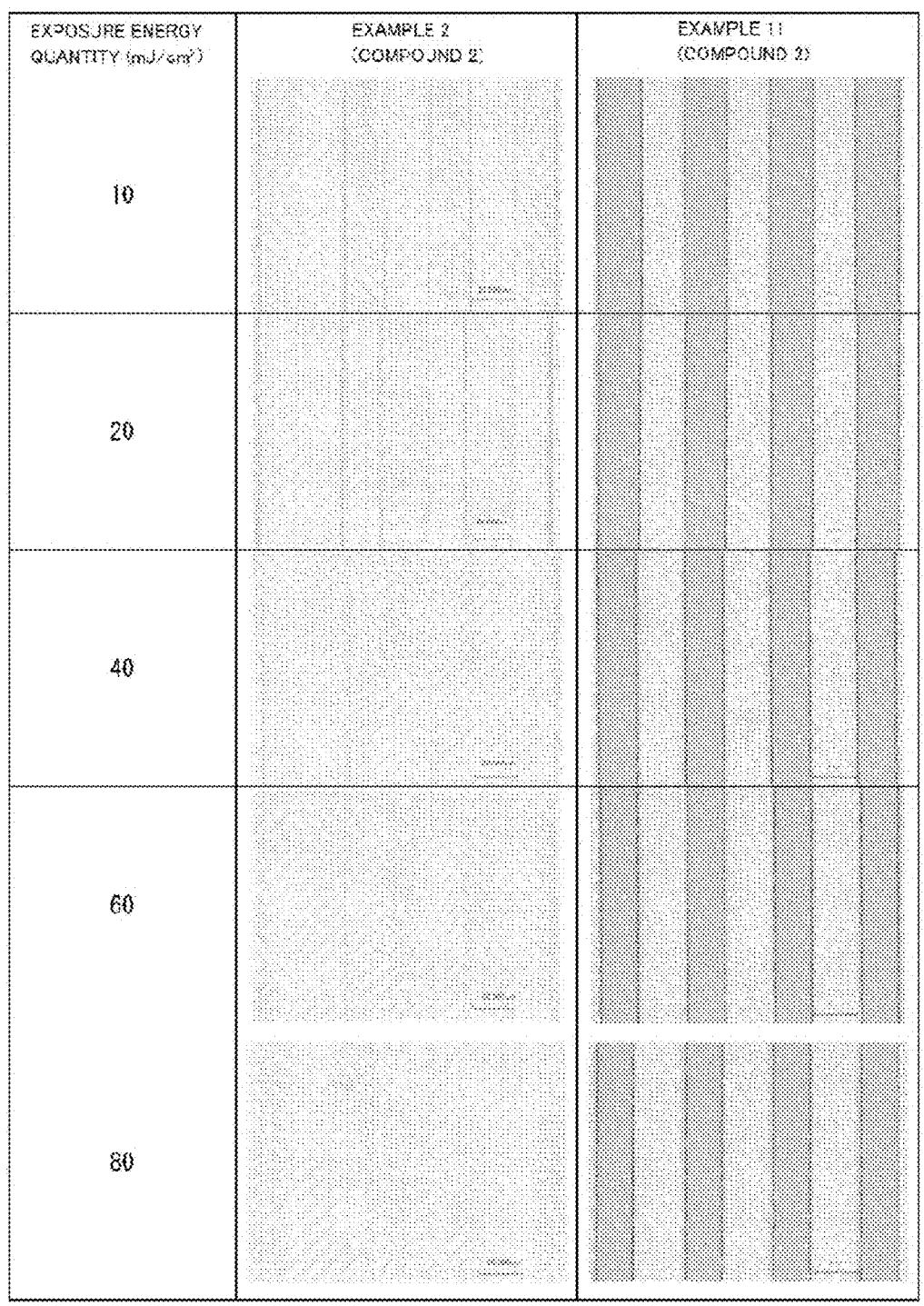
In FIG. 3, laser microscope photographs of a transparent cured film (Example 2) and a black cured film (Example 11) each obtained from a photosensitive composition containing a fluorene-based compound obtained in Synthesis Example 2 are shown.
Figure 4:
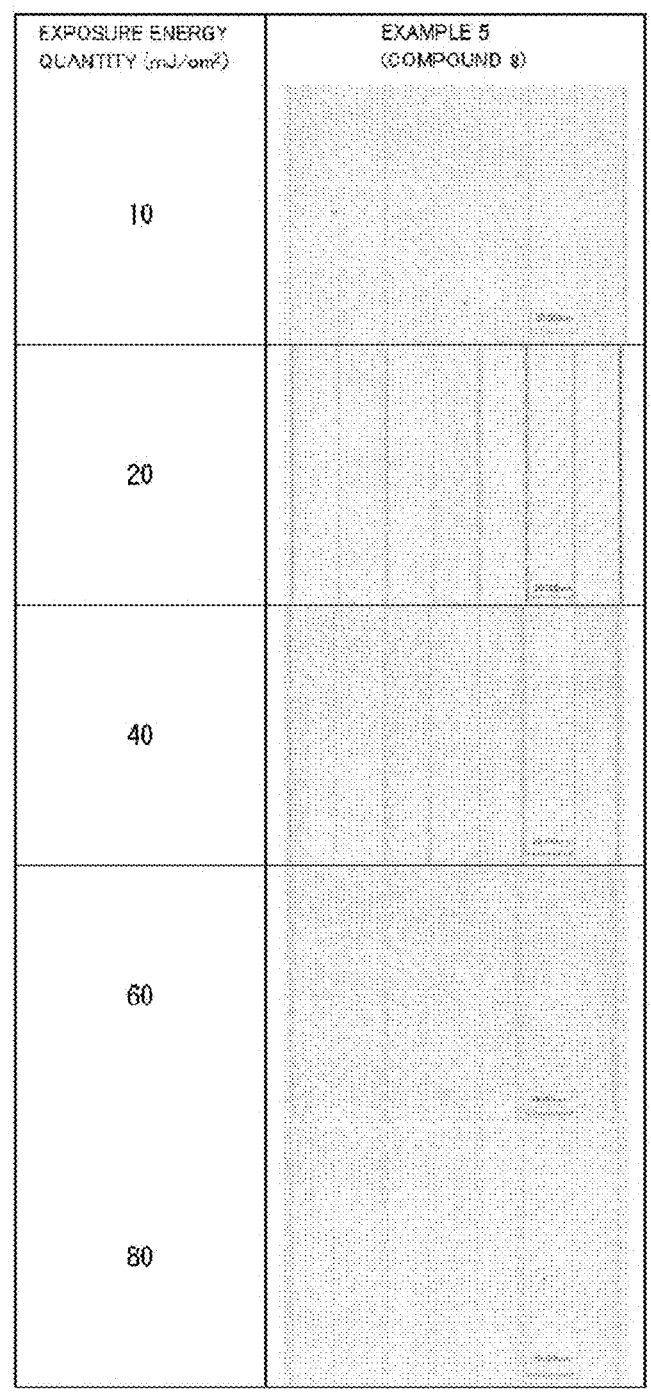
In FIG. 4, laser microscope photographs of a transparent cured film (Example 5) obtained from a photosensitive composition containing a fluorene-based compound obtained in Synthesis Example 8 are shown.
Figure 5:
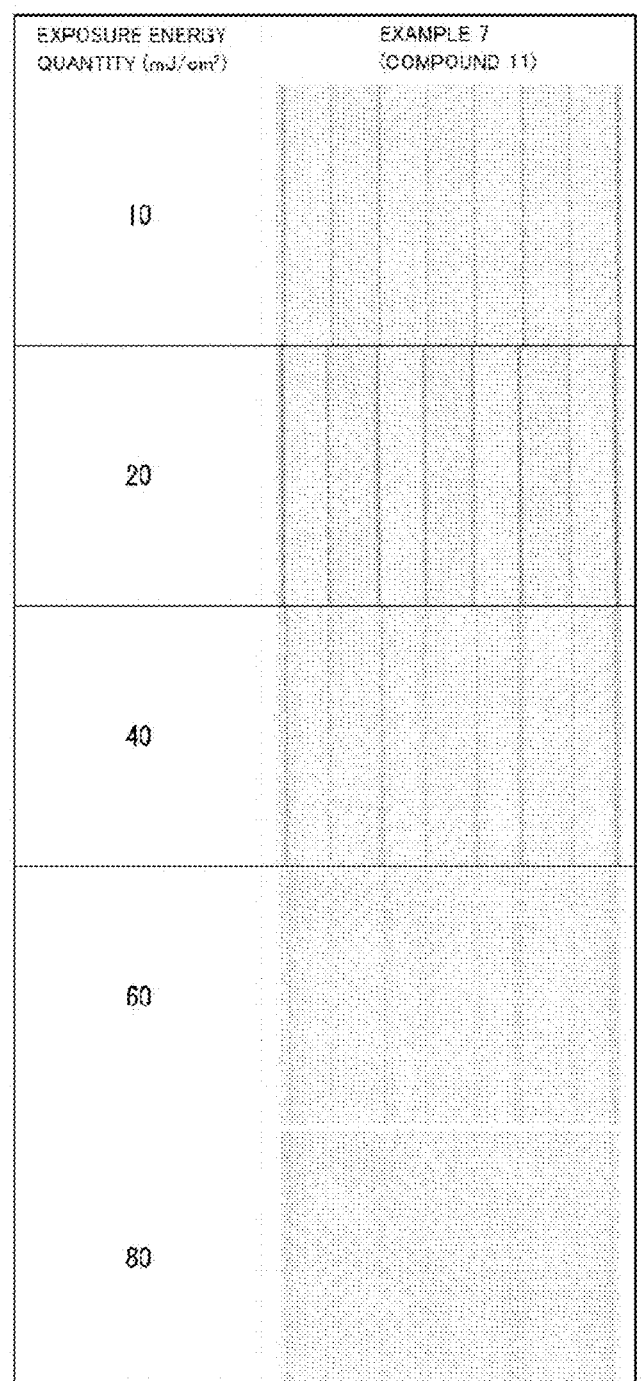
In FIG. 5, laser microscope photographs of a transparent cured film (Example 7) obtained from a photosensitive composition containing a fluorene-based compound obtained in Synthesis Example 11 are shown.

A photosensitive composition was obtained in the same manner as in Example 10 except that the photopolymerization initiator and its usage were changed as shown in Table 5.

ammonium hydroxide (TMAH) and then rinsed with pure water. The remaining cured film was subjected to the following evaluation. Tables 6 to 8 show the results. In addition, FIGS. 2, 3, and 6 show microscope photographs of black cured films obtained by using the photosensitive compositions of Examples 10 and 11, and Comparative Example 3, and FIGS. 7 to 11 show microscope photographs of black cured films obtained by using the photosensitive compositions of Examples 2-11, 2-13, 2-14, 2-17, and 2-18.

(20-μm Pattern Line Width)

A pattern image at each exposure energy quantity was observed with a color 3D laser microscope (manufactured by Keyence Corporation, trade name: "VK-X110") at a certain magnification (×2,000), and the width of the pattern was measured. A larger value for the line width means higher sensitivity.

(Straightness of Pattern)

The external appearance of a pattern image at each exposure energy quantity was visually evaluated. The case where a good linear pattern was formed was evaluated as good, and the case where the distortion of the pattern image or unevenness at an end portion thereof was observed was evaluated as bad.

TABLE 5

| | Photosensitive composition | | | | |
|---|---|---|---|---|---|
| | Photosensitive | Photopolymerization initiator | | Pigment | |
| Example | compound | Compound | Amount | dispersion liquid | Solvent |
| 10 | Cardo resin | 1 | 0.196 part (0.4 mmol) | CB dispersion | PGMEA |
| 11 | 5.9 parts | 2 | 0.231 part (0.4 mmol) | liquid | 3.5 parts |
| 12 | Dipentaerythritol | 4 | 0.195 part (0.4 mmol) | 10.0 parts | |
| 13 | hexaacrylate | 6 | 0.230 part (0.4 mmol) | | |
| 14 | 0.4 part | 8 | 0.224 part (0.4 mmol) | | |
| 15 | | 9 | 0.298 part (0.4 mmol) | | |
| 2-11 | | D-1 | 0.190 part (0.4 mmol) | | |
| 2-12 | | D-2 | 0.214 part (0.4 mmol) | | |
| 2-13 | | D-3 | 0.164 part (0.4 mmol) | | |
| 2-14 | | D-4 | 0.188 part (0.4 mmol) | | |
| 2-15 | | D-8 | 0.208 part (0.4 mmol) | | |
| 2-16 | | D-9 | 0.218 part (0.4 mmol) | | |
| 2-17 | | D-12 | 0.191 part (0.4 mmol) | | |
| 2-18 | | D-14 | 0.236 part (0.4 mmol) | | |
| 2-19 | | D-15 | 0.241 part (0.4 mmol) | | |
| 2-20 | | D-20 | 0.222 part (0.4 mmol) | | |
| Comparative Example 3 | | C-1 | 0.172 part (0.4 mmol) | | |

Evaluation 3

Each of the photosensitive compositions obtained in Examples 10 to 15, Examples 2-11 to 2-20, and Comparative Example 3 was applied onto a glass substrate with a spin coater (manufactured by Kyowariken Co., Ltd., trade name: "K-359SD1") so that its thickness after drying became 1.0 μm. The glass substrate after the application was dried with a fan dryer at 90° C. for 10 minutes. Thus, a coating film (photosensitive layer) was formed. Next, the film was exposed to light having an exposure energy quantity of 10 mJ/cm$^2$, 20 mJ/cm$^2$, 40 mJ/cm$^2$, 60 mJ/cm$^2$, or 80 mJ/cm$^2$ by using a high-pressure mercury lamp (manufactured by Karl Suss, trade name: "MASK ALIGNER") through a negative mask (mask width: 20 μm). Next, the resultant was immersed in a 0.1 wt % aqueous solution of tetra methyl (Peeling of Pattern)

The external appearance of a cured film after development by immersion in a 0.1% aqueous solution of TMAH was visually evaluated. The case where the external appearance did not change and the peeling of the cured film did not occur was evaluated as good.

(Residue)

The presence or absence of the residue of a coating film in an unexposed portion after development by immersion in a 0.1% aqueous solution of TMAH was visually evaluated. The case where the residue of the coating film in the unexposed portion was absent was evaluated as absent.

TABLE 6

| | | | \multicolumn{6}{c}{Example} | | | | | |
|---|---|---|---|---|---|---|---|---|
| | | | 10 | 11 | 12 | 13 | 14 | 15 |
| | | | \multicolumn{6}{c}{Compound (photopolymerization initiator)} | | | | | |
| | | | 1 | 2 | 4 | 6 | 8 | 9 |
| 20-μm pattern line width | Exposure energy quantity (mJ/cm$^2$) | 10 | 20.2 | 20.0 | 19.4 | 19.7 | 19.6 | 19.9 |
| | | 20 | 21.2 | 20.9 | 20.0 | 20.2 | 20.1 | 20.5 |
| | | 40 | 22.1 | 22.1 | 21.3 | 21.1 | 21.7 | 21.3 |
| | | 60 | 23.2 | 22.8 | 22.1 | 21.7 | 22.7 | 22.2 |
| | | 80 | 23.3 | 23.3 | 22.4 | 22.7 | 23.0 | 22.8 |
| Straightness | Exposure energy quantity (mJ/cm$^2$) | 10 | Good | Good | Bad | Bad | Bad | Bad |
| | | 20 | Good | Good | Good | Good | Good | Good |
| | | 40 | Good | Good | Good | Good | Good | Good |
| | | 60 | Good | Good | Good | Good | Good | Good |
| | | 80 | Good | Good | Good | Good | Good | Good |
| Peeling | Exposure energy quantity (mJ/cm$^2$) | 10 | Good | Good | Bad | Bad | Bad | Bad |
| | | 20 | Good | Good | Good | Good | Good | Good |
| | | 40 | Good | Good | Good | Good | Good | Good |
| | | 60 | Good | Good | Good | Good | Good | Good |
| | | 80 | Good | Good | Good | Good | Good | Good |
| Residue | Exposure energy quantity (mJ/cm$^2$) | 10 | Absent | Absent | Absent | Absent | Absent | Absent |
| | | 20 | Absent | Absent | Absent | Absent | Absent | Absent |
| | | 40 | Absent | Absent | Absent | Absent | Absent | Absent |
| | | 60 | Absent | Absent | Absent | Absent | Absent | Absent |
| | | 80 | Absent | Absent | Absent | Absent | Absent | Absent |

TABLE 7

| | | | \multicolumn{6}{c}{Example} | | | | | |
|---|---|---|---|---|---|---|---|---|
| | | | 2-11 | 2-12 | 2-13 | 2-14 | 2-15 | 2-16 |
| | | | \multicolumn{6}{c}{Compound (photopolymerization initiator)} | | | | | |
| | | | D-1 | D-2 | D-3 | D-4 | D-8 | D-9 |
| 20-μm pattern line width | Exposure energy quantity (mJ/cm$^2$) | 10 | 19.4 | 19.4 | 19.6 | 19.7 | 18.7 | 18.8 |
| | | 20 | 20.4 | 20.4 | 20.6 | 20.5 | 18.7 | 19.1 |
| | | 40 | 21.9 | 21.6 | 21.6 | 21.5 | 20.0 | 20.1 |
| | | 60 | 22.3 | 22.1 | 22.1 | 22.5 | 20.7 | 20.9 |
| | | 80 | 23.1 | 23.0 | 22.6 | 22.8 | 21.1 | 21.2 |
| Straightness | Exposure energy quantity (mJ/cm$^2$) | 10 | Good | Good | Good | Good | Good | Good |
| | | 20 | Good | Good | Good | Good | Good | Good |
| | | 40 | Good | Good | Good | Good | Good | Good |
| | | 60 | Good | Good | Good | Good | Good | Good |
| | | 80 | Good | Good | Good | Good | Good | Good |
| Peeling | Exposure energy quantity (mJ/cm$^2$) | 10 | Good | Good | Good | Good | Good | Good |
| | | 20 | Good | Good | Good | Good | Good | Good |
| | | 40 | Good | Good | Good | Good | Good | Good |
| | | 60 | Good | Good | Good | Good | Good | Good |
| | | 80 | Good | Good | Good | Good | Good | Good |
| Residue | Exposure energy quantity (mJ/cm$^2$) | 10 | Absent | Absent | Absent | Absent | Absent | Absent |
| | | 20 | Absent | Absent | Absent | Absent | Absent | Absent |
| | | 40 | Absent | Absent | Absent | Absent | Absent | Absent |
| | | 60 | Absent | Absent | Absent | Absent | Absent | Absent |
| | | 80 | Absent | Absent | Absent | Absent | Absent | Absent |

TABLE 8

| | | | \multicolumn{4}{c}{Example} | | | | Comparative Example |
|---|---|---|---|---|---|---|---|
| | | | 2-17 | 2-18 | 2-19 | 2-20 | 3 |
| | | | \multicolumn{5}{c}{Compound (photopolymerization initiator)} | | | | |
| | | | D-12 | D-14 | D-15 | D-20 | C-1 |
| 20-μm pattern line width | Exposure energy quantity (mJ/cm$^2$) | 10 | 19.1 | 19.9 | 19.5 | 19.1 | 18.5 |
| | | 20 | 20.5 | 20.6 | 19.9 | 19.7 | 19.0 |
| | | 40 | 21.6 | 21.7 | 20.7 | 20.5 | 20.0 |
| | | 60 | 22.5 | 22.8 | 21.4 | 21.3 | 20.9 |
| | | 80 | 22.7 | 23.2 | 22.3 | 21.8 | 21.2 |
| Straightness | Exposure energy quantity (mJ/cm$^2$) | 10 | Good | Good | Good | Good | Bad |
| | | 20 | Good | Good | Good | Good | Good |

TABLE 8-continued

|  |  |  | Example | | | | Comparative Example |
|---|---|---|---|---|---|---|---|
|  |  |  | 2-17 | 2-18 | 2-19 | 2-20 | 3 |
|  |  |  | Compound (photopolymerization initiator) | | | | |
|  |  |  | D-12 | D-14 | D-15 | D-20 | C-1 |
|  |  | 40 | Good | Good | Good | Good | Good |
|  |  | 60 | Good | Good | Good | Good | Good |
|  |  | 80 | Good | Good | Good | Good | Good |
| Peeling | Exposure energy | 10 | Good | Good | Good | Good | Bad |
|  | quantity (mJ/cm²) | 20 | Good | Good | Good | Good | Good |
|  |  | 40 | Good | Good | Good | Good | Good |
|  |  | 60 | Good | Good | Good | Good | Good |
|  |  | 80 | Good | Good | Good | Good | Good |
| Residue | Exposure energy | 10 | Absent | Absent | Absent | Absent | Absent |
|  | quantity (mJ/cm²) | 20 | Absent | Absent | Absent | Absent | Absent |
|  |  | 40 | Absent | Absent | Absent | Absent | Absent |
|  |  | 60 | Absent | Absent | Absent | Absent | Absent |
|  |  | 80 | Absent | Absent | Absent | Absent | Absent |

In the evaluation for a 20-μm pattern line width, the photosensitive compositions of Examples 10 to 15 and Examples 2-11 to 2-20 were able to form patterns at any exposure energy quantity. Of those, Examples 10 and 11, and Examples 2-11 to 2-14 and 2-17 to 2-20 each showed sensitivity higher than that of Comparative Example 3 using a conventional photopolymerization initiator at each of all the exposure energy quantities. In the evaluations for the straightness of a pattern, the peeling of the pattern, and a residue, Examples 10 and 11, and Examples 2-11 to 2-14 and 2-17 to 2-20 similarly showed results better than those of Comparative Example 3 using the conventional photopolymerization initiator.

INDUSTRIAL APPLICABILITY

The fluorene-based compound of the present invention can be suitably used as a photopolymerization initiator. The fluorene-based compound of the present invention can be suitably used in various applications because the compound has high sensitivity. A photopolymerization initiator containing the fluorene-based compound of the present invention exhibits performance equal to or higher than that of a conventional photopolymerization initiator. In addition, the use of a fluorene-based compound serving as a photopolymerization initiator having additionally high sensitivity enables the maintenance of performance comparable to that of the conventional photopolymerization initiator even when the usage of the photopolymerization initiator is reduced, and hence can reduce a cost in the production of a photosensitive composition. Further, the use of the fluorene-based compound having additionally high sensitivity can reduce exposure energy at the time of a reaction and can also reduce energy consumption.

The invention claimed is:

1. A fluorene-based compound, which is represented by the general formula (1):

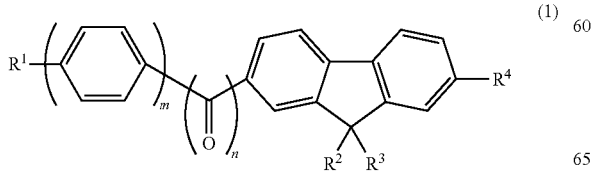

(1)

in the general formula (1):
when m represents 0 and n represents 0, $R^1$ represents a hydrogen atom, a halogen atom, a nitro group, a sulfonyloxy group substituted with an alkyl group having 1 to 8 carbon atoms that may be substituted with a halogen atom, a phenylsulfonyloxy group that may be substituted, a sulfonyl group substituted with an alkyl group having 1 to 8 carbon atoms that may be substituted with a halogen atom, a phenylsulfonyl group that may be substituted, a heterocyclic sulfonyl group that may be substituted, or a condensed ring sulfonyl group that may be substituted, when m represents 0 and n represents 1, $R^1$ represents a phenyl group that may be substituted, a heterocyclic group that may be substituted, or a condensed ring group that may be substituted, and when m represents 1 and n represents 1, $R^1$ represents a sulfonyloxy group substituted with an alkyl group having 1 to 8 carbon atoms that may be substituted with a halogen atom, or a phenylsulfonyloxy group that may be substituted;

$R^2$ and $R^3$ each independently represent, a linear or branched halogenated alkyl group having 1 to 10 carbon atoms, or a linear or branched alkyl group having 2 to 9 carbon atoms interrupted by one or more ether bonds, and $R^2$ and $R^3$ may form a ring together;

$R^4$ represents a group represented by the formula (2):

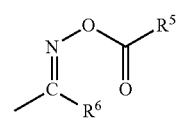

(2)

in the formula (2) $R^5$ represents a linear, branched, or cyclic alkyl group having 1 to 17 carbon atoms, a linear or branched halogenated alkyl group having 2 to 5 carbon atoms, a linear or branched alkyl group having 2 to 7 carbon atoms interrupted by one or more ether bonds or thioether bonds, a phenyl group that may be substituted, a phenylalkyl group having 7 to 11 carbon atoms that may be substituted, a phenoxyalkyl group having 7 to 10 carbon atoms that may be substituted, a heterocyclic group that may be substituted, or a condensed ring group that may be substituted, in the formula (2), $R^6$ represents a branched, or cyclic alkyl group having 3 to 17 carbon atoms, a linear or branched halogenated alkyl group having 1 to 7 carbon atoms, a linear or branched alkyl group having 2 to 7 carbon atoms interrupted by one or more ether bonds or thioether bonds, a linear or branched aminoalkyl group having 2 to 3 carbon atoms that may be substituted, a phenyl group that may be substituted, a condensed ring group that may be substituted, or a heterocyclic group that may be substituted, and m and n each represent 0 or 1, and when m represents 1, n represents 1.

2. The fluorene-based compound according to claim 1, wherein the $R^5$ represents a methyl group.

3. The fluorene-based compound according to claim 1, wherein the $R^4$ represents a group represented by the formula (2), and the $R^6$ represents a branched or cyclic alkyl group having 3 to 17 carbon atoms, a linear or branched halogenated alkyl group having 1 to 5 carbon atoms, a phenyl group that may be substituted, a condensed ring group that may be substituted, or a heterocyclic group that may be substituted.

4. The fluorene-based compound according to claim 1, wherein:
the m and the n each represent 0, and the $R^1$ represents a halogen atom or a nitro group; or
the m represents 0 and the n represents 1, and the $R^1$ represents a phenyl group that may be substituted, a condensed ring group that may be substituted, or a heterocyclic group that may be substituted.

5. A photopolymerization initiator, comprising at least one kind of the fluorene-based compound of claim 1.

6. A photosensitive composition, comprising:
a compound having at least one ethylenically unsaturated bond; and
the photopolymerization initiator of claim 5.

7. A fluorene-based compound, which is represented by the general formula (1):

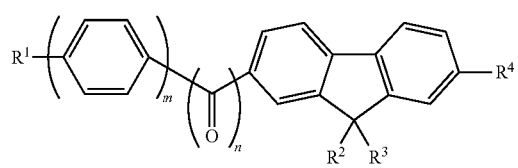

(1)

in the general formula (1):
when m represents 0 and n represents 0, $R^1$ represents a hydrogen atom, a halogen atom, a nitro group, a sulfonyloxy group substituted with an alkyl group having 1 to 8 carbon atoms that may be substituted with a halogen atom, a phenylsulfonyloxy group that may be substituted, a sulfonyl group substituted with an alkyl group having 1 to 8 carbon atoms that may be substituted with a halogen atom, a phenylsulfonyl group that may be substituted, a heterocyclic sulfonyl group that may be substituted, or a condensed ring sulfonyl group that may be substituted, when m represents 0 and n represents 1, $R^1$ represents a phenyl group that may be substituted, a heterocyclic group that may be substituted, or a condensed ring group that may be substituted, and when m represents 1 and n represents 1, $R^1$ represents a sulfonyloxy group substituted with an alkyl group having 1 to 8 carbon atoms that may be substituted with a halogen atom, or a phenylsulfonyloxy group that may be substituted;

$R^2$ and $R^3$ each independently represent a hydrogen atom, a linear, branched, or cyclic alkyl group having 1 to 22 carbon atoms, a linear or branched halogenated alkyl group having 1 to 10 carbon atoms, or a linear or branched alkyl group having 2 to 15 carbon atoms interrupted by one or more ether bonds or thioether bonds, and $R^2$ and $R^3$ may form a ring together;

wherein the $R^4$ represents a group represented by the formula (3):

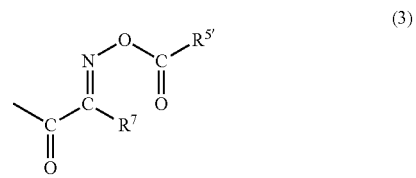

(3)

in the formula (3), $R^{5'}$ represents a linear, branched, or cyclic alkyl group having 1 to 17 carbon atoms, a linear or branched halogenated alkyl group having 2 to 5 carbon atoms, a linear or branched alkyl group having 2 to 7 carbon atoms interrupted by one or more ether bonds or thioether bonds, a phenyl group that may be substituted, a phenylalkyl group having 7 to 11 carbon atoms that may be substituted, a phenoxyalkyl group having 7 to 10 carbon atoms that may be substituted, a heterocyclic group that may be substituted, or a condensed ring group that may be substituted, and the $R^7$ represents a linear, branched, or cyclic alkyl group having 1 to 6 carbon atoms, a linear or branched halogenated alkyl group having 1 to 4 carbon atoms, a phenyl group that may be substituted, a phenylalkyl group having 7 to 10 carbon atoms that may be substituted, a phenylalkyl group having 7 to 9 carbon atoms that is interrupted by one or more ether bods or thioether bonds and may be substituted, a condensed ring group that may be substituted, or a heterocyclic group that may be substituted.

8. A fluorene-based compound, which is represented by the general formula (1):

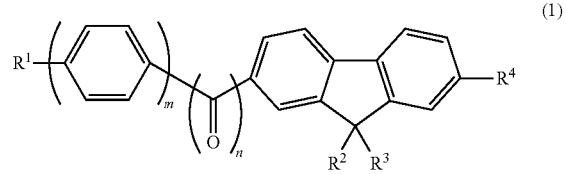

(1)

in the general formula (1):
when m represents 0 and n represents 0, $R^1$ represents a hydrogen atom, a halogen atom, a nitro group, a sulfonyloxy group substituted with an alkyl group having 1 to 8 carbon atoms that may be substituted with a halogen atom, a phenylsulfonyloxy group that may be substituted, a sulfonyl group substituted with an alkyl group having 1 to 8 carbon atoms that may be substituted with a halogen atom, a phenylsulfonyl group that may be substituted, a heterocyclic sulfonyl group that may be substituted, or a condensed ring sulfonyl group that may be substituted, when m represents 0 and n represents 1, $R^1$ represents a phenyl group that may be substituted, a heterocyclic group that may be substituted, or a condensed ring group that may be substituted, and when m represents 1 and n represents 1, $R^1$ represents a sulfonyloxy group substituted with an alkyl group having 1 to 8 carbon atoms that may be substituted with a halogen atom, or a phenylsulfonyloxy group that may be substituted;

$R^2$ and $R^3$ each independently represent a hydrogen atom, a linear, branched, or cyclic alkyl group having 1 to 22 carbon atoms, a linear or branched halogenated alkyl group having 1 to 10 carbon atoms, or a linear or branched alkyl group having 2 to 15 carbon atoms interrupted by one or more ether bonds or thioether bonds, and $R^2$ and $R^3$ may form a ring together;

wherein the $R^4$ represents a group represented by the formula (3):

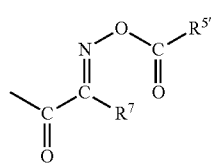

(3)

in the formula (3), $R^{5'}$ represents a linear, branched, or cyclic alkyl group having 1 to 17 carbon atoms, a linear or branched halogenated alkyl group having 2 to 5 carbon atoms, a linear or branched alkyl group having 2 to 7 carbon atoms interrupted by one or more ether bonds or thioether bonds, a phenyl group that may be substituted, a phenylalkyl group having 7 to 11 carbon atoms that may be substituted, a phenoxyalkyl group having 7 to 10 carbon atoms that may be substituted, a heterocyclic group that may be substituted, or a condensed ring group that may be substituted, and the $R^7$ represents a linear, branched, or cyclic alkyl group having 1 to 16 carbon atoms, a linear or branched halogenated alkyl group having 1 to 6 carbon atoms, a phenyl group that may be substituted, a phenylalkyl group having 7 to 10 carbon atoms that may be substituted, a phenylalkyl group having 7 to 9 carbon atoms that is interrupted by one or more ether bonds or thioether bonds and may be substituted, a condensed ring group that may be substituted, or a heterocyclic group that may be substituted; and m and n each represent 0 or 1, and when m represents 1, n represents 1.

9. The fluorene-based compound of claim 8, wherein:

$R^2$ and $R^3$ each independently represent a hydrogen atom, a linear, branched, or cyclic alkyl group having 1 to 22 carbon atoms, a linear or branched halogenated alkyl group having 1 to 10 carbon atoms, or a linear or branched alkyl group having 2 to 9 carbon atoms interrupted by one or more ether bonds, and $R^2$ and $R^3$ may form a ring together; and $R^7$ represents a linear, branched, or cyclic alkyl group having 1 to 6 carbon atoms, a linear or branched halogenated alkyl group having 1 to 4 carbon atoms, a phenyl group that may be substituted, a condensed ring group that may be substituted, or a heterocyclic group that may be substituted.

10. The fluorene-based compound according to claim 8, wherein the $R^{5'}$ represents a methyl group.

11. The fluorene-based compound according to claim 8, wherein:

the m and the n each represent 0, and the R' represents a halogen atom or a nitro group; or the m represents 0 and the n represents 1, and the R' represents a phenyl group that may be substituted, a condensed ring group that may be substituted, or a heterocyclic group that may be substituted.

12. A photopolymerization initiator, comprising at least one kind of the fluorene-based compound of claim 8.

13. A photosensitive composition, comprising:

a compound having at least one ethylenically unsaturated bond; and the photopolymerization initiator of claim 12.

* * * * *

UNITED STATES PATENT AND TRADEMARK OFFICE
CERTIFICATE OF CORRECTION

PATENT NO. : 9,684,238 B2
APPLICATION NO. : 14/431813
DATED : June 20, 2017
INVENTOR(S) : Makoto Harihara, Tomohiko Yamazaki and Katsuji Kuwamura It is certified that error appears in the above-identified patent and that said Letters Patent is hereby corrected as shown below:

In the Claims

Column 84, Lines 51-58 (Claim 1),

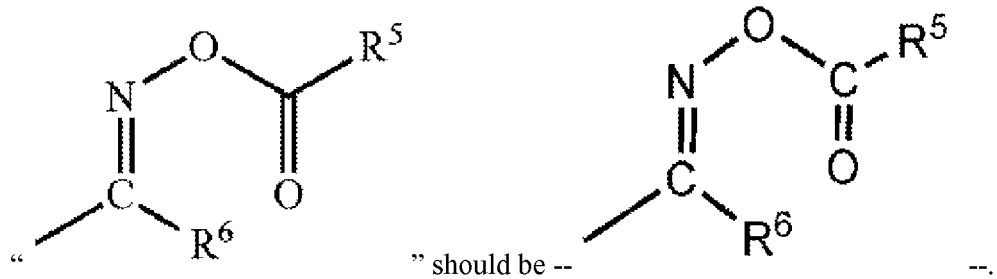

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*